(12) United States Patent
Diamond et al.

(10) Patent No.: US 8,808,216 B2
(45) Date of Patent: Aug. 19, 2014

(54) APPARATUS FOR USE WITH A PROTECTIVE CUP

(75) Inventors: Craig H. Diamond, Highland Park, IL (US); Alexander Coriano, III, Brisbane, CA (US)

(73) Assignee: Craig H. Diamond, Highland Park, IL (US)

(*) Notice: Subject to any disclaimer, the term of this patent is extended or adjusted under 35 U.S.C. 154(b) by 1285 days.

(21) Appl. No.: 12/617,489

(22) Filed: Nov. 12, 2009

(65) Prior Publication Data

US 2011/0009794 A1 Jan. 13, 2011

Related U.S. Application Data

(60) Provisional application No. 61/270,501, filed on Jul. 9, 2009.

(51) Int. Cl.
*A61F 13/00* (2006.01)
*A41C 1/00* (2006.01)
*A41B 9/02* (2006.01)

(52) U.S. Cl.
USPC .................... 602/67; 450/100; 2/403

(58) Field of Classification Search
USPC ................ 602/67–73; 450/100, 102, 1, 114; 2/403, 466
See application file for complete search history.

(56) References Cited

U.S. PATENT DOCUMENTS

| | | | | |
|---|---|---|---|---|
| 3,963,022 | A * | 6/1976 | Rotello | ............................ 602/70 |
| 4,660,554 | A | 4/1987 | Wright | |
| 4,989,594 | A | 2/1991 | Doherty et al. | |
| 5,479,942 | A * | 1/1996 | DiMatteo | ...................... 128/846 |
| 6,041,441 | A | 3/2000 | Counts et al. | |
| 7,178,176 | B1 | 2/2007 | S-Cronenbold | |
| 7,296,307 | B2 | 11/2007 | Atwater et al. | |
| D572,430 | S | 7/2008 | Wong | |
| 7,418,743 | B2 * | 9/2008 | Tsujimoto | ......................... 2/466 |
| 7,716,755 | B1 * | 5/2010 | Wiens | ................................. 2/466 |
| 8,245,327 | B2 * | 8/2012 | Wilson, II | ......................... 2/466 |
| 2008/0016605 | A1 | 1/2008 | Wong | |

OTHER PUBLICATIONS

Resurgence Fight Shorts—Jaco Clothing. http://www.jacoclothing.com/shop/resurgence-fight-shorts.html, 6 pages, dated Aug. 30, 2009.
Duke Athletic Products, http://www.dukeathletic.com/athletic-products/17/Compression-Shorts-and-Girdles, 5 pages, dated Jul. 15, 2010.
Guardian MMA Compression Shorts and Athletic Cup Protection System—Jaco Clothing, http:// www.jacoclothing.com/shop/guardian-mma-compression-short.html, 7 pages, dated Aug. 30, 2009.

(Continued)

*Primary Examiner* — Patricia Bianco
*Assistant Examiner* — Tarla Patel
(74) *Attorney, Agent, or Firm* — Quarles & Brady LLP

(57) ABSTRACT

An apparatus for use with a protective cup is disclosed. The apparatus includes a plurality of support members which may position the protective cup in a preferred position relative to a user's body, and secure the protective cup in the preferred position. The plurality of support members may connect to the protective cup or a protective support configured to receive the protective cup. The apparatus may be configured to protect the user's groin region, such as the user's crotch area, pubic bone and genitals. The apparatus may also be configured to protect the user's buttocks or legs, such as the user's hips, thighs, shins or knees.

6 Claims, 32 Drawing Sheets

(56) References Cited

OTHER PUBLICATIONS

MMA Groin Protection Steel Cups MMA Gear, http://www.cagesidemma.com/grpr.html, 3 pages, dated Jul. 22, 2009.
Flarico Brief Supporter with Flex Cup at International Jock Underwear & Swimwear, http://www.Internationaljock.com/flarico-brief-supporter-with-flex-cup.1674.html, 1 page, dated Aug. 22, 2009.
All Star Super Sport Shorts at International Jock Underwear & Swimwear, http://www.internationaljock.com/all-star-super-shorts.3550.html, 1 page, dated Aug. 22, 2009.
Bike Performance Elite Hard Cup Jockstrap at International Jock Underwear & Swimwear, http://www.Internationaljock.com/bike-performance-elite-hard-cup-jockstrap.1574.html, 1 page, dated Aug. 22, 2009.
Safe-T-Gard Thong Jockstraps at International Jock Underwear & Swimwear, http://www.Internationaljock.com/safe-t-gard-thong-jockstraps.7508.html, 1 page, dated Aug. 22, 2009.
WSI Sports 3941NS Inflator UltraJoc Slider, http://www.Baseballrampage.com/Baseball/Baseball-Clothing/Baseball-Clothing/134/134/..., 1 page, dated Aug. 22, 2009.
All-Star Shock Jock Cup and Supporter at International Jock Underwear & Swimwear, http://www.Internationaljcok.com/all-star-shock-jock-cup-and-supporter.3535.html, 1 page, dated Aug. 22, 2009.
Winwell Classic pro Athletic Supporter with Bike Cup at International Jock Underwear & ..., http://www.Internationaljock.com/winwell-classic-pro-athletic-supporter-with-bike-cup.35..., 1 page, dated Aug. 22, 2009.
Jofa Hockey Cup at International Jock Underwear & Swimwear, http://www.Internationaljock.com/jofa-hockey-cup.3520.html, 1 page, dated Aug. 22, 2009.
Shock Doctor X-Fit™ Support with Flex Cup-Combatsports.com, http://www.Combatsports.com/prodinfo.asp?Number=SDCUP 4, 1 page, dated Aug. 22, 2009.
Windy Steel Cup-Combatsports.com., http://www.Combatsports.com/prodinfo,asp?number=CUP 4. 1 page, dated Aug. 22, 2009.
Budovideos.com—Fairtex Muay Thai Steel Cup, http://www.Budovideos.com/shop/customer/product.php?productid=25506&cat=500&pag..., 1 page, dated Aug. 22, 2009.
Shock Doctor Power Sliding Short at International Jock Underwear & Swimwear, http:/www.Internationaljock.com/shock-doctor-power-sliding-short.3541.html, 1 page, dated Aug. 22, 2009.
Martial Arts Supplies Weapons Equipment Uniforms and Gear Quarter Century Martial ..., http: //www.Sakuramartialarts.com/Martial_Arts_Protect_Gear-Groin_Guard_TPR_Cup_p/..., 1 page, dated Aug. 22, 2009.
Martial Arts Supplies Weapons Equipment Uniforms and Gear Quarter Century Martial ..., http://www.Sakuramartialarts.com/Martial_Arts_Protect_Gear-Adidas_Groin_Guard_p/pr..., 1 page, dated Aug. 22, 2009.
Adult Flex-Cup, http:// store. Sawsports.com/adultflexcup.html, 2 pages, dated Aug. 22, 2009.
XO Athletic Teen Pro Cup with Compression / Sliding Short Supporter—Jockstraps. Athl..., http://www.Sportsunlimitedinc.com/xo303tcupshort.html, 3 pages, dated Aug. 22, 2009.
Reebok Hockey >> Gear >> Player (en) (weight 0) >> Jock Shorts in Player (en) (weight 0)>> ..., http://www.Reebokhockey.com/gear/products/player/jock-shorts/product/9k-jock-short/, 1 page, dated Aug. 22, 2009.
Reebok Hockey >> Gear >> Player (en) (weight 0) >> Jock Shorts in Player (en) (weight 8)>> ..., http://www.Reebokhockey.com/gear/products/player/jock-shorts/product/6k-jock-short/, 1 page, dated Aug. 22, 2009.
Reebok Hockey >> Gear >> Player (en) (weight 0) >> Jock Shorts in Player (en) (weight 8)>> ..., http://www.Reebokhockey.com/gear/products/player/jock-shorts/product/9k-jock-short/, 1 page, dated Aug. 22, 2009.
Under Armour & Men's Performance Jock with Cup Pocket / 1000271 / $14.99, http://www.Underarmour.com/shop/us/en/search/results/pid1000271-Men-s-Performance-J..., 1 page, dated Aug. 22, 2009.
Bike Men's Athletic Supporter—In New Packaging for Your Package—Bike Performance http://www.Sportsunlimitedinc.com/bike-brief-mens-athletic-supporter-proflex-max-cup-n..., 1 page, dated Aug. 22, 2009.
Athletic Sports Cup Safety Equipment Protection, http://www.Nuttbuddy.com/info-safety.html, 3 pages, dated Aug. 22, 2009.
Title Groin Protector Plus, http://www.Titlemma.com/c_4/p_GPP+S.aspx, 1 page, dated Aug. 22, 2009.
Twins Steel Cup > Protective Gear > Title MMA, http://www.Titlemma.com/c_4/p_GPS1+M.aspx, 1 page, dated Aug. 22, 2009.
Title MMA Steel Cup, http://www.Titlemma.com/sf_31/c_4/p_MMSC+S.aspx, 1 page, dated Aug. 22, 2009.
Core Supporter with Bioflex Cup, http://www.Shockdoctor.com/product/core-supporter-with-bioflex-cup.aspx, 1 page, dated Aug. 22, 2009.
Titan Alloy Flex Cup, http://www.Shockdoctor.com/product/titan-alloy-flex-cup-aspx, 1 page, dated Aug. 22, 2009.
Ultra Brief with Ultra Carbon Flex Cup, http://www.Sockdoctor.com/product/ultra-brief-with-ultra-carbon-flex-cup.aspx, 1 page, dated Aug. 22, 2009.
Core Double Compression Short with Bioflex Cup, http://www.Shockdoctor.com/product/core-double-compression-short-with-bioflex-cup.aspx, 1 page, dated Aug. 22, 2009.
Core Compression Short with Bioflex Cup, http://www.Shockdoctor/.com/product/core-compressin-short-with-bioflex-cup-aspx, 1 page, dated Aug. 22, 2009.
Basix Double Layer Thigh Compression Short with Bioflex Cup, http://www.Shockdoctor.com/prpoduct/basix-double-layer-thigh-compression-short-with-bi..., 1 page, dated Aug. 22, 2009.
Warrior Nutt Hutt Ice Adult Cup, http://www.Hockeymonkey.com/warrior-hockey-ug-jock-nutt-hutt-ice-adult.html, 2 pages, dated Aug. 24, 2009.
Reebok 6K Jr. Jock Short, http://www.Hockeymonkey.com/reebok-hockey-6K-jock-short-2009-jr.html, 1 page, dated Aug. 24, 2009.
Shock Doctor 202 Power Carbon Adult Cup, http://www.Hockeymonkey.com/shockdoc-hockey-carboncup-adult.html, 1 page, dated Aug. 24, 2009.
RBK, http:// ep .ying.com/ca/1/hockeymonkey_2067_356133442, 1 page, dated Aug. 24, 2009.
RBK Sr. Performance Jock Strap. http://www.Hockeymonkey.com/rbk-hockey-performance-jock-strap-sr-08.html, 1 page, dated Aug. 24, 2009.
Ultra Carbon Flex Cup, http://www.Shockdoctor.com/product/ultra-carbon-flex-cup.aspx, 1 page, dated Aug. 22, 2009.
Core Hockey Jock with Bioflex™ Cup, http://www.Shockdoctor.com/product/core-hockey-jock-with-bioflex-cup.aspx, 1 page, dated Aug. 22, 2009.
Shock Doctor Sports Equipment Protection Technology—Power Dry™ Crush Tech™ http://www.Shockdoctor.com/technology,aspx, 2 pages, dated Aug. 22, 2009.
Core Compression Short with Cup Pocket, http://www.Shockdoctor.com/product/core-compression-short-with-cup-pocket.aspx, 1 page, dated Aug. 22, 2009.

* cited by examiner

APPARATUS FOR USE WITH A PROTECTIVE CUP

PRIORITY

This application is a non-provisional of, claims the benefit of and priority to U.S. Provisional Application No. 61/270,501, filed Jul. 9, 2009, the entire contents of which are incorporated herein by reference.

TECHNICAL FIELD

The present application relates in general to a protective apparatus, and more specifically, to a wearable protective garment for use with a protective cup.

BACKGROUND

Protective cups and other devices are typically used to protect a user's groin region, e.g., the user's crotch area, pubic bone and genitals, during the performance of sports, physical activities or non-athletic occupations and activities. Protective cups are used by male and female adults as well as children. Typically, a protective cup protects the user during activities in which that user may be susceptible to impacts to the groin region. The protective cup typically covers a user's genitals, for example, such that the user's genitals are positioned inside the protective cup and an impact to the protective cup is absorbed by the area around the user's genitals rather than the user's genitals themselves.

Certain users have inserted a protective cup into a pair of shorts or pants without a jock with the protective cup may be free standing from the shorts or pants. Typically, the shorts or pants do not hold the cup firmly and tightly against the user's body. The non-secured cup may cause the cup to move relative to the user's genitals, which may result in serious injury and pain for the user.

Typically, an athletic supporter or jock holds a protective cup to protect a user's groin region from impacts. A jock typically includes an elastic waistband and two elastic jock straps. Each jock strap may extend from the waistband, around one of the user's legs, and connect to a pouch. Typically, the pouch connects to the waistband and holds the protective cup against the user's body (e.g., the user's groin region). The elasticity of the waistband and jock straps generally position the pouch and cup to protect the user's groin region.

Athletic support shorts, such as compression shorts, are an alternative to jocks with jock straps. Athletic support shorts may position a protective cup over a user's groin region without the use of jock straps. Some users find athletic support shorts to be preferable to jocks based on personal taste or the activity at hand. Typically, athletic support shorts include a closeable pouch that generally positions a protective cup relative to the user's groin region.

During some activities, such as the performance of sports (e.g., combat sports), existing jocks and athletic support shorts fail to provide sufficient support to secure the protective cup relative to the user's groin region. That is, known jocks and athletic support shorts do not provide sufficient support to maintain the positioning of the protective cup during certain activities. For example, in martial arts, wrestling, kickboxing, mixed martial arts or any other vigorous activity, impact to the genital area may move or push the protective cup out of position relative to the user's groin, thereby increasing the user's vulnerability to impact. When the user performs these activities, movement by the user may cause the protective cup to become dislodged or displaced from its proper positioning relative to the user's groin.

When the protective cup is dislodged from its proper positioning relative to the user's groin, the user becomes susceptible to risk of injury. Movement of the protective cup may cause the cup edge to contact the user's genitals or cause the cup edge to be in direct contact with the user's genitals rather than the appropriate surrounding area, which may cause considerable injury and pain to the user. Oftentimes a displaced protective cup may not be effective in reducing the potential for injury, and may actually increase the potential for injury to the user.

DETAILED DESCRIPTION

Figure 1:
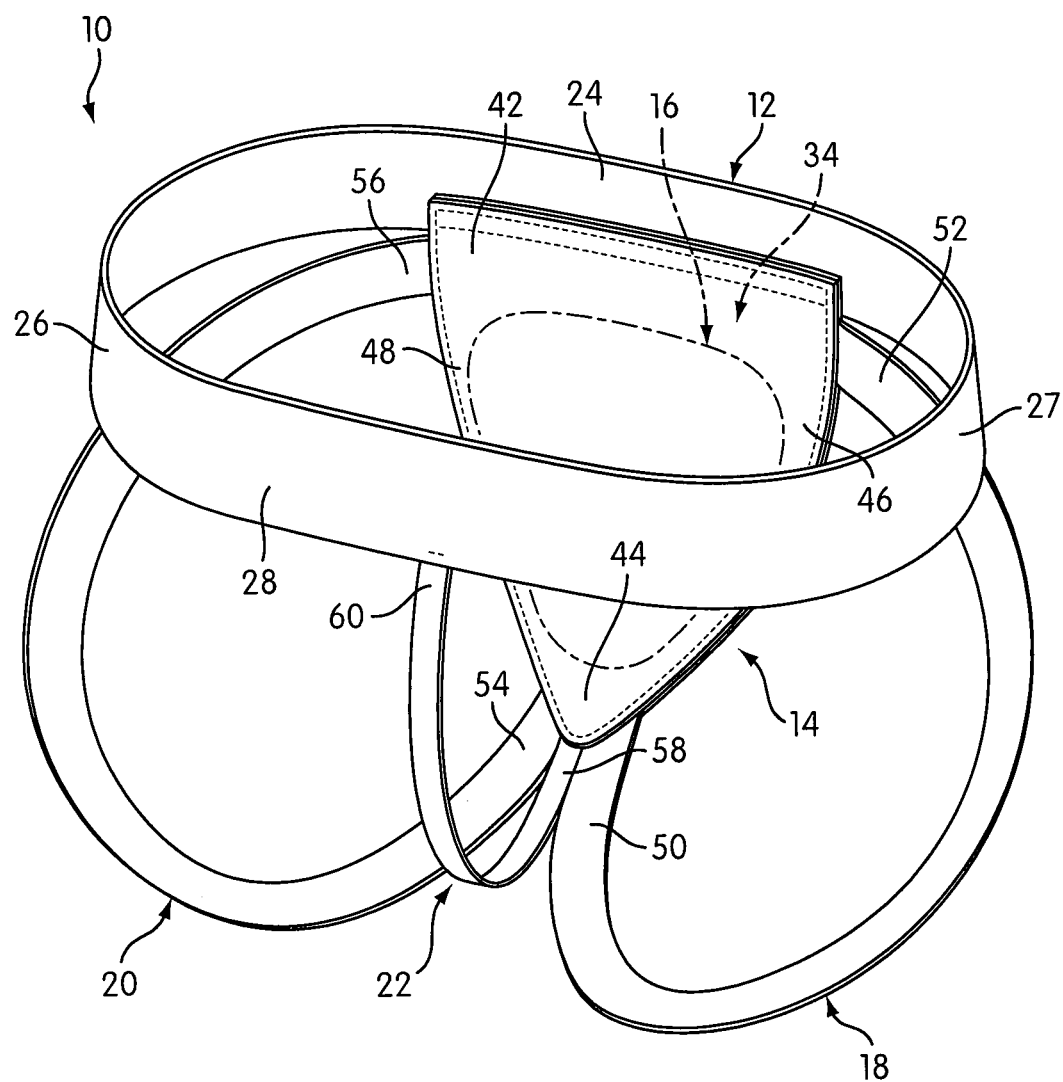
FIG. 1 illustrates a rear perspective view of an example embodiment of a garment for use with a protective cup.
Figure 2:
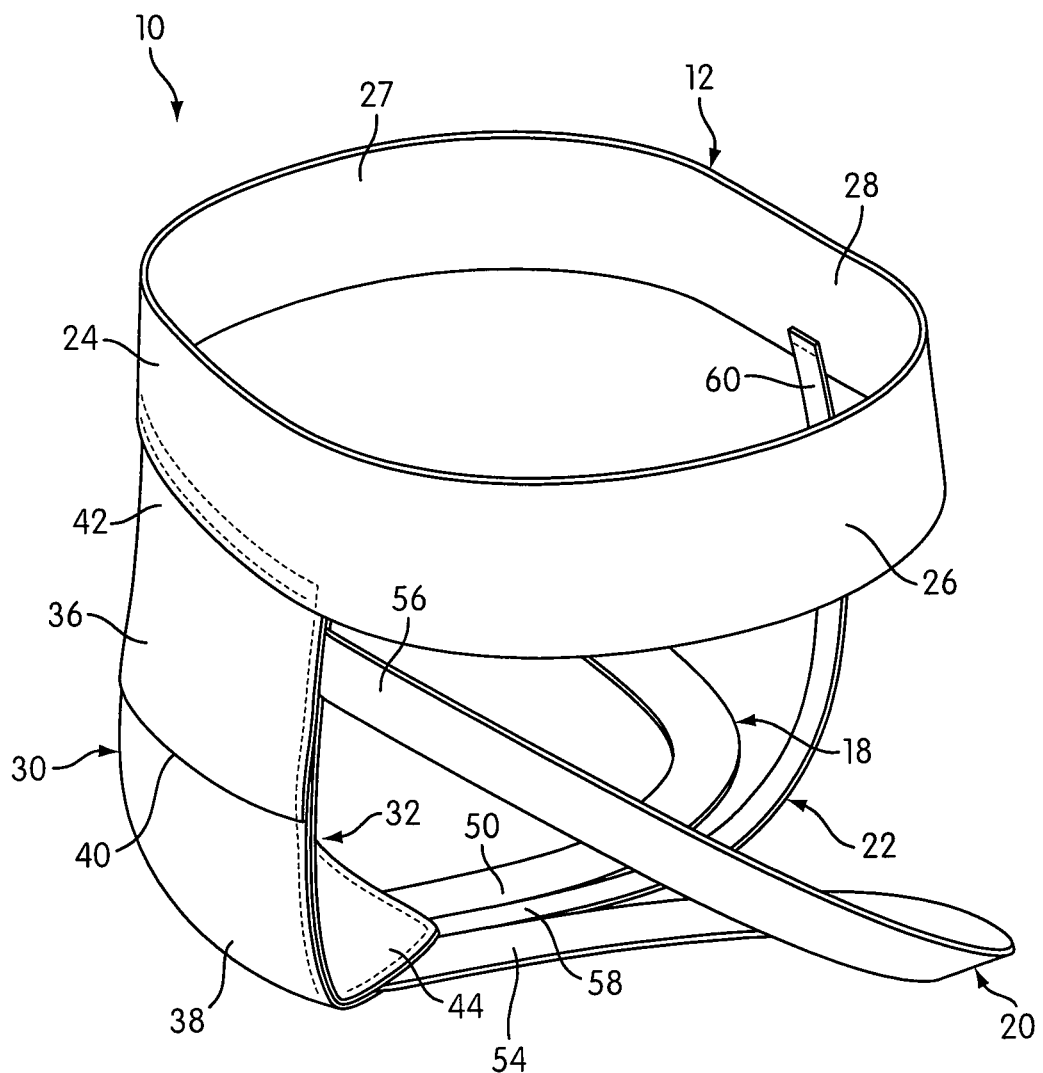
FIG. 2 illustrates a side perspective view of the example embodiment shown in FIG. 1.
Figure 3:
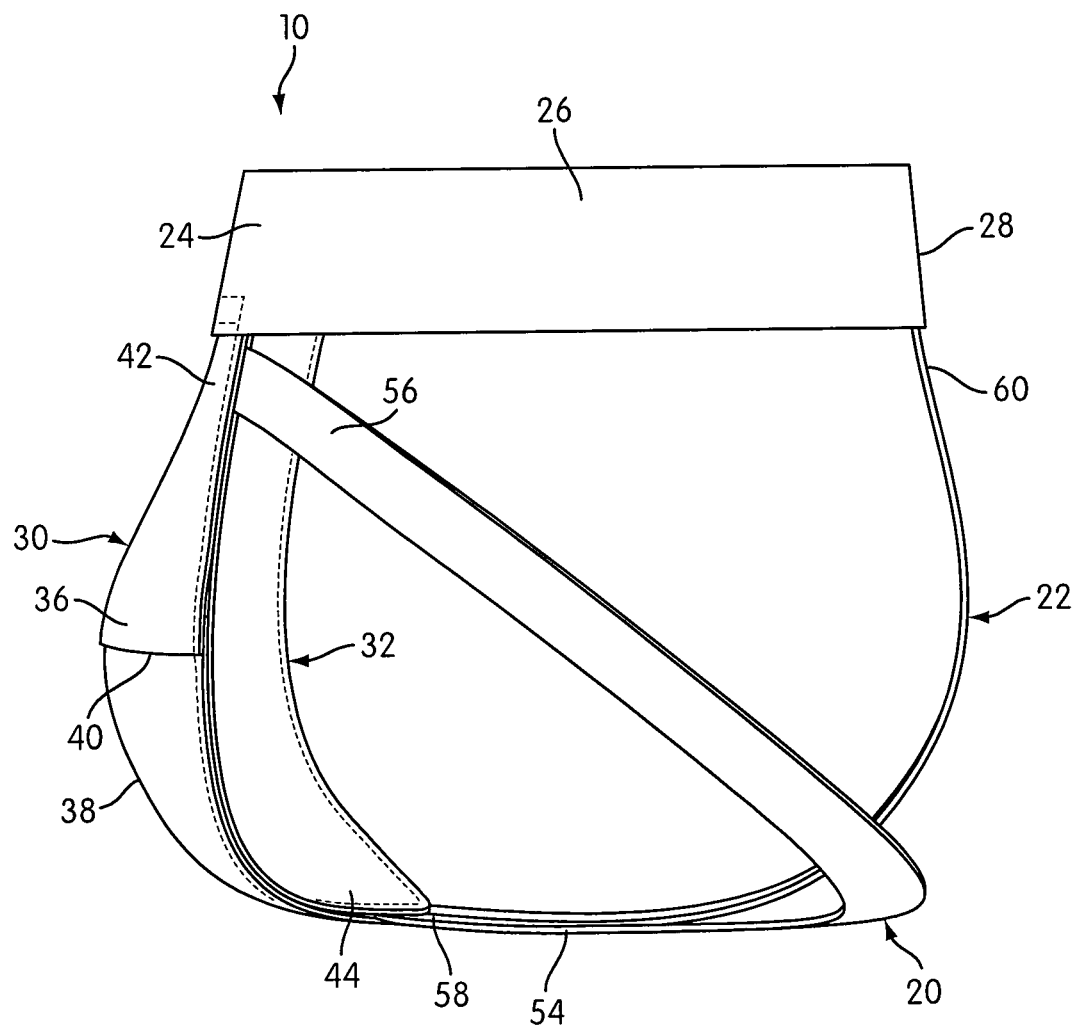
FIG. 3 illustrates a side view of the example embodiment shown in FIG. 1.

The garment of the present disclosure may be implemented in various configurations for protecting one or more areas of a user's body. In an example embodiment, the garment is configured to protect the user's groin region, such as the user's crotch area, pubic bone and genitals. The garment may also be configured to protect the user's buttocks or legs, such as the user's hips, thighs, shins or knees.

Referring now to FIGS. 1 to 3, 4A and 4B, an example embodiment of a garment 10, such as a jock or an athletic supporter, is illustrated. The garment 10 includes an annular support member 12 that encircles a user's waist and is commonly referred to as a waistband. The waistband 12 may connect or attach to a protective cup support 14. The protective cup support 14 is configured to support, hold or otherwise secure a protective cup 16 relative to a user's body. For example, the cup 16 may cover or encapsulate the user's genitals (e.g., a penis and testicles of a male user or a vulva of a female user). The garment 10 includes a first support member 18, a second support member 20 and a third support member 22 which cooperate with the waistband 12 to secure the protective cup support 14 relative to the user.

In an example embodiment, the waistband 12 has a front region 24, side regions 26, 27 and a rear region 28. The side regions 26, 27 separate the front region 24 from the rear region 28. For example, the waistband 12 may include an annular band of longitudinally elastic material which generally conforms to the waist of a user or person wearing the garment 10. The waistband 12 may include a fabric covering coextensive with and stitched to the elastic material.

In an example embodiment, the waistband 12 includes a suitably resilient or elastic material including natural fibers such as cotton, linen or wool, synthetic fibers such as polyester, spandex or nylon, or various blends of natural and synthetic fibers such as cotton and polyester or spandex and nylon. The resilient or elastic material may include a fabric having any suitable weave or pattern. It should be appreciated that the waistband 12 may be formed from a non-elastic material, such as leather, or may be used in combination with a drawstring, a belt or any other suitable closure member to maintain the garment 10 in place on the waist of the user. In an example embodiment described below in greater detail, the waistband 12 may include a fastening system having one or more closure members which maintain the garment 10 in position relative to the user's waist.

In an example embodiment, the protective cup support 14 includes a front panel 30 which may connect to a rear panel 32 by stitching or any other suitable manner. The front panel 30 and the rear panel 32 are connected to, and cooperate with, one another to form an interior space or pocket 34. The protective cup 16 may be removable from the interior space 34.

In an example embodiment, the front panel 30 may include a first portion 36 which overlaps, or otherwise cooperates with, a second portion 38 to form an aperture or slot 40 which provides access to the interior space 34. The first portion 36 may be separable from the second portion 38 by a designated amount (e.g., about one inch, about two and one-half centimeters, or any other suitable amount) to provide access to the interior space 34. As illustrated, the aperture 40 may be configured and sized to accommodate the protective cup 16 such that the protective cup 16 may be inserted through the aperture 40 and received by the interior space 34.

It should be appreciated that the aperture 40 may be formed by the rear panel 32 of the protective cup support 14, rather than the front panel 30 of the protective cup support 14. For example, the rear panel 32 may include overlapping portions which cooperate to define an aperture having access to the interior space 34. In this example, the user may access the interior space 34 (e.g., to position the protective cup 16) through the aperture on the rear panel 32 of the protective cup support 14.

In an example embodiment, the front panel 30 and the rear panel 32 may be connected together to form an upper area or portion 42, a lower area or portion 44, a first side area or portion 46 and a second side area or portion 48. The upper portion 42 connects to the front region 24 of the waistband. The upper portion 42 may attach or connect to the front region 24 of the waistband 12 by stitching, or by fabric portions integral to the waistband 12. The lower portion 44 opposes the upper portion 42 along a vertical axis. The first side portion 46 and the second side portion 48 extend between the upper portion 42 and the lower portion 44. In an example embodiment, the first and second side portions 46, 48 extend from the upper portion 42, longitudinally oppose one another, and taper or narrow at the lower portion 44.

It should be appreciated that the protective cup support 14 may directly connect to the front region 24 of the waistband 12. For example, the front region 24 of the waistband 12 may include a first end connected to at least one of the upper portion 42 and the first side portion 46 of the protective cup support 14 and a second end connected to at least one of the upper portion 42 and the second side portion 48 of the protective cup support 14. It should be also appreciated that the protective cup support 14 may directly connect to the side regions 26, 27 of the waistband 12. For example, the side region 26 of the waistband 12 may include a first end connected to at least one of the upper portion 42 and the first side portion 46 of the protective cup support 14 and the side region 27 of the waistband 12 may include a second end connected to at least one of the upper portion 42 and the second side portion 48 of the protective cup support 14.

It should be appreciated that the protective cup support 14 may be sized and shaped to substantially conform to the protective cup 16. In an example embodiment, the protective cup support 14 is sized to accommodate the protective cup 16 and to reduce the ability or likelihood of the cup 16 shifting or moving within the interior space 34 of the protective cup support 14. For example, when the protective cup 16 is received by the interior space 34, the protective cup support 14 may be configured such that the rear panel 32 supports a rear portion of the protective cup 16, the first portion 36 supports an upper, front portion of the protective cup 16, the second portion 38 supports a lower, front portion of the protective cup 16, and the waistband 12, the front panel 30 and the rear panel 32 support an upper portion of the protective cup 16.

In an example embodiment, the protective cup support 14 may include a protective cup receiving opening formed between the front panel 30 and the rear panel 32 to define the interior space 34 instead of the aperture 40 formed by overlapping portions 36, 38 of the front panel 30. The protective cup support 14 may include a closure member, such as a snap, a button, a zipper, hook and loop type fasteners or any other suitable separable fasteners, to close the protective cup receiving opening (e.g., to fasten the front panel to the rear panel).

The protective cup support 14 may include a suitably resilient or elastic material including natural fibers such as cotton, linen or wool, synthetic fibers such as polyester, spandex or nylon, or various blends of natural and synthetic fibers such as cotton and polyester or spandex and nylon. The resilient or elastic material may include a fabric having any suitable weave or pattern. The protective cup support 14 may be formed from a non-elastic material, such as leather or any other suitable non-elastic material. It should be appreciated that the protective cup support 14 could be made from any suitable material adapted to maintain a preferred or desired position of the protective cup 16 relative to the user's body when worn by that user.

In an example embodiment, the first support member 18 may connect between the lower portion 44 and the first side portion 46 of the protective cup support 14. The first support member 18 may include a first end 50 which connects to the lower portion 44 of the protective cup support 14, and a second end 52 which connects to the first side portion 46 of the protective cup support 14. The first support member 18 may be adapted to maintain the lower portion 44 and the side portion 46 of the protective cup support 14 and the protective cup 16 in a preferred position relative to the user's body. In an example embodiment, the first support member 18 stabilizes the protective cup support 14 and the protective cup 16 in lateral or side-to-side directions when the garment 10 is worn by the user.

The second support member 20 may connect between the lower portion 44 and the second side portion 48 of the protective cup support 14. The second support member 20 may include a first end 54 which connects to the lower portion 44 of the protective cup support 14, and a second end 56 which connects to the second side portion 48 of the protective cup support 14. The second support member 20 may be adapted to maintain the lower portion 44 and the side portion 48 of the protective cup support 14 and the protective cup 16 in a preferred position relative to the user's body. In an example embodiment, the second support member 20 stabilizes the protective cup support 14 and the protective cup 16 in lateral or side-to-side directions when the garment 10 is worn by the user.

The third support member 22 may connect between the lower portion 44 of the protective cup support 14 and the waistband 12. The third support member 22 may include a first end 58 which connects to the lower portion 44 of the protective cup support 14, and a second end 60 which connects to the rear portion 28 of the waistband 12. The third support member 22 may be adapted to maintain the lower portion 44 of the protective cup support 14 and the protective cup 16 in a preferred position relative to the user's body. In an example embodiment, the third support member 22 stabilizes the protective cup support 14 and the protective cup 16 in forward, backward and vertical directions when the garment 10 is worn by the user.

The first end 50 of the first support member 18, the first end 54 of the second support member 20 and the first end 58 of the third support member 22 may each connect to the lower portion 44 of the protective cup support 14 at a same location or at a substantially same location. The first end 50 of the first support member 18, the first end 54 of the second support member 20 and the first end 58 of the third support member 22 may each connect to the lower portion 44 of the protective cup support 14 at different locations (e.g., for the ends 50, 54, 58 to have a spaced relationship with one another at the lower portion 44).

It should be appreciated that the end 50 of the first support member 18, the end 54 of the second support member 20 and the ends 58, 60 of the third support member 22 may include an elastic component having sufficient elastic tension to maintain the lower portion 44 of the protective cup support 14 and the protective cup 16 in a preferred position relative to the user's body and reduce movement of the protective cup support 14 and the protective cup 16 in forward, backward, lateral and vertical directions. The ends 52, 56 of the first and second support members 18, 20 may include an elastic component having sufficient elastic tension to maintain the side portions 46, 48 of the protective cup support 14 and the protective cup 16 in a preferred position relative to the user's body and reduce movement of the protective cup support 14 and the protective cup 16 in lateral or side-to-side directions.

In an example embodiment, the first, second and third support members 18, 20, 22 may each include an elongated component or strap made from a suitably resilient or elastic material. It should be appreciated that the suitably resilient or elastic material may include natural fibers such as cotton, linen or wool, synthetic fibers such as polyester, spandex or nylon, or various blends of natural and synthetic fibers such as cotton and polyester or spandex and nylon. The resilient or elastic material may include a fabric having any suitable weave or pattern. The first, second, third support members 18, 20, 22 may each be formed from a non-elastic material, such as leather or any other suitable non-elastic material. It should also be appreciated that the first, second and third support members 18, 20, 22 may be made from any suitable material adapted to maintain the position of the protective cup 16 relative to the user's body when worn by that user.

It should be appreciated that the waistband 12, the protective cup support 14, the first support member 18, the second support member 20 and the third support member 22 may be made from any stretchable material such as elastic material or extensible material. When elongated in one or more dimensions, elastic materials may exert a force tending to move the material at least partially to its original dimensions and extensible materials may remain in the elongated dimensions.

Figure 4A:
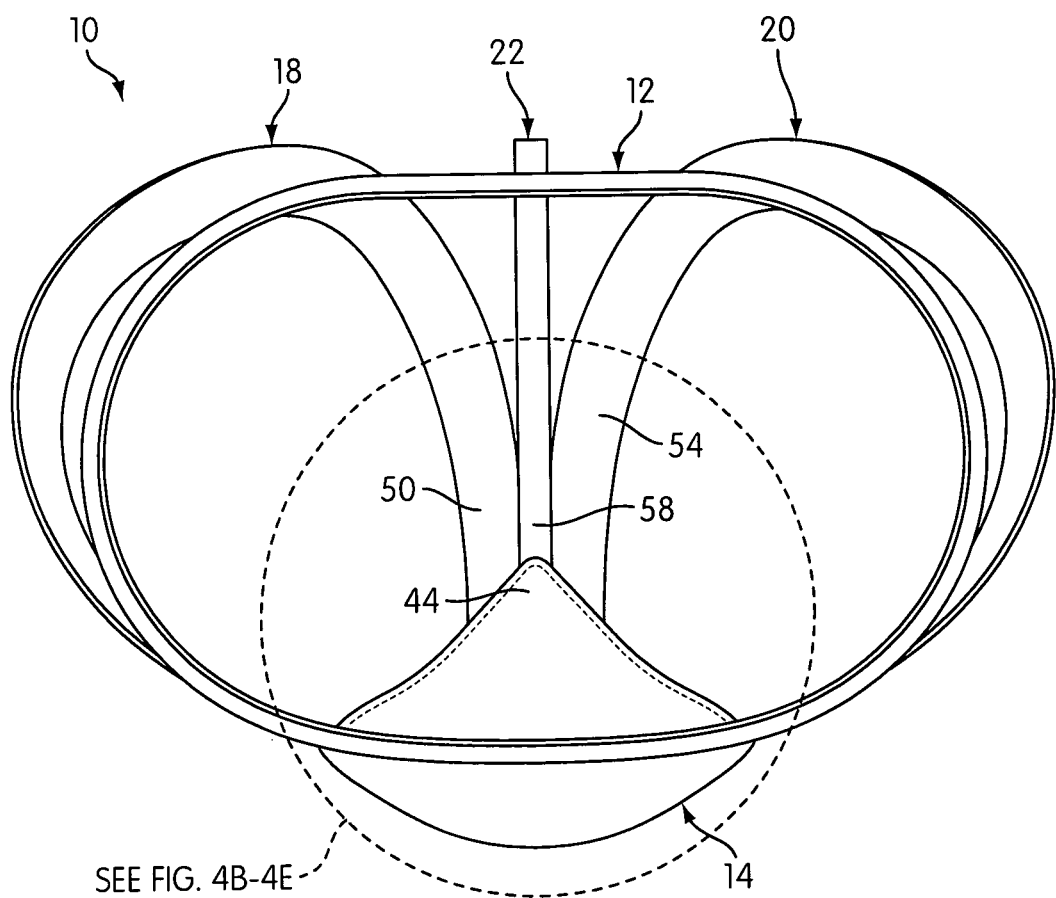
FIG. 4A illustrates a top view of the example embodiment shown in FIG. 1, wherein first, second and third support members connect to a protective cup support.
Figure 4B:
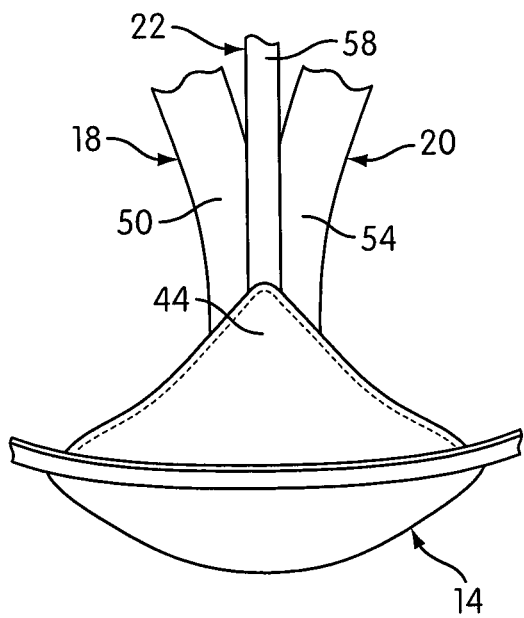
FIG. 4B illustrates an enlarged view of the example embodiment shown in FIG. 4A, wherein first, second and third support members connect to a protective cup support.

Referring now to FIG. 4B, an example embodiment of the first, second and third support members 18, 20, 22 is illustrated. The first end 50 of the first support member 18, the first end 54 of the second support member 20 and the first end 58 of the third support member 22 connects to the lower portion 44 of the protective cup support 14. The first end 58 of the third support member 22 may connect to the first end 50 of the first support member 18, the first end 54 of the second support member 20, and the lower portion 44 of the protective cup support 14 through stitching or any other suitable manner. For example, the first end 58 of the third support member 22 may connect to the an upper or top portion of the first ends 50, 54 of the first and second support members 18, 20.

Figure 4C:
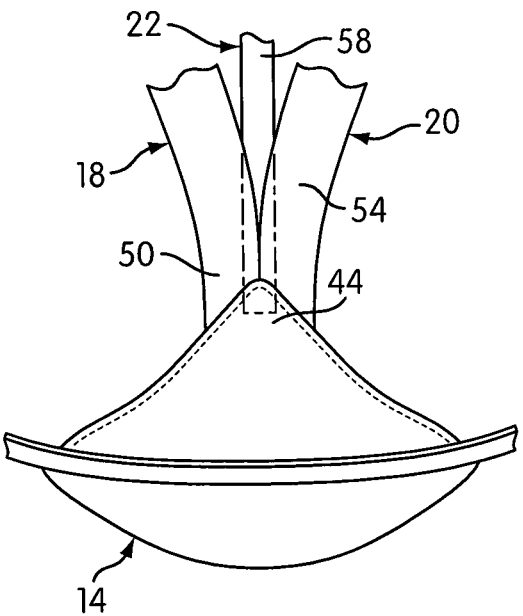
FIG. 4C illustrates an enlarged view of an example embodiment of a garment for use with a protective cup, wherein first, second and third support members connect to a protective cup support.

Referring now to FIG. 4C, an example embodiment of the first, second and third support members 18, 20, 22 is illustrated. The first end 50 of the first support member 18, the first end 54 of the second support member 20 and the first end 58 of the third support member 22 connects to the lower portion 44 of the protective cup support 14. The first end 58 of the third support member 22 may connect to the first end 50 of the first support member 18, the first end 54 of the second support member 20, and the lower portion 44 of the protective cup support 14 through stitching or any other suitable manner. For example, the first end 58 of the third support member 22 may connect to the a lower or bottom portion of the first ends 50, 54 of the first and second support members 18, 20.

Figure 4D:
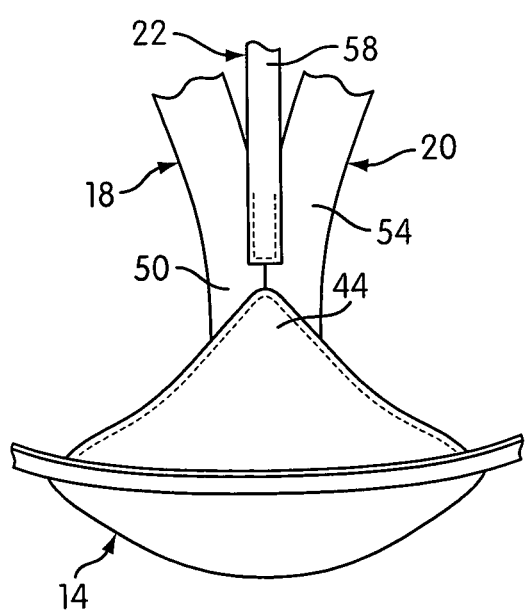
FIG. 4D illustrates an enlarged view of an example embodiment of a garment for use with a protective cup, wherein first, second and third support members connect to a protective cup support.

Referring now to FIG. 4D, an example embodiment of the first, second and third support members 18, 20, 22 is illustrated. The first end 50 of the first support member 18 and the first end 54 of the second support member 20 connects to the lower portion 44 of the protective cup support 14. The first end 58 of the third support member 22 may connect to the first end 50 of the first support member 18, the first end 54 of the second support member 20, or both through stitching or any other suitable manner. The first end 58 of the third support member 22 may connect to any suitable portion of the first ends 50, 54 of the first and second support members 18, 20. For example, the first end 58 of the third support member 22 may connect to a top side of the first end 50 of the first support member 18 and the first end 54 of the second support member 20.

Figure 4E:
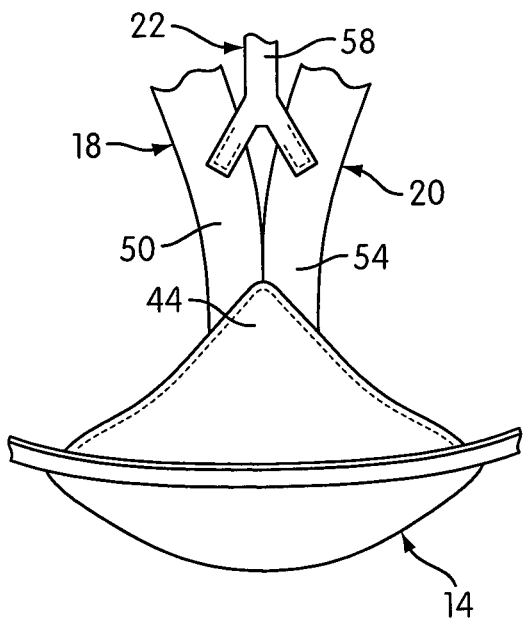
FIG. 4E illustrates an enlarged view of an example embodiment of a garment for use with a protective cup, wherein first, second and third support members connect to a protective cup support.

Referring now to FIG. 4E, an example embodiment of the first, second and third support members 18, 20, 22 is illustrated. The first end 50 of the first support member 18 and the first end 54 of the second support member 20 connects to the lower portion 44 of the protective cup support 14. The first end 58 of the third support member 22 may connect to any suitable portion of the first ends 50, 54, of the first and second support members 18, 20. For example, the first end 58 of the third support member 22 may be "Y" shaped. The first end 58 of the third support member 22 may have a first portion which connects to the first end 50 of the first support member 18, and a second portion which connects to the first end 54 of the second support member 20.

It should be appreciated that the first end 58 of the third support member 22 may directly or indirectly connect to the lower portion 44 of the protective cup support 14 via at least one of (i) the first end 50 of the first support member 18, (ii) the first end 54 of the second support member 20, and (iii) the first end 50 of the first support member 18 and the first end 54 of the second support member 20.

The first, second or third support members 18, 20, 22 may be shaped, made from certain materials, or connected to various portions of the waistband 12 or the protective cup support 14 to increase the user's comfort while wearing the garment 10. For example, the third support member 22 may have a width that is greater than a width of the first or second support members 18, 20. In an example embodiment, the second end 60 of the third support member 22 may have a width which is greater than the first end 58 of the third support member 22. The increased width of the third support member 22, or the increased width of the first end 58 or the second end 60 of the third support member 22 may increase the user's comfort while wearing the garment 10.

Figure 5A:
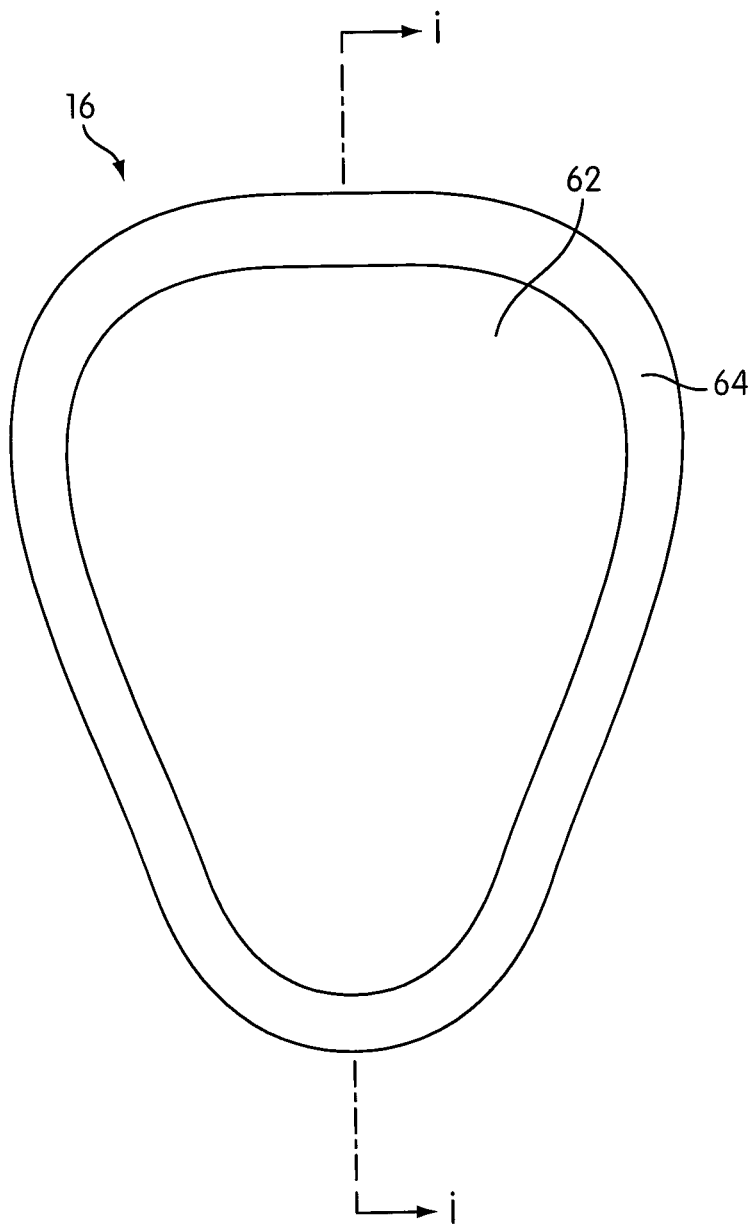
FIG. 5A illustrates a front view of an example embodiment of a protective cup.
Figure 5B:
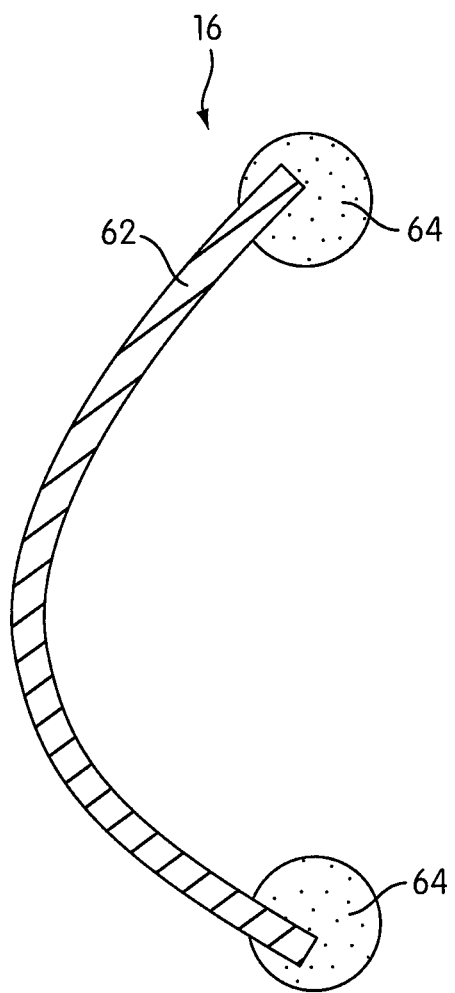
FIG. 5B illustrates a cross-sectional view taken along line i-i of the example embodiment shown in FIG. 5A.

Referring now to FIGS. 5A and 5B, an example embodiment of the protective cup 16 is illustrated. The protective cup 16 includes a substantially convex protective cup body 62 shaped and sized to protect a user's groin. In an example embodiment, a pad or padded portion 64 of a suitable thickness may extend along all or part of an edge or edge surface of the body 62. The padded portion 64 may be bonded, adhered or otherwise connected to the edge of the body 62 in any suitable manner. The thickness of the padded portion 64 creates separation between the body 62 and the user's groin, which may distribute the force of an impact or pressure over a suitably large area of the user's body wherein the cup 16 is positioned. This may prevent the body 62 of the cup 16 from digging in, bruising or chaffing the user's body. In an example embodiment, the padded portion 64 may be shaped and have an appropriate thickness to reduce irritation and injury to the user's groin or legs, where the padded portion 64 is typically seated.

Figure 6A:
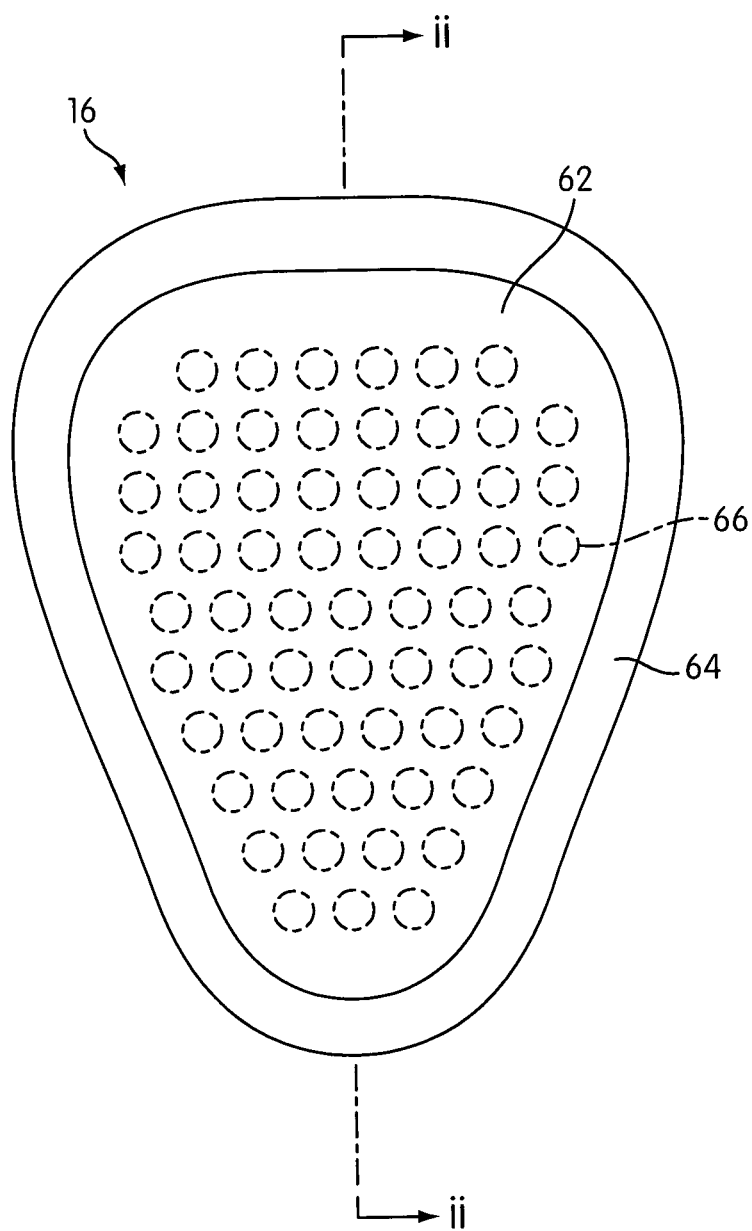
FIG. 6A illustrates a front view of an example embodiment of a protective cup.
Figure 6B:
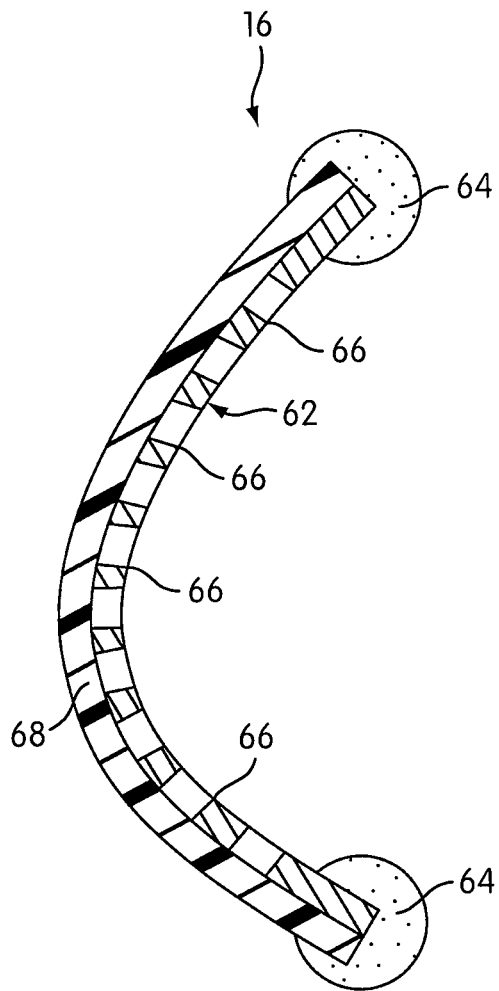
FIG. 6B illustrates a cross-sectional view taken along line ii-ii of the example embodiment shown in FIG. 6A.
Figure 6C:
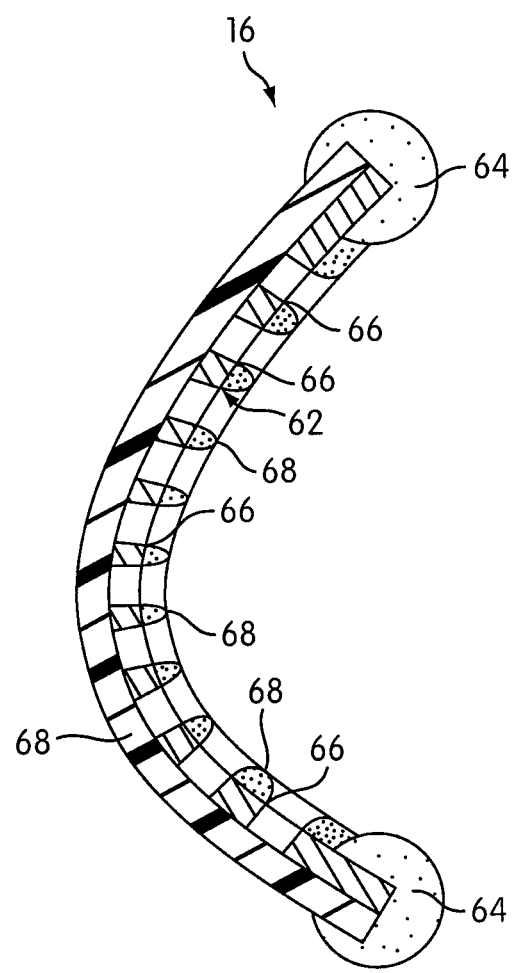
FIG. 6C illustrates a cross-sectional view taken along line ii-ii of the example embodiment shown in FIG. 6A.

In an example embodiment, as illustrated in FIGS. 6A, 6B and 6C, the protective cup 16 includes a plurality of openings 66 formed through the body 62. The openings 66 may be sized, shaped or positioned to reduce the weight of the protective cup 16, increase ventilation through the protective cup 16, increase the structural strength of the protective cup, or any suitable combination thereof. In an example embodiment, the protective cup 16 may include a pad or padded layer 68 which covers the body 62 of the protective cup 16. The padded layer 68 may cover or overlay the body 62 and/or the padded portion 64 of the protective cup 16. The padded layer 68 may be bonded, adhered or otherwise connected to the body 62 in any suitable manner. The padded layer 68 may be formed integral with or may be coupled to the body 62, the padded portion 64, or both. For example, the padded portion 64 and the padded layer 68 may be integrally formed, such as by injection molding.

It should be appreciated that one, two or more padded layers 68 may cover the body 62. For example, one or more padded layers 68 may each cover an outer surface and/or an inner surface of the body 62 of the protective cup 16. In an example embodiment, as illustrated in FIG. 6B, the protective cup 16 includes at least one padded layer 68 which covers the exterior surface or portion of the body 62 of the protective cup 16. Openings may be formed in the padded layer 68 to align with the openings 66 formed through the body 62. In an example embodiment, as illustrated in FIG. 6C, the protective cup 16 includes at least one padded layer 68 which covers an outer surface or portion of the body 62 of the protective cup 16 and at least one padded layer 68 which covers an inner surface or portion of the body 62 of the protective cup 16. Openings may be formed in the padded layers 68 to align with the openings 66 formed through the body 62.

In an example embodiment, the padded layer 68 may cover or substantially cover an inner surface or portion of the body 62 of the protective cup 16. Certain portions or areas of the padded layer 68 may be configured to extend through one or more of the openings 66 formed through the body 62 so that the padded layer 68 interfaces with both the inner surface and the outer surface of the body 62. For example, the padded layer 68 may include at least one cell, rib, bump or protrusion that extends into or through at least one of the openings 66 (e.g., from the inner surface of the protective cup to or through the outer surface of the protective cup). The cells, ribs, bumps or protrusions may be filled with a solid, a liquid, a gas or a gel to absorb, disperse or reduce the amount of force or speed of an impact. In an example embodiment, the padded layer 68 may include one or more cells, ribs, bumps or protrusions configured to secure the padded layer 68 to the outer surface of the body 62 of the protective cup 16. For example, the cells, ribs, bumps or protrusions may include a flanged end that is configured to compress or deform when inserted through one of the openings 66 in the cup body 62 and expand to its original form after passing through that opening 66. By expanding to its original form, the flanged end of the cell, rib, bump or protrusion may secure the padded layer 68 to the inner and outer surfaces of the body 62 of the protective cup 16. It should be appreciated that the padded layer 68 may be removably attached to the body 62 for cleaning or replacement.

The padded portion 64 and/or the padded layer 68 may include any suitable perforated or non-perforated material which absorbs, disperses or reduces an amount of force exerted thereon. In an example embodiment, the padded portion 64 and/or the padded layer 68 may include any suitable polymer which is suitable to absorb, disperse or reduce the amount of force or speed of an impact. The padded portion 64 and/or the padded layer 68 may include a shock absorbing polymer, a vibration dampening polymer, a viscoelastic polymer or a visco polymer, such as the polymers manufactured by Action Products, Inc. of Hagerstown, Md. In an example embodiment, the padded portion 64 and/or the padded layer 68 may include one or more cells, ribs, bumps or protrusions filled with a solid, a liquid, a gas or a gel to absorb, disperse or reduce the amount of force or speed of an impact. In an example embodiment, the padded portion 64 and/or the padded layer 68 may include rubber or foam, which may act as a crumple zone to absorb, disperse, or reduce the amount of force or speed of an impact. For example, the padded portion 64 and/or the padded layer 68 may be any suitable foam, such as an ethylene vinyl acetate (EVA) foam or a closed cell foam (e.g., polyethylene foam, polystyrene foam, or polychloroprene foam). In an example embodiment, the padded portion 64 and/or the padded layer 68 may be a panel of perforated or non-perforated thermoplastic material having a honeycomb core and a plurality of sheets bonded to the honeycomb core. The honeycomb core may have shock dampening characteristics to absorb, disperse, or reduce the amount of force or speed of an impact. One example of a suitable honeycomb structure is manufactured by Supracor, Inc. of San Jose, Calif.

It should be appreciated that the protective cup 16 may be sized and shaped similar to a traditional cup, a banana cup, or any other suitable protective cup. The protective cup 16 may also be sized and shaped based on the wearer's sex (i.e., male, or female). In an example embodiment, the protective cup 16 may be a "soft" cup which may readily conform to the general shape and contours of the wearer's body (e.g., made from a pliable material, such as foam, rubber or plastic), or a "hard" cup which may not readily conform to the general shape and contours of the wearer's body (e.g., made from a rigid material such synthetic or composite materials, such as plastics, resins or carbon fiber, or metals, such as steel, aluminum alloy). The protective cup 16 may be sized and shaped based on the wearer's age (e.g., adult or youth). The protective cup 16 may be sized and shaped based on a specific activity for which the protective cup 16 will be used (e.g., a hockey cup or a boxing cup).

In an example embodiment, each of the first, second and third support members 18, 20, 22 may have at least one end directly connected to the protective cup 16. The first ends 50, 54, 58 of the first, second and third support members 18, 20, 22 each may connect to a lower portion of the protective cup 16. The second end 52 of the first support member 18 may connect to a first side portion of the protective cup 16. The second end 56 of the second support member 20 may connect to a second side portion of the protective cup 16.

In an example embodiment, the first ends 50, 54, 58 may connect to the protective cup 16 through the same opening 66 or through different openings 66 in the body 62 of the protective cup 16. The second ends 52, 56 of the first and second support members 18, 20 may connect to the protective cup 16 through openings 66 formed in, or adjacent to, the side portions of the protective cup 16. The second end 60 of the third support member 22 may connect to the rear portion 28 of the waistband 12. In an example embodiment, the second end 60 of the third support member 22 may connect to the waistband 12 by stitching or any other suitable manner.

In an example embodiment, a genital positioner may be connected to, or used in conjunction with, the garment 10. The genital positioner may be a pocket, a pouch, a sack, a sheath, a sleeve or any other suitable holder that is configured to secure and locate the user's genitals in a preferred position relative to the protective cup support 14 and the protective cup 16. The genital positioner may include a drawstring or any other suitable closure member to secure the user's genitals within the genital positioner. In an example embodiment, the genital positioner may be connected to the first support member 18, the second support member 20, the protective cup support 14, the protective cup 16, or any combination thereof to locate the user's genitals in the preferred position relative to the protective cup support 14 and the protective cup 16 when the garment 10 is worn by the user. The genital positioner may be configured to minimize or reduce the possibility of the user's genitals contacting the protective cup 16. For example, after an impact to the user's groin region, the genital positioner may prevent or reduce the possibility of the user's genitals from contacting the protective cup 16. In an example embodiment, the genital positioner may include a padded portion, such as the padded layer 68 described above. If the user's genitals were to contact the protective cup 16 after an impact to the user's groin, the padded layer of the genital positioner may reduce the force or speed at which the user's genitals contact the protective cup 16.

Figure 7:
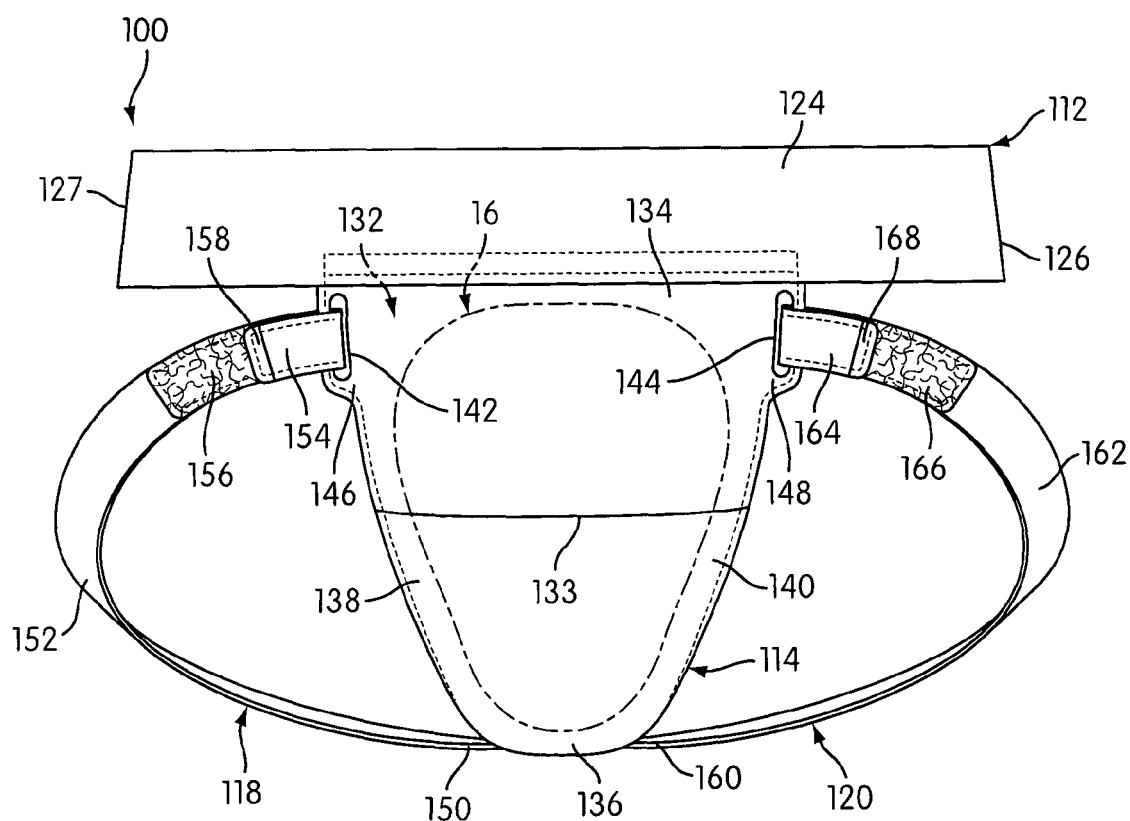
FIG. 7 illustrates a front view of an example embodiment of a garment for use with a protective cup, wherein first, second and third support members adjustably connect to a protective cup support.
Figure 8:
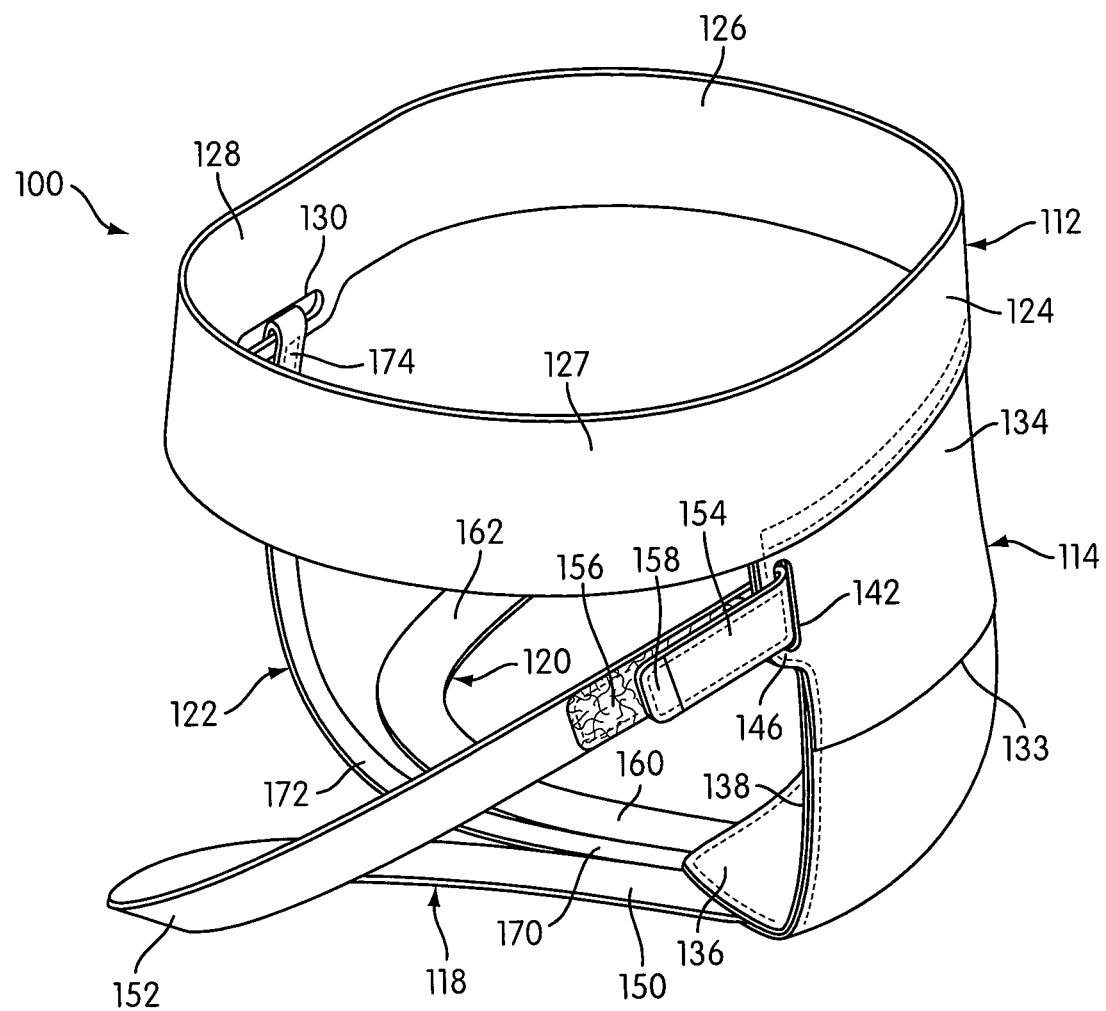
FIG. 8 illustrates a side perspective view of the example embodiment shown in FIG. 7.
Figure 9:
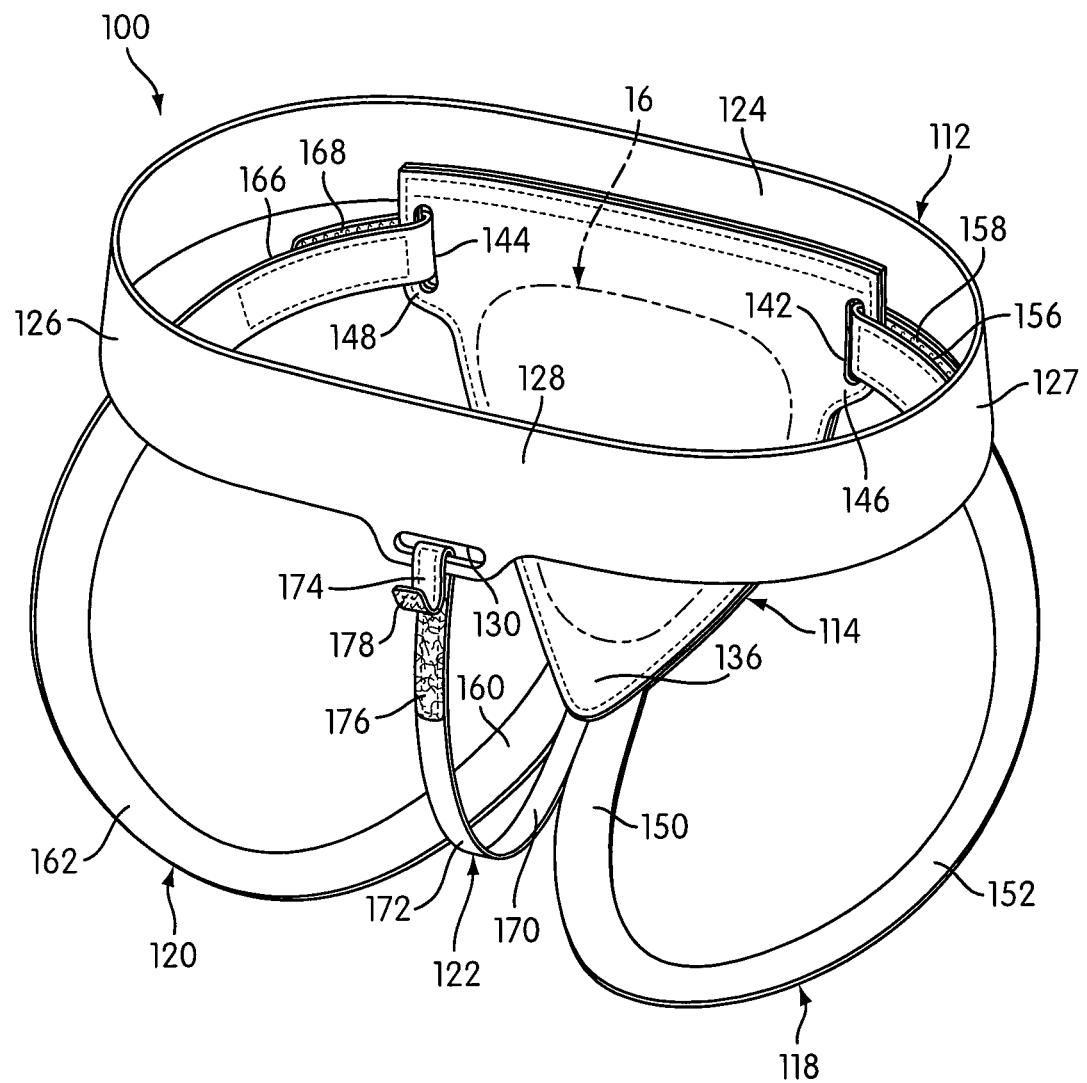
FIG. 9 illustrates a rear perspective view of the example embodiment shown in FIG. 7.

Referring now to FIGS. 7 to 9, an example embodiment of a garment 100, such as a jock or an athletic supporter, is illustrated. The garment 100 includes an annular support member 112 that encircles a user's waist and is commonly referred to as a waistband. The waistband 112 may connect or attach to a protective cup support 114. The protective cup support 114 is configured to support, hold or otherwise secure a protective cup, such as the protective cup 16 described above, relative to a user's body. The garment 100 includes a first support member 118, a second support member 120 and a third support member 122 which cooperate with the waistband 112 to secure the protective cup support 114 relative to the user.

In an example embodiment, the waistband 112 may include an annular band of longitudinally elastic material which generally conforms to the waist of a user or person wearing the garment 100. The waistband 112 may include a fabric covering coextensive with and stitched to the elastic material. The waistband 112 may have a front region 124, side regions 126, 127 and a rear region 128. The side regions 126, 127 separate the front region 124 from the rear region 128. The rear region 128 of the waistband 112 may include a support member receiving aperture or opening 130, which may be configured to receive the third support member 122 therethrough, as described below in greater detail.

In an example embodiment, the protective cup support 114 may define an interior space 132, which may be substantially similar to the interior space 34 described above. For example, first and second portions of the protective cup support 114 may be separable from one another to form an aperture or slot 133 which provides access to the interior space 132. The aperture 133 may have any suitable configuration or size to accommodate the protective cup, such as the protective cup 16 described above. The protective cup may be inserted through the aperture 133 and received by the interior space 132. The protective cup support 114 may include an upper area or portion 134, a lower area or portion 136, a first side area or portion 138 and a second side area or portion 140.

The upper portion 134 may connect to the front region 124 of the waistband by stitching, or by fabric portions integral to the waistband 112. The lower portion 136 opposes the upper portion 134 along a vertical axis. The first side portion 138 and the second side portion 140 extend between the upper portion 134 and the lower portion 136. In an example embodiment, the first and second side portions 138, 140 extend from the upper portion 134, longitudinally oppose one another, and taper or narrow at the lower portion 136.

It should be appreciated that the protective cup support 114 may be sized and shaped to substantially conform to the protective cup. In an example embodiment, the protective cup support 114 is sized to accommodate the protective cup and to reduce the ability or likelihood of the cup shifting or moving within the interior space 132 of the protective cup support 114. For example, when the protective cup is received by the interior space 132, the protective cup support 114 is configured such that the upper portion 134 may support an upper portion of the protective cup, the lower portion 136 may support a lower portion of the protective cup, and the side portions 138, 140 may support respective side portions of the protective cup.

The side portions 138, 140 of the protective cup support 114 may include apertures or openings which receive the first and second support members 118, 120. The first side portion 138 may include a support member receiving aperture or opening 142, which may be configured to receive the first support member 118 therethrough. The second side portion 140 may include a support member receiving aperture or opening 144, which may be configured to receive the second support member 120 therethrough.

The support member receiving apertures 142, 144 may be defined by respective flanges 146, 148 which extend from the side portions 138, 140. The flanges 146, 148 may include upper portions which connect to the front region 124 of the waistband by stitching, or by fabric portions integral to the waistband 112. In an example embodiment, the flanges 146, 148 and the upper portion 134 may connect to the waistband 112 to stabilize the protective cup support 114 and the protective cup in a vertical direction.

In an example embodiment, the first support member 118 connects between the lower portion 136 and the first side portion 138 of the protective cup support 114. The first support member 118 includes a first end 150, a body 152 and a second end 154. The body 152 may extend between the first end 150 and the second end 154. The body 152 may have a first fastener 156 stitched to, connected to, or otherwise formed integral with the body 152. The second end 154 may have a second fastener 158 stitched to, connected to, or otherwise formed integral with the second end 154.

The first end 150 may connect to the lower portion 136 of the protective cup support 114. The second end 154 may connect to the side portion 138 by extending through the support member receiving aperture 142 formed in the side portion 138. The second fastener 158 may cooperate with the first fastener 156 to adjustably connect the second end 154 to the side portion 138 of the protective cup support 114. The second end 154 may be moved to different positions along the body 152, and secured thereto by the fasteners 156, 158, to change or adjust the position and fit of the protective cup support 114 and the protective cup relative to the user's body. The first support member 118 is adapted to maintain the lower portion 134 and the side portion 138 of the protective cup support 114 and the protective cup in a preferred position relative to the user's body. In an example embodiment, the first support member 118 stabilizes the protective cup support 114 and the protective cup in lateral or side-to-side directions when the garment 100 is worn by the user.

In an example embodiment, the second support member 120 connects between the lower portion 136 and the second side portion 140 of the protective cup support 114. The second support member 120 includes a first end 160, a body 162 and a second end 164. The body 162 may extend between the first end 160 and the second end 164. The body 162 may have a first fastener 166 stitched to, connected to, or otherwise formed integral with the body 162. The second end 164 may have a second fastener 168 stitched to, connected to, or otherwise formed integral with the second end 164.

The first end 160 may connect to the lower portion 136 of the protective cup support 114. The second end 164 may connect to the side portion 140 by extending through the support member receiving aperture 144 formed in the side portion 140. The second fastener 168 may cooperate with the first fastener 166 to adjustably connect the second end 164 to the side portion 140 of the protective cup support 114. The second end 164 may be moved to different positions along the body 162, and secured thereto by the fasteners 166, 168, to change or adjust the position and fit of the protective cup support 114 and the protective cup relative to the user's body. The second support member 120 is adapted to maintain the lower portion 136 and the side portion 140 of the protective cup support 114 and the protective cup in a preferred position relative to the user's body. In an example embodiment, the second support member 120 stabilizes the protective cup support 114 and the protective cup in lateral or side-to-side directions when the garment 100 is worn by the user.

The third support member 122 connects between the lower portion 136 of the protective cup support 114 and the waistband 112. The third support member 122 includes a first end 170, a body 172 and a second end 174. The body 172 may extend between the first end 170 and the second end 174. The body 172 may have a first fastener 176 stitched to, connected to, or otherwise formed integral with the body 172. The second end 174 may have a second fastener 178 stitched to, connected to, or otherwise formed integral with the second end 174.

The first end 170 may connect to the lower portion 136 of the protective cup support 114. The second end 174 may connect to the rear portion 128 of the waistband 112 by extending through the support member receiving aperture 130 formed in the rear portion 128. The second end 174 may be moved to different positions along the body 172, and secured thereto by the fasteners 176, 178, to change or adjust the position and fit of the protective cup support 114 and the protective cup relative to the user's body. The third support member 122 maintains the lower portion 136 of the protective cup support 114 and the protective cup in a preferred position relative to the user's body. In an example embodiment, the third support member 122 stabilizes the protective cup support 114 and the protective cup in forward, backward and vertical directions when the garment 100 is worn by the user.

In an example embodiment, the lower portion 134 of the protective cup support 114 may include one or more flanges which define a support member receiving aperture. The support member receiving aperture defined by each flange may be configured to receive at least one of the first, second and third support members 118, 120, 122 therethrough. For example, the first, second and third support members 118, 120, 122 may extend through the same aperture defined by one flange, or may extend through different apertures defined by different flanges. The first ends 150, 160 and 170 of the first, second, and third support members 118, 120, 122 may adjustably connect to the lower portion 134 of the protective cup support 114 in a similar manner as described above with respect to second ends 154, 164 adjustably connecting to the side portions 138, 140 of the protective cup support 114.

In an example embodiment, the fasteners 156, 158, 166, 168, 176, 178 may be stitched to, connected to, or otherwise formed integral with the second ends 154, 164, 174 of the first, second and third support members 118, 120, 122. For example, the second end 154 may include the fasteners 156, 158 so that the second end 154 extends through the aperture 142 and adjustably connects to itself via the fasteners 156, 158. The fasteners 156, 158, 166, 168, 176, 178 may be any variety of suitable fastener, such as hook and loop type fasteners. It should be appreciated that the fasteners 156, 158, 166, 168, 176, 178 may be sized and positioned to enable adjustability of the first, second and third support members 118, 120, 122 to different adjustable positions.

The end 150 of the first support member 118, the end 160 of the second support member 120 and the end 160 of the third support member 122 may be adjustable to different positions to maintain the lower portion 136 of the protective cup support 114 and the protective cup in a preferred position and reduce movement of the support 114 and the cup in forward, backward, lateral and vertical directions. The ends 154, 164 of the first and second support members 118, 120 may be adjustable to different positions to maintain the side portions 138, 140 of the protective cup support 114 and the protective cup in a preferred position and reduce movement of the support 114 and the cup in lateral or side-to-side directions.

In an example embodiment, the first, second and third support members 118, 120, 122 may each include an elongated component or strap made from a suitably resilient or elastic material. It should be appreciated that the suitably resilient or elastic material may include natural fibers such as cotton, linen or wool, synthetic fibers such as polyester, spandex or nylon, or various blends of natural and synthetic fibers such as cotton and polyester or spandex and nylon. The resilient or elastic material may include a fabric having any suitable weave or pattern. The first, second, third support members 118, 120, 122 may each be formed from a non-elastic material, such as leather or any other suitable extensible material. It should also be appreciated that the first, second and third support members 118, 120, 122 may be made from any suitable material adapted to maintain the position of the protective cup relative to the user's body when worn by that user.

It should be appreciated that the waistband 112, the protective cup support 114, the first support member 118, the second support member 120 and the third support member 122 may be made from any stretchable material such as elastic material or extensible material. When elongated in one or more dimensions, elastic materials may exert a force tending to move the material at least partially to its original dimensions and extensible materials may remain in the elongated dimensions.

Figure 10:
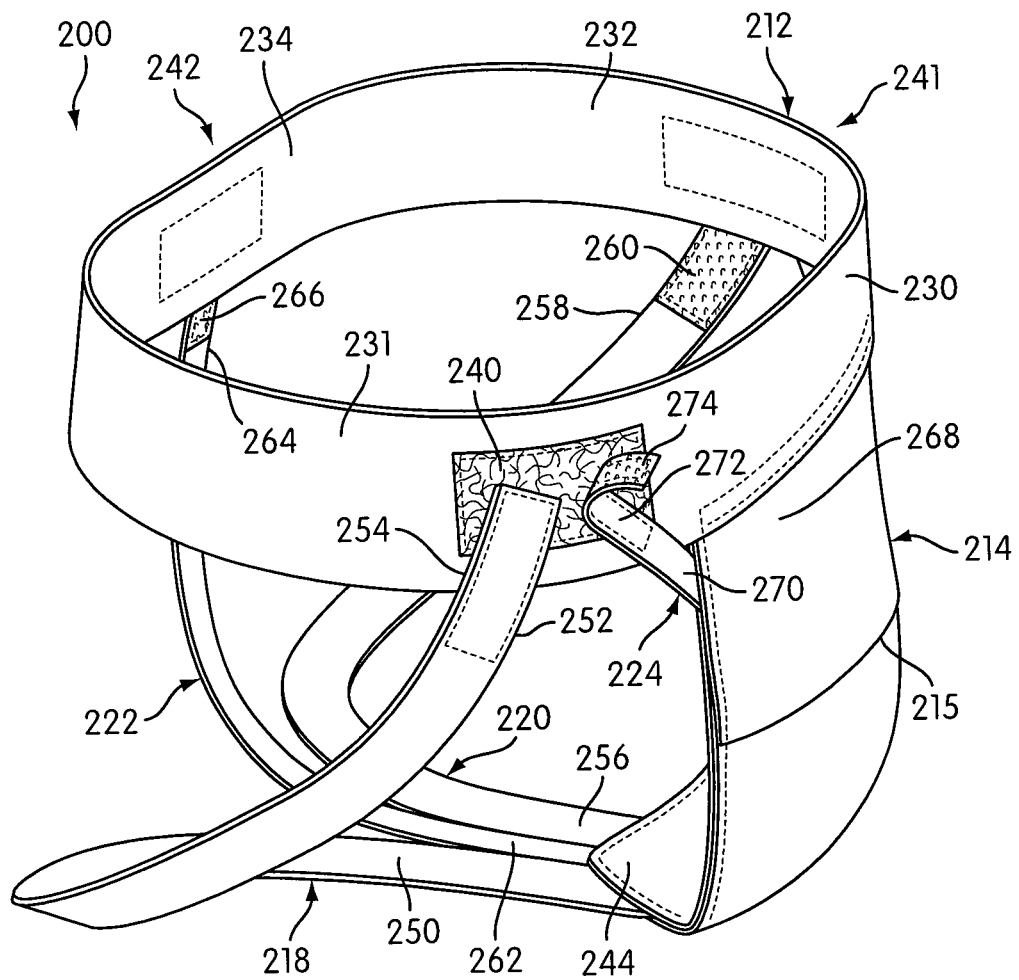
FIG. 10 illustrates a side perspective view of an example embodiment of a garment for use with a protective cup.
Figure 11:
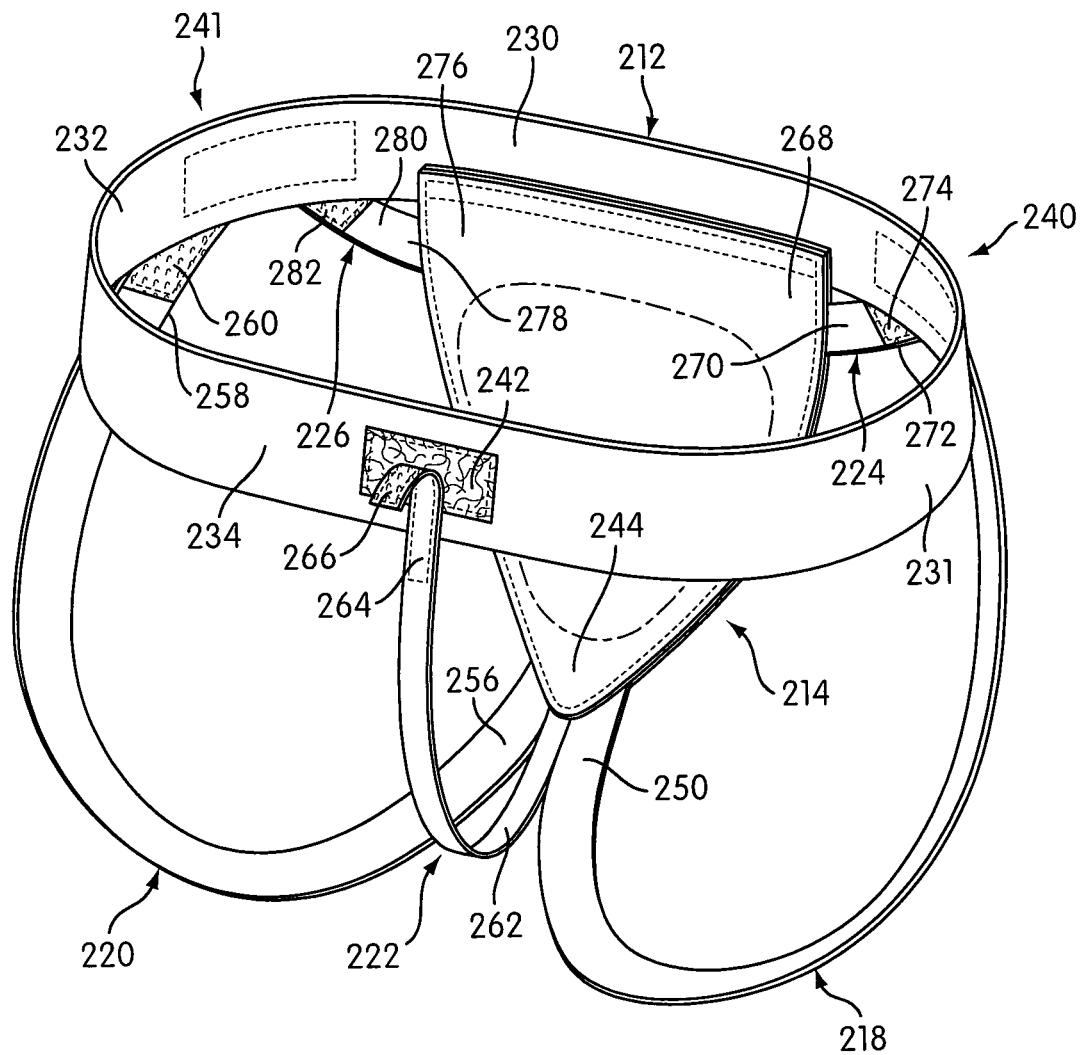
FIG. 11 illustrates a rear perspective view of the example embodiment shown in FIG. 10.

Referring now to FIGS. 10 and 11, an example embodiment of a garment 200, such as a jock or an athletic supporter, is illustrated. The garment 200 includes an annular support member 212, which is commonly referred to as a waistband. The waistband 212 may connect or attach to a protective cup support 214. The protective cup support 214 is configured to support, hold or otherwise secure a protective cup, such as the protective cup 16 described above, relative to a user's body, specifically that user's groin region. For example, first and second portions of the protective cup support 214 may be separable from one another to form an aperture or slot 215 which provides access to an interior space thereof. The aperture 215 may have any suitable configuration or size to accommodate the protective cup when the protective cup is inserted through the aperture 215 and received by the interior space of the protective cup support 214.

In an example embodiment, the waistband 212 has a front region 230, side regions 232, 233 and a rear region 234. The side regions 232, 233 separate the front region 230 from the rear region 234. The waistband 212 may include an annular band of longitudinally elastic material which generally conforms to the waist of a user or person wearing the garment 200. The waistband 200 may also include a fabric covering that is coextensive with and stitched to the elastic material.

The side regions 231, 232 may each include a side fastener 240, 241 and the rear region 234 may include a rear fastener 242. The fasteners 240, 241 and 242 are positioned along the exterior of the waistband 212 such that one or more of the support members 218, 220, 222, 224 and 226 may be adjustably connected to each fastener 240, 241 and 242.

In an example embodiment, the garment 200 includes a first support member 218, a second support member 220, a third support member 222, a fourth support member 224, and a fifth support member 226 which cooperate to secure the protective cup support 214 relative to the waistband 212 and to the user.

In an example embodiment of garment 200, the first support member 218 connects between a lower portion 244 of the protective cup support 214 and the side fastener 240. The first support member 218 includes a first end 250 which connects to the lower portion 244 of the protective cup support 14, and a second end 252 which adjustably connects to the side fastener 240 of the waistband 212. The second end 252 of the first support member 218 may include a fastener 254 which cooperates with the side fastener 240 to adjustably secure the first support member 218 to the waistband 212. The second end 252 of the first support member 218 may be moved to different positions relative to the waistband 212, wherein at each position, the fastener 254 engages the side fastener 240 to adjustably tighten the protective cup support 214 relative to the user's body.

The second support member 220 connects between the lower portion 244 of the protective cup support 214 and the side fasteners 241. The second support member 220 includes a first end 256 which connects to the lower portion 244 of the protective cup support 14, and a second end 258 which adjustably connects to the side fastener 241 of the waistband 212. The second end 258 of the second support member 220 may include a fastener 260 which cooperates with the side fastener 241 to adjustably secure the second support member 220 to the waistband 212. The second end 258 of the second support member 220 may be moved to different positions relative to the waistband 212, wherein at each position, the fastener 260 engages the side fastener 241 to adjustably tighten the protective cup support 214 relative to the user's body.

The third support member 222 connects between the lower portion 244 of the protective cup support 214 and the rear fastener 242. The third support member 222 includes a first end 262 which connects to the lower portion 244 of the protective cup support 14, and a second end 264 which adjustably connects to the rear fastener 242 of the waistband 212. The second end 264 of the third support member 222 may include a fastener 266 which cooperates with the rear fastener 242 to adjustably secure the third support member 222 to the waistband 212. The second end 264 of the third support member 222 may be moved to different positions relative to the waistband 212, wherein at each position, the fastener 266 engages the rear fastener 242 to adjustably tighten the protective cup support 214 relative to the user's body.

The fourth support member 224 connects between an upper side portion 268 of the protective cup support 214 the side fastener 240. The fourth support member 224 includes a first end 270 which connects to the upper side portion 268 of the protective cup support 214, and a second end 272 which adjustably connects to the side fastener 240 of the waistband 212. The second end 272 of the fourth support member 224 may include a fastener 274 which cooperates with the side fastener 240 to adjustably secure the fourth support member 224 to the waistband 212. The second end 272 of the fourth support member 224 may be moved to different positions relative to the waistband 212, wherein at each position, the fastener 274 engages the side fastener 240 to adjustably tighten the protective cup support 214 relative to the user's body.

The fifth support member 226 connects between an upper side portion 276 of the protective cup support 214 and the side fastener 241. The fifth support member 226 includes a first end 278 which connects to the upper side portion 276 of the protective cup support 214, and a second end 280 which adjustably connects to the side fastener 241 of the waistband 212. The second end 280 of the fifth support member 226 may include a fastener 282 which cooperates with the side fastener 240 to adjustably secure the fifth support member 226 to the waistband 212. The second end 280 of the fifth support member 226 may be moved to different positions relative to the waistband 212, wherein at each position, the fastener 282 engages the side fastener 241 to adjustably tighten the protective cup support 214 relative to the user's body.

The first, second, third, fourth and fifth support members 218, 220, 222, 224, 226 may each include an elongated component or strap made from a suitably resilient or elastic material. It should be appreciated that the suitably resilient or elastic material could include natural fibers such as cotton, linen or wool, synthetic fibers such as polyester, spandex or nylon, or various blends of natural and synthetic fibers such as cotton and polyester or spandex and nylon. It should also be appreciated that the first, second, third, fourth and fifth support members 218, 220, 222, 224, 226 may be made from any suitable material adapted to maintain the position of the protective cup 16 relative to the user's body when worn by that user.

Each of the first, second, third, fourth and fifth support members 218, 220, 222, 224, 226 may be adjustably connected or secured to the waistband 212. The adjustable connections enable a user to adjust the tension applied to the user's body to help reduce any movement of the protective cup support 214 and to increase the comfortabiltiy of the garment 200.

It should be appreciated that a user may wear garment 200 over an inner garment, such as a compression shorts, and under an outer garment, such as outer shorts. Because the first, second, third, fourth and fifth support members 218, 220, 222, 224, 226 attach or connect to the exterior of the waistband 212, the user may adjust the first, second, third, fourth and fifth support members 218, 220, 222, 224, 226 while wearing the garment 200.

Figure 12:
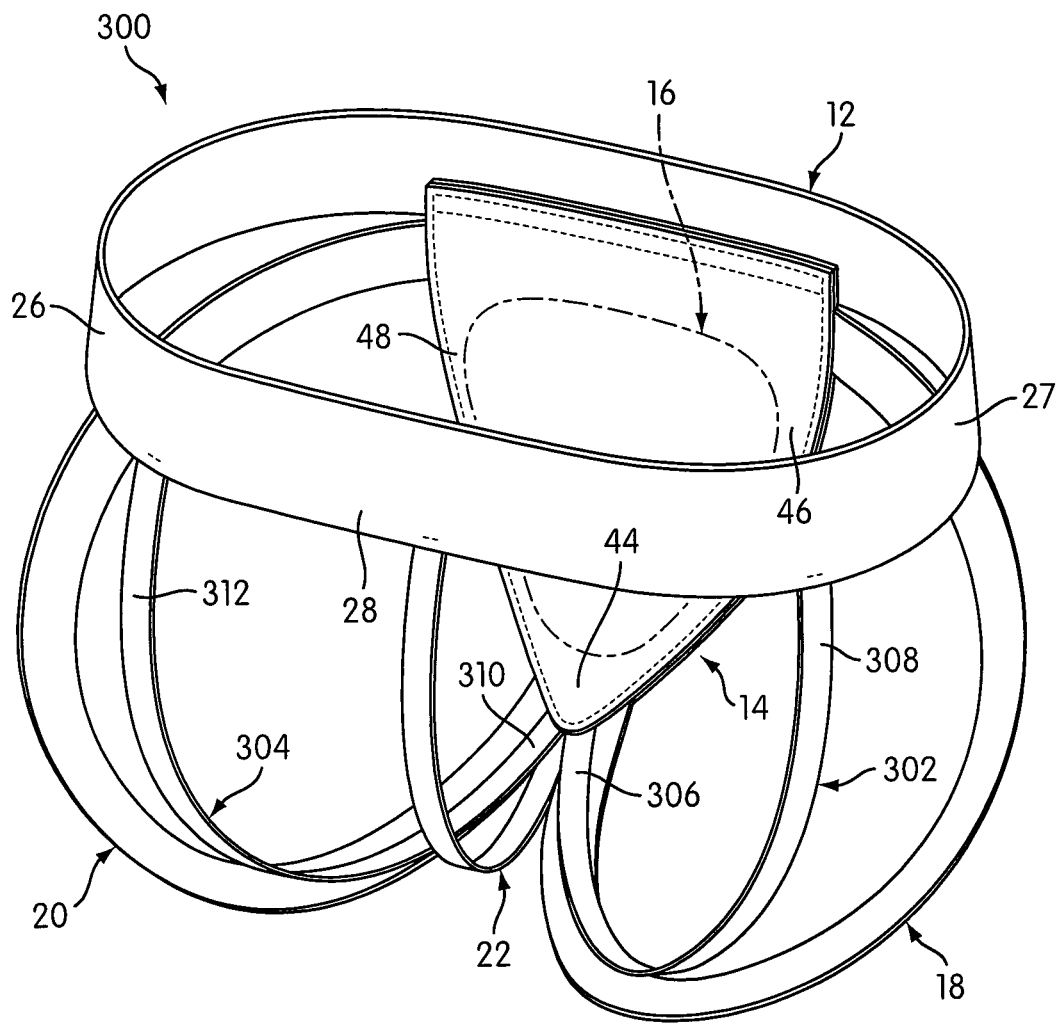
FIG. 12 illustrates a rear perspective view of an example embodiment of a garment for use with a protective cup.

Referring now to FIG. 12, an example embodiment of garment 300, such as a jock or an athletic supporter, is illustrated. The garment 300 includes similar elements as the garment 10 described above with respect to FIGS. 1 to 3. Those elements of garment 300 which are similar to garment 10 include like reference numerals. For example, the garment 300 may include an annular support member or waistband 12 that encircles a user's waist. The waistband 12 may connect or attach to a protective cup support 14. The protective cup support 14 is configured to support, hold or otherwise secure a protective cup 16 relative to a user's body. The garment 300 may include a first support member 18, a second support member 20 and a third support member 22 which cooperate with the waistband 12 to secure the protective cup support 14 relative to the user.

In an example embodiment, the garment 300 may include one or more support members in addition to the support members 18, 20, 22 described above. For example, the garment 300 may include a fourth support member 302 and a fifth support member 304. The fourth support member 302 may connect between the lower portion 44 of the protective cup support 14 and the waistband 12. The fourth support member 302 includes a first end 306 which may connect to the lower portion 44 of the protective cup support 14, and a second end 308 which may connect to the side region 27 of the waistband 12. The second end 308 may connect to the rear region 28 of the waistband 12, or to a section of the waistband 12 between the side and rear regions 27, 28. The fourth support member 302 maintains the lower portion 44 of the protective cup support 14 and the protective cup 16 in a preferred position relative to the user's body. In an example embodiment, the fourth support member 302 stabilizes the protective cup support 14 and the protective cup 16 in forward, backward and vertical directions when the garment 300 is worn by the user.

The fifth support member 304 may connect between the lower portion 44 of the protective cup support 14 and the waistband 12. The fifth support member 304 includes a first end 310 which may connect to the lower portion 44 of the protective cup support 14, and a second end 312 which may connect to the side region 26 of the waistband 12. The second end 312 may connect to the rear region 28 of the waistband 12, or to a section of the waistband 12 between the side and rear regions 26, 28. The fifth support member 304 maintains the lower portion 44 of the protective cup support 14 and the protective cup 16 in a preferred position relative to the user's body. In an example embodiment, the fifth support member 304 stabilizes the protective cup support 14 and the protective cup 16 in forward, backward and vertical directions when the garment 300 is worn by the user.

It should be appreciated that the garment 300 may include any suitable number of additional support members, which may be connected between the protective cup support 14 and the waistband 12. For example, sixth and seventh support members may connect the first and second side portions 46, 48 of the protective cup support 14 to either the side regions 26, 27 or the rear region 28 of the waistband 12.

Figure 13:
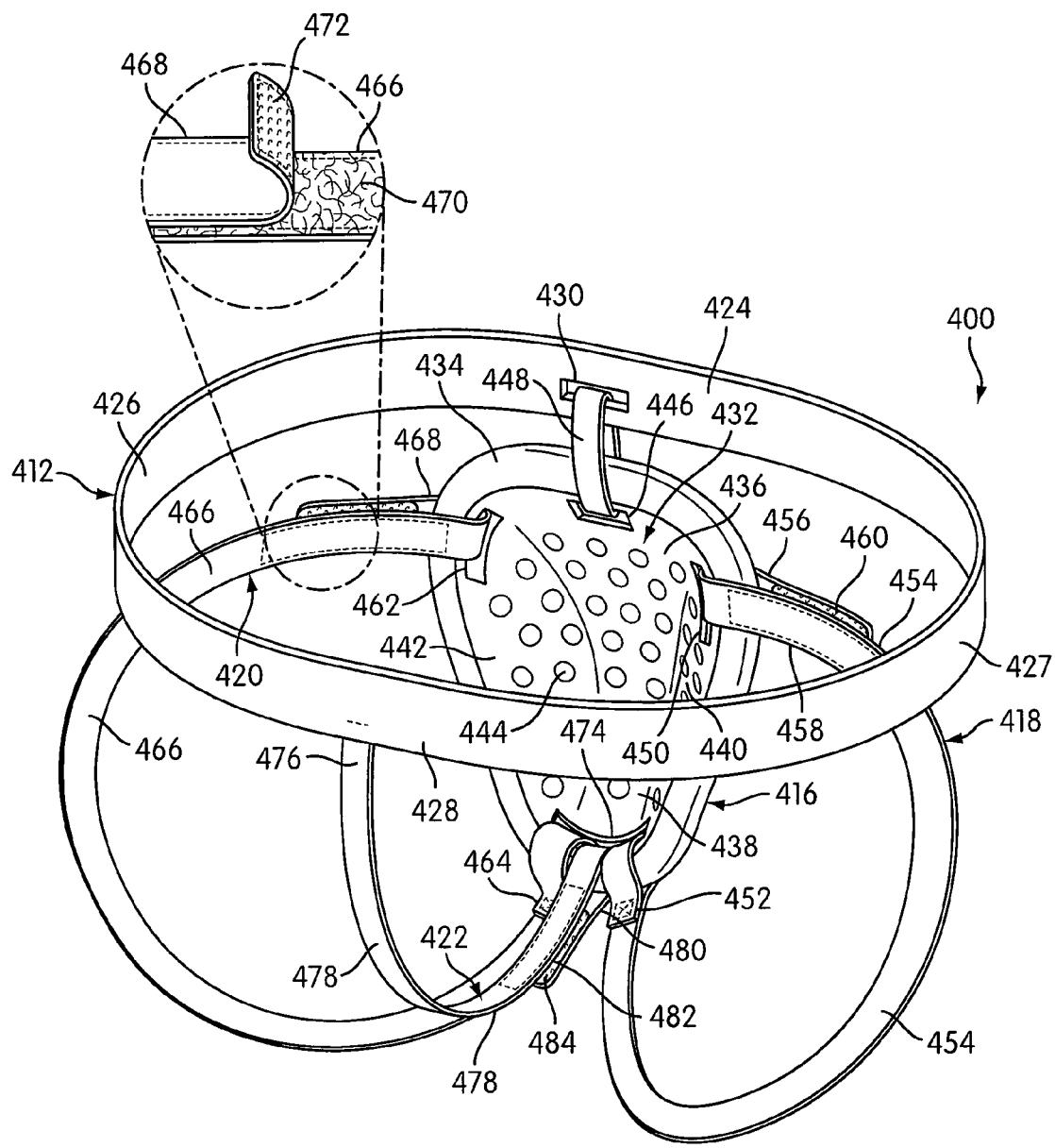
FIG. 13 illustrates a rear perspective view of an example embodiment of a garment for use with a protective cup, wherein certain portions of the example embodiment are enlarged for illustrative purposes.

Referring now to FIG. 13, an example embodiment of a garment 400 is illustrated. The garment 400 may include an annular support member 412 that encircles a user's waist and is commonly referred to as a waistband. The waistband 412 may connect or attach to a protective cup 416. The garment 400 includes a first support member 418, a second support member 420 and a third support member 422 which cooperate with the waistband 412 to secure the protective cup 416 relative to the user. Each of the first, second and third support members 418, 420, 422 has at least one end connected to the protective cup 416.

In an example embodiment, the waistband 412 may include an annular band of longitudinally elastic material which generally conforms to the waist of a user or person wearing the garment 400. The waistband 412 may include a fabric covering coextensive with and stitched to the elastic material. The waistband 412 may have a front region 424, side regions 426, 427 and a rear region 428. The side regions 426 separate the front region 424 from the rear region 428. The front region 424 of the waistband 412 may include a support member receiving aperture or opening 430, which may be configured to receive the second support member 422 therethrough, as described below in greater detail.

In an example embodiment, the protective cup 416 may include a substantially convex protective cup body 432 shaped and sized to protect a user's groin. In an example embodiment, a pad or padded portion 434 of a suitable thickness may extend along all or part of an edge or edge surface of the body 432. The padded portion 434 may be bonded, adhered or otherwise connected to the edge of the body 432 in any suitable manner. The thickness of the padded portion 434 creates separation between the body 432 and the user's groin, which may distribute the force of an impact or pressure over a suitably large area of the user's body wherein the cup 416 is positioned. The padded portion 434 may prevent the body 432 of the cup 416 from digging in, bruising or chaffing the user's body. In an example embodiment, the padded portion 434 may be shaped and have the appropriate thickness to reduce irritation and injury to the user's groin or legs, where the padded portion 434 is typically seated.

The body 432 of the protective cup 16 may include an upper area or portion 436, a lower area or portion 438, a first side area or portion 440 and a second side area or portion 442. The lower portion 438 may opposes the upper portion 436 along a vertical axis. The first side portion 440 and the second side portion 442 extend between the upper portion 436 and the lower portion 438. In an example embodiment, the first and second side portions 440, 442 extend from the upper portion 436, longitudinally oppose one another, and taper or narrow at the lower portion 438.

The cup body 432 may include zero, one or more openings 444 formed therein. The number of the openings 444 in the cup body 432 may reduce the weight of the protective cup 416. The number and positioning of the openings 444 in the cup body 432 may increase the ventilation through the protective cup 416. The protective cup 416 may include one or more padded layers, such as one or more padded layers 68 described above with respect to FIGS. 6B and 6C, which cover the cup body 432.

The upper portion 436 of the protective cup 416 may define an aperture or opening 446 therein, which may be configured to receive a waistband connector 448 therethrough. The waistband connector 448 may extend through the opening 446 formed in the upper portion 436 of the protective cup 416 and the opening 430 formed in the waistband 412. The waistband connector 448 may adjustably or fixedly connect the upper portion 436 of the protective cup 416 to the front region 424 of the waistband 412. In an example embodiment, the waistband connector 448 includes an annular band of resilient or elastic material. The waistband connector 448 may be a variety of suitable connectors, such as an adjustable band or any other connector configured to directly or indirectly connect the protective cup 416 to the waistband 412.

It should be appreciated that the protective cup 416 may directly connect to the front region 424 of the waistband 412. For example, the front region 424 of the waistband 412 may include a first end connected to at least one of the upper portion 436 and the first side portion 440 of the protective cup 416 and a second end connected to at least one of the upper portion 436 and the second side portion 442 of the protective cup 416. It should be also appreciated that the protective cup 416 may directly connect to the side regions 426, 427 of the waistband 412. For example, the side region 426 of the waistband 412 may include a first end connected to at least one of the upper portion 436 and the first side portion 440 of the protective cup 416 and the side region 427 of the waistband 412 may include a second end connected to at least one of the upper portion 436 and the second side portion 442 of the protective cup 416.

The first side portion 440 of the protective cup 416 may define a support member receiving aperture or opening 450 therein. The support member receiving opening 450 may be configured to receive the first support member 418 therethrough. In an example embodiment, the first support member 418 connects between the lower portion 438 and the first side portion 440 of the protective cup 416. The first support member 418 includes a first end 452, a body 454 and a second end 456. The body 454 may extend between the first end 452 and the second end 456. The body 454 may have a first fastener 458 stitched to, connected to, or otherwise formed integral with the body 454. The second end 456 may have a second fastener 460 stitched to, connected to, or otherwise formed integral with the second end 456.

The first end 452 may connect to the lower portion 438 of the protective cup 416. In an example embodiment, the first end 452 may be fixedly connected to the lower portion 438 of the protective cup 416. In another example embodiment, the first end 452 may be adjustably connected to the lower portion 438 of the protective cup 416.

The second end 456 may connect to the side portion 440 by extending through the support member receiving opening 450 formed in the side portion 440 of the protective cup 416. In an example embodiment, the second end 456 may be fixedly connected to the side portion 440 of the protective cup 416. In another example embodiment, the second end 456 may be adjustably connected to the side portion 440 of the protective cup 416. For example, the second fastener 460 may cooperate with the first fastener 458 to adjustably connect the second end 456 to the side portion 440 of the protective cup 416. The second end 456 may be moved to different positions along the body 454, and secured thereto by the fasteners 458, 460, to change or adjust the position and fit of the protective cup 416 relative to the user's body. The first support member 418 is adapted to maintain the lower portion 438 and the side portion 440 of the protective cup 416 in a preferred position relative to the user's body. In an example embodiment, the first support member 418 stabilizes the protective cup 416 in lateral or side-to-side directions when the garment 400 is worn by the user.

The second side portion 442 of the protective cup 416 may define a support member receiving aperture or opening 462 therein. The support member receiving opening 462 may be configured to receive the second support member 420 therethrough. In an example embodiment, the second support member 420 connects between the lower portion 438 and the second side portion 442 of the protective cup 416. The second support member 420 includes a first end 464, a body 466 and a second end 468. The body 466 may extend between the first end 464 and the second end 468. The body 466 may have a first fastener 470 stitched to, connected to, or otherwise formed integral with the body 466. The second end 468 may have a second fastener 472 stitched to, connected to, or otherwise formed integral with the second end 468. It should be appreciated that FIG. 13 shows an enlarged view of the body 466, the second end 468, the first fastener 470 and the second fastener 472 from a reverse perspective for illustrative purposes.

The first end 464 may connect to the lower portion 438 of the protective cup 416. In an example embodiment, the first end 464 may be fixedly connected to the lower portion 438 of the protective cup 416. In another example embodiment, the first end 464 may be adjustably connected to the lower portion 438 of the protective cup 416.

The second end 468 may connect to the side portion 442 by extending through the support member receiving opening 462 formed in the side portion 442 of the protective cup 416. In an example embodiment, the second end 468 may be fixedly connected to the side portion 442 of the protective cup 416. In another example embodiment, the second end 468 may be adjustably connected to the side portion 442 of the protective cup 416. For example, the second fastener 472 may cooperate with the first fastener 470 to adjustably connect the second end 468 to the side portion 442 of the protective cup 416. The second end 468 may be moved to different positions along the body 466, and secured thereto by the fasteners 470, 472, to change or adjust the position and fit of the protective cup 416 relative to the user's body. The second support member 420 is adapted to maintain the lower portion 438 and the side portion 442 of the protective cup 416 in a preferred position relative to the user's body. In an example embodiment, the second support member 420 stabilizes the protective cup 416 in lateral or side-to-side directions when the garment 400 is worn by the user.

The lower portion 438 of the protective cup 416 may define a support member receiving aperture or opening 474 therein. The support member receiving opening 474 may be configured to receive any one of the first support member 418, the second support member 420 and the third support member 422 therethrough. In an example embodiment, the third support member 422 connects between the lower portion 438 of the protective cup 416 and the rear portion 428 of the waistband 412. The third support member 422 includes a first end 476, a body 478 and a second end 480. The body 478 may extend between the first end 476 and the second end 480. The body 478 may have a first fastener 482 stitched to, connected to, or otherwise formed integral with the body 478. The second end 480 may have a second fastener 484 stitched to, connected to, or otherwise formed integral with the second end 480.

The first end 476 may connect to the rear portion 428 of the waistband 412. In an example embodiment, the first end 476 may be fixedly connected to the rear portion 428 of the waistband 412. In another example embodiment, the first end 476 may be adjustably connected to the rear portion 428 of the waistband 412. For example, the first end 476 may extend through a support member receiving opening formed in the rear portion 428 of the waistband 412 and may fixedly or adjustably connect to the rear portion 428 of the waistband 412.

The second end 480 may connect to the lower portion 438 of the protective cup 416 by extending through the support member receiving opening 474 formed in the lower portion 438 of the protective cup 416. The second fastener 484 may cooperate with the first fastener 482 to adjustably connect the second end 480 to the lower portion 438 of the protective cup 416. The second end 480 may be moved to different positions along the body 478, and secured thereto by the fasteners 482, 484, to change or adjust the position and fit of the protective cup 416 relative to the user's body. The third support member 422 is adapted to maintain the lower portion 438 of the protective cup 416 in a preferred position relative to the user's body. In an example embodiment, the third support member 422 stabilizes the protective cup 416 in forward, backward and vertical directions when the garment 400 is worn by the user.

In an example embodiment, the fasteners 458, 460, 472, 474, 482, 484 may be stitched to, connected to, or otherwise formed integral with the second ends 456, 468, 480 of the first, second and third support members 418, 420, 422. For example, the second end 456 may include the fasteners 458, 460 so that the second end 456 extends through the opening 450 and adjustably connects to itself via the fasteners 458, 460. The fasteners 458, 460, 472, 474, 482, 484 may be any variety of suitable fastener, such as hook and loop type fasteners. It should be appreciated that the fasteners 458, 460, 472, 474, 482, 484 may be sized and positioned to enable adjustability of the first, second and third support members 418, 420, 422 to different adjustable positions.

In an example embodiment, the openings 446, 450, 462, 474 formed in the protective cup 416 may each be replaced by a flange or extension connected to the protective cup 416. Each flange may connect to the protective cup 416 by stitching, molding, or any other suitable connection. Each flange may define an opening therein which may receive at least one of the first, second and third support members 418, 420, 422 therethrough. The ends 456, 468, 480 of the first, second, and third support members 418, 420, 422 may each fixedly or adjustably connect to one of the flanges. In an example embodiment, the flanges may indirectly connect the first, second and third support members 418, 420, 422 to the protective cup 416.

In an example embodiment, the end 452 of the first support member 418, the end 464 of the second support member 420 may be adjustable to different positions to maintain the lower portion 438 of the protective cup 416 in a preferred position and reduce movement thereof in forward, backward and vertical directions. In an example embodiment, the end 476 of the third support member 422 may be adjustable to different positions to maintain the lower portion 438 of the protective cup 416 in a preferred position and reduce movement thereof in forward, backward and vertical directions.

In an example embodiment, the first, second and third support members 418, 420, 422 may each include an elongated component or strap made from a suitably resilient or elastic material. It should be appreciated that the suitably resilient or elastic material may include natural fibers such as cotton, linen or wool, synthetic fibers such as polyester, spandex or nylon, or various blends of natural and synthetic fibers such as cotton and polyester or spandex and nylon. The resilient or elastic material may include a fabric having any suitable weave or pattern. The first, second, third support members 418, 420, 422 may each be formed from a non-elastic material, such as leather or any other suitable extensible material. It should be appreciated that the waistband 412, the protective cup support 414, the first support member 418, the second support member 420 and the third support member 422 may be made from any stretchable material, such as elastic material or extensible material, adapted to maintain the position of the protective cup 416 relative to the user's body when worn by that user.

Referring now to FIGS. 14 to 17, an example embodiment of a garment 500 is illustrated. Garment 500 may be referred to as an inner garment or a compression short. The garment 500 may include a short member 510 connected to a waistband 512 by stitching, by having portions integral with the waistband 512, or by any suitable connection or fastener. The garment 500 may also include a protective cup support 514 for supporting a protective cup 516, a first support member 518, a second support member 520 and a third support member 522. The waistband 512, the protective cup support 514, the first support member 518, the second support member 520 and the third support member 522 may be substantially similar to the waistband 12, the protective cup support 14, the first support member 18, the second support member 20 and the third support member 22 described above with respect to FIGS. 1 to 3, 4A and 4B.

The short member 510 may include a plurality of interior portions connected to the waistband 512, the protective cup support 514, the first support member 518, the second support member 520 and the third support member 522 by stitching or any other suitable connection. In an example embodiment, the short member 510 includes a front portion 524, a rear portion 526 and respective side portions 528, 530 interconnecting the front portion 524 and the rear portion 526. The front portion 524, the side portion 528 and the rear portion 526 cooperate to form a first leg portion 532. The front portion 524, the side portion 530 and the rear portion 526 cooperate to form a second leg portion 534. The first and second leg portions 532, 534 are separated from one another by an inseam 536. The front portion 524, the rear portion 526, the side portions 528, 530, and the leg portions 532, 534 each have an interior surface which is configured to contact the user's body when the garment 500 is worn by the user, and an exterior surface which opposes the interior surface.

It should be appreciated that the inseam 536 may have different lengths, which enables the leg portions 532, 534 to have different lengths. In an example embodiment, the leg portions 532, 534 and the inseam 536 may be sized to form leg openings which extend to a portion of the user's leg (e.g., the user's thigh). For example, the inseam 536 may be sized so that when a user wears the garment 500, the leg portions 532, 534 extend to a portion of the user's legs above the user's knees. In another example, the inseam 536 may be sized so that when a user wears the garment 500, the leg portions 532, 534 extend to a portion of the user's leg below the user's knees. For example, when a user wears the garment 500, the inseam 536 may be sized so that the leg portions 532, 534 extend to a portion of the user's legs at or below the user's ankles.

In an example embodiment, the first leg portion 532 includes a protective pad support 538 disposed on the exterior surface thereof. The protective pad support 538 may define an interior space that is configured to receive a leg pad 542 which may be inserted in and removed from the protective pad support 538. The protective pad support 538 may include an upper exterior portion 544 which overlaps a lower exterior portion 546 by a designated amount (e.g., about one inch, about two and one-half centimeters or any other suitable amount) to define a protective pad receiving aperture 548. In an example embodiment, the lower exterior portion 546 may overlap the upper exterior portion 544 by a designated amount to define the protective pad receiving aperture 548. The upper exterior portion 544 may be separable from the lower exterior portion 546 to access the interior space of the protective pad support 538 through the protective pad receiving aperture 548. The aperture 548 may have a width that is sized to accommodate a width of the leg pad 542 such that the leg pad 542 may be inserted through the protective pad receiving aperture 548 and received by the interior space of the protective pad support 538. For example, a user may access the interior space (e.g., to position the leg pad 542) through the protective pad receiving aperture 548 of the protective pad support 538.

In an example embodiment, the second leg portion 534 includes a protective pad support 540 disposed on the exterior surface thereof. The protective pad support 540 may be substantially similar to the protective pad support 538 of the first leg portion 532. The protective pad support 540 may define an interior space that is configured to receive a leg pad 542 which may be inserted in and removed from the protective pad support 540. The protective pad support 540 may include an upper exterior portion 550 which overlaps a lower exterior portion 552 by a designated amount (e.g., about one inch, about two and one-half centimeters or any other suitable amount) to define a protective pad receiving aperture 554. In an example embodiment, the lower exterior portion 552 may overlap the upper exterior portion 550 by a designated amount to define the protective pad receiving aperture 554. The upper exterior portion 550 may be separable from the lower exterior portion 552 to access the interior space of the protective pad support 540 through the protective pad receiving aperture 554. The aperture 554 may have a width that is sized to accommodate a width of the leg pad 542 such that the leg pad 542 may be inserted through the protective pad receiving aperture 554 and received by the interior space of the protective pad support 540. For example, a user may access the interior space (e.g., to position the leg pad 542) through the protective pad receiving aperture 554 of the protective pad support 540.

The protective pad supports 538, 540 of the first and second leg portions 532, 534 may each be configured to receive separate leg pads 542. The leg pads 542 may be inserted in and removed from the protective pad supports 538, 540. The leg pad 542 may be shaped to conform to the interior space defined by each protective pad support 538, 540. The leg pad 542 may include any suitable material or padding, such as rubber, foam or any other suitable material which absorbs, disperses or reduces impact. For example, the leg pad 542 may include a first layer made of a first material and a second layer made of a second material. In an example embodiment, the protective pad supports 538, 540 and the leg pads 542 are positioned on the short member 510 and shaped for specific activities.

In an example embodiment, the front portion 524 of the short member 510 may include a protective pad support 556 disposed on the exterior surface thereof. The protective pad support 556 may be substantially similar to the protective pad supports 538, 540 of the leg portions 532, 534. The protective pad support 556 may define an interior space that is configured to receive a groin region pad 558 which may be inserted into and removed from the protective pad support 556. The protective pad support 556 may include an upper exterior portion 560 which overlaps a lower exterior portion 562 by a designated amount (e.g., about one inch, about two and one-half centimeters or any other suitable amount) to define a protective pad receiving aperture 564. In an example embodiment, the lower exterior portion 562 may overlap the upper exterior portion 560 by a designated amount to define the protective pad receiving aperture 564. The upper exterior portion 560 may be separable from the lower exterior portion 562 to access the interior space of the protective pad support 556 through the protective pad receiving aperture 564. The aperture 564 may have a width that is sized to accommodate a width of the groin region pad 558 such that the groin region pad 558 may be inserted through the protective pad receiving aperture 564 and received by the interior space of the protective pad support 556. For example, a user may access the interior space (e.g., to position the groin region pad 558) through the protective pad receiving aperture 564 of the protective pad support 556.

The protective pad support 556 is configured to receive the groin region pad 558. The groin region pad 558 may be inserted in and removed from the protective pad support 556. The groin region pad 558 may be shaped to conform to the interior space defined by the protective pad support 556. The groin region pad 558 may include any suitable material or padding, such as rubber, foam or any other suitable material which absorbs, disperses or reduces impact. For example, the groin region pad 558 may include a first layer made of a first material and a second layer made of a second material. In an example embodiment, the protective pad support 556 and the groin region pad 558 are positioned on the short member 510 and shaped for specific activities.

It should be appreciated that the protective pad support 556 and the protective pad supports 538, 540 may fixedly support the groin region pad 558 and the leg pads 542, respectively. For example, the groin region pad 558 and the leg pads 542 may be stitched or enclosed in any suitable manner within the protective pad support 556 and the protective pad supports 538, 540.

In an example embodiment, the leg portions 532, 534 may include one or more protective pad supports configured to receive protective pads to protect the user's buttocks, hips, thighs, shins or knees. The protective pad supports and the protective pads for protecting the user's buttocks, hips, thighs, shins or knees may be substantially similar to the protective pad supports 538, 540, 556, the leg pads 542 and the groin region pad 558 described above.

Figure 14:
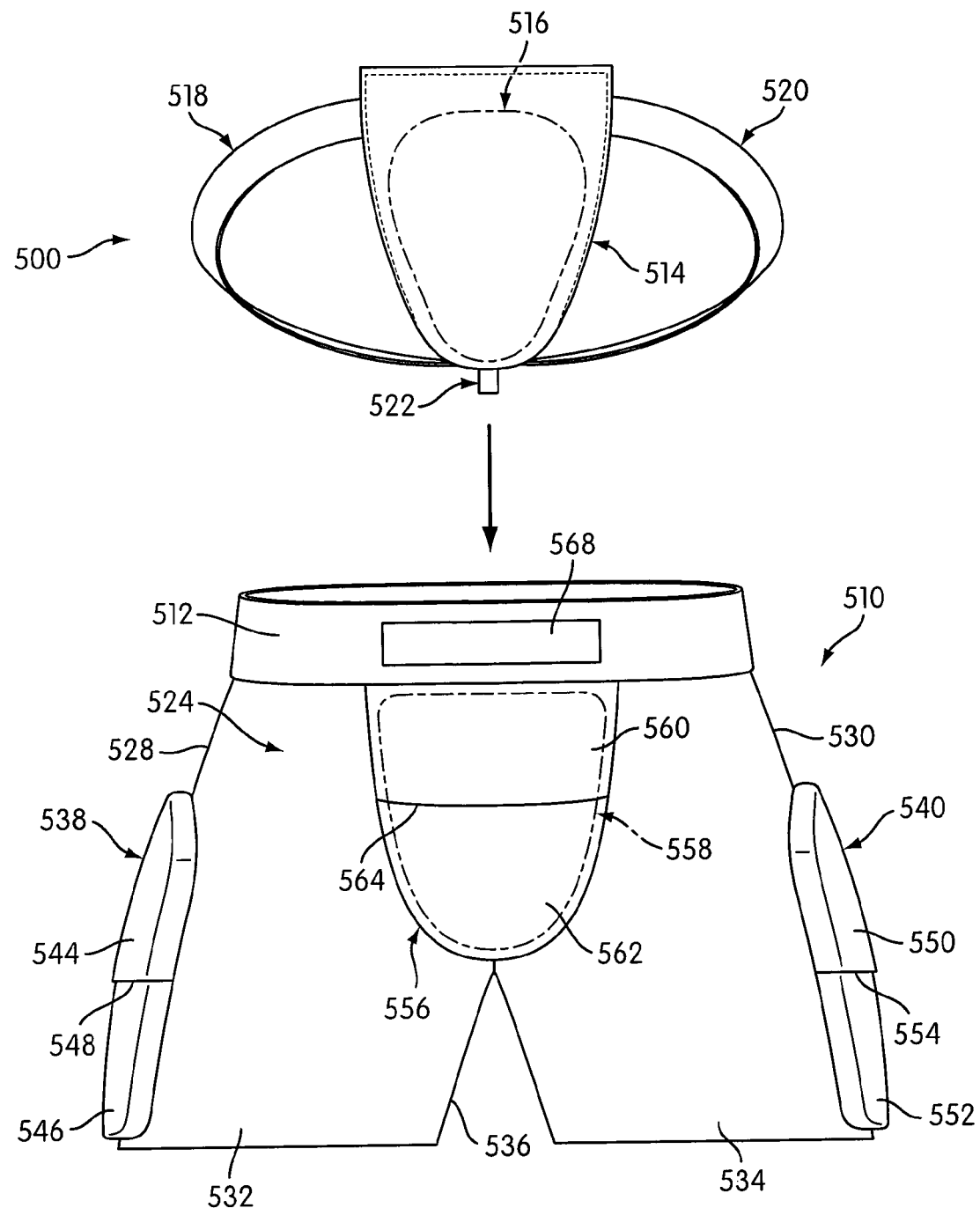
FIG. 14 illustrates an exploded view of an example embodiment of an inner garment for use with a protective cup.
Figure 15:
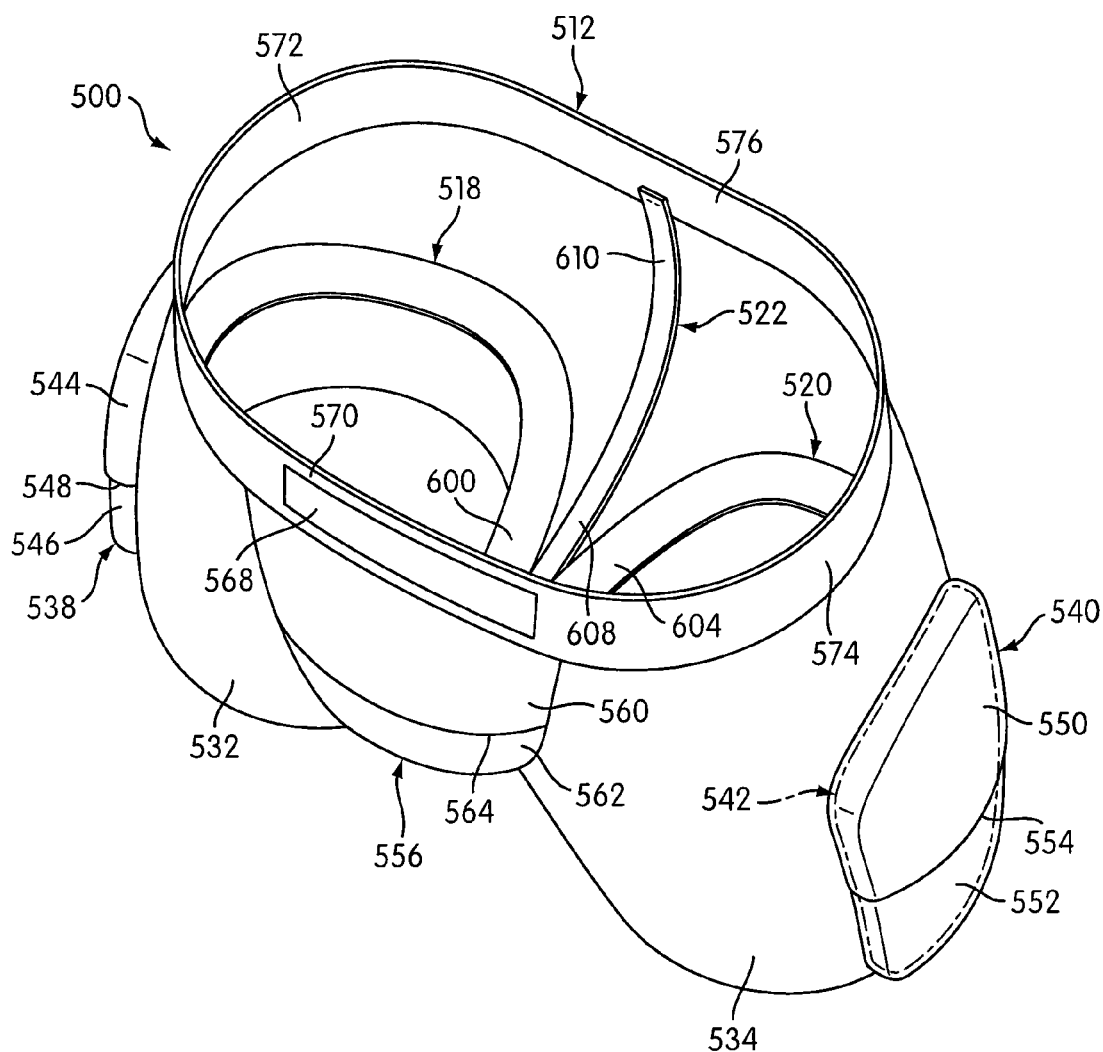
FIG. 15 illustrates a top, side perspective view of the example embodiment shown in FIG. 14.
Figure 16:
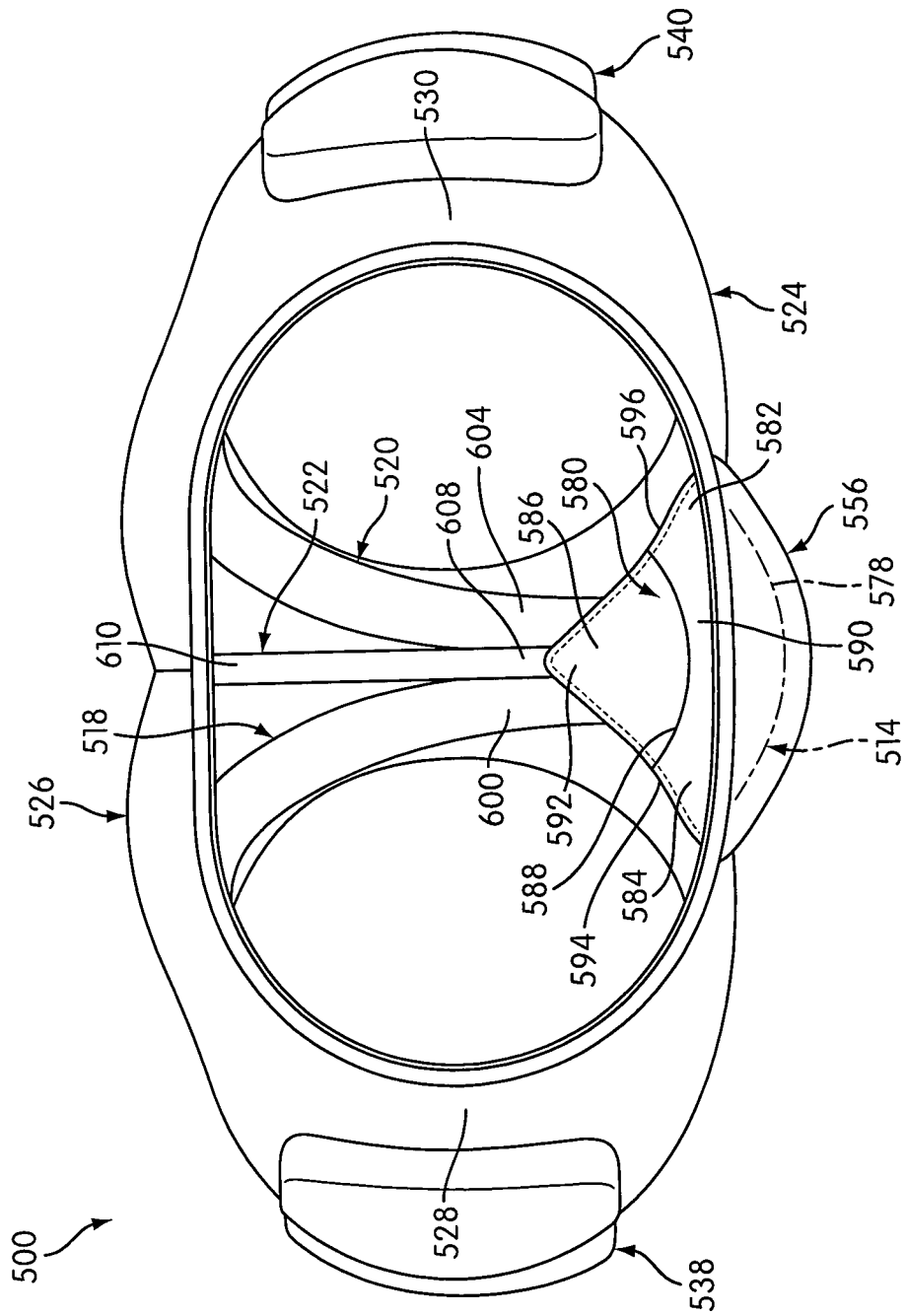
FIG. 16 illustrates a top view of the example embodiment shown in FIG. 14.
Figure 17:
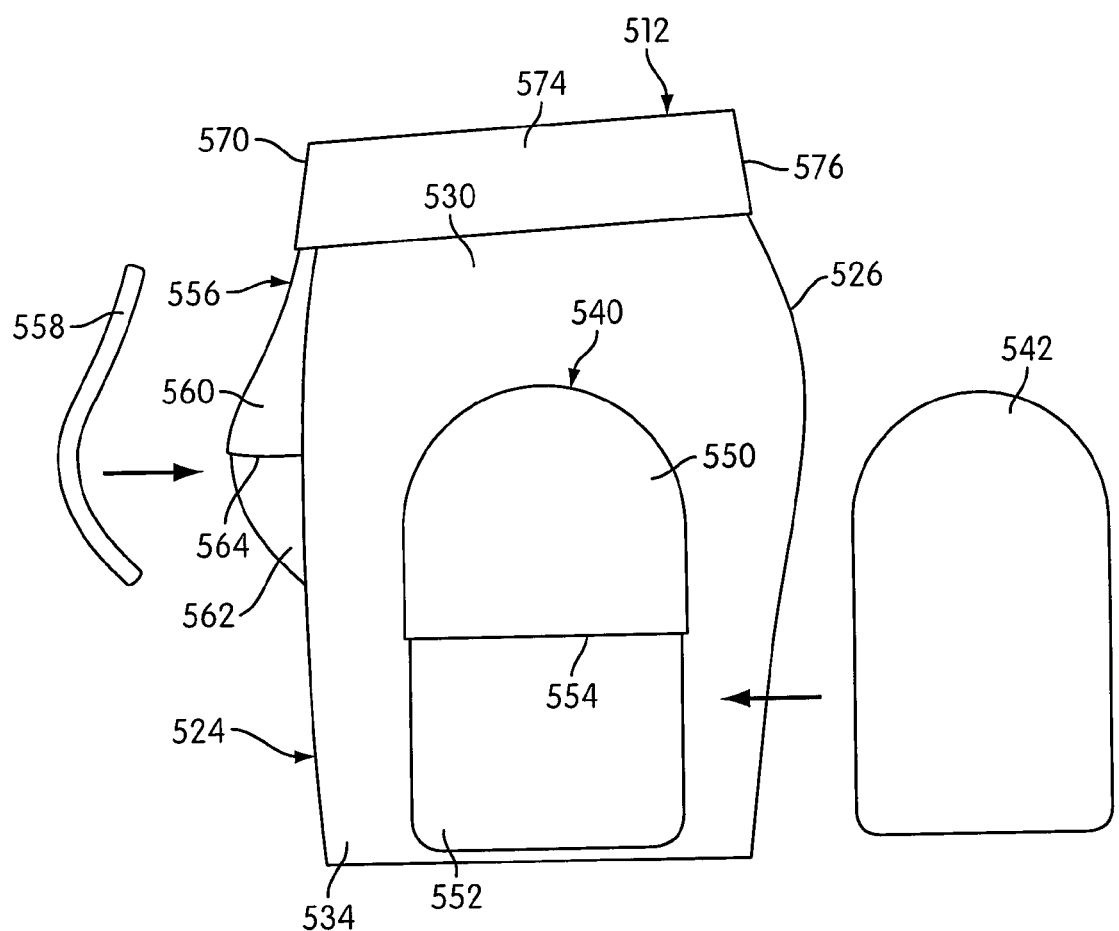
FIG. 17 illustrates a side view of the example embodiment shown in FIG. 14.
Figure 18:
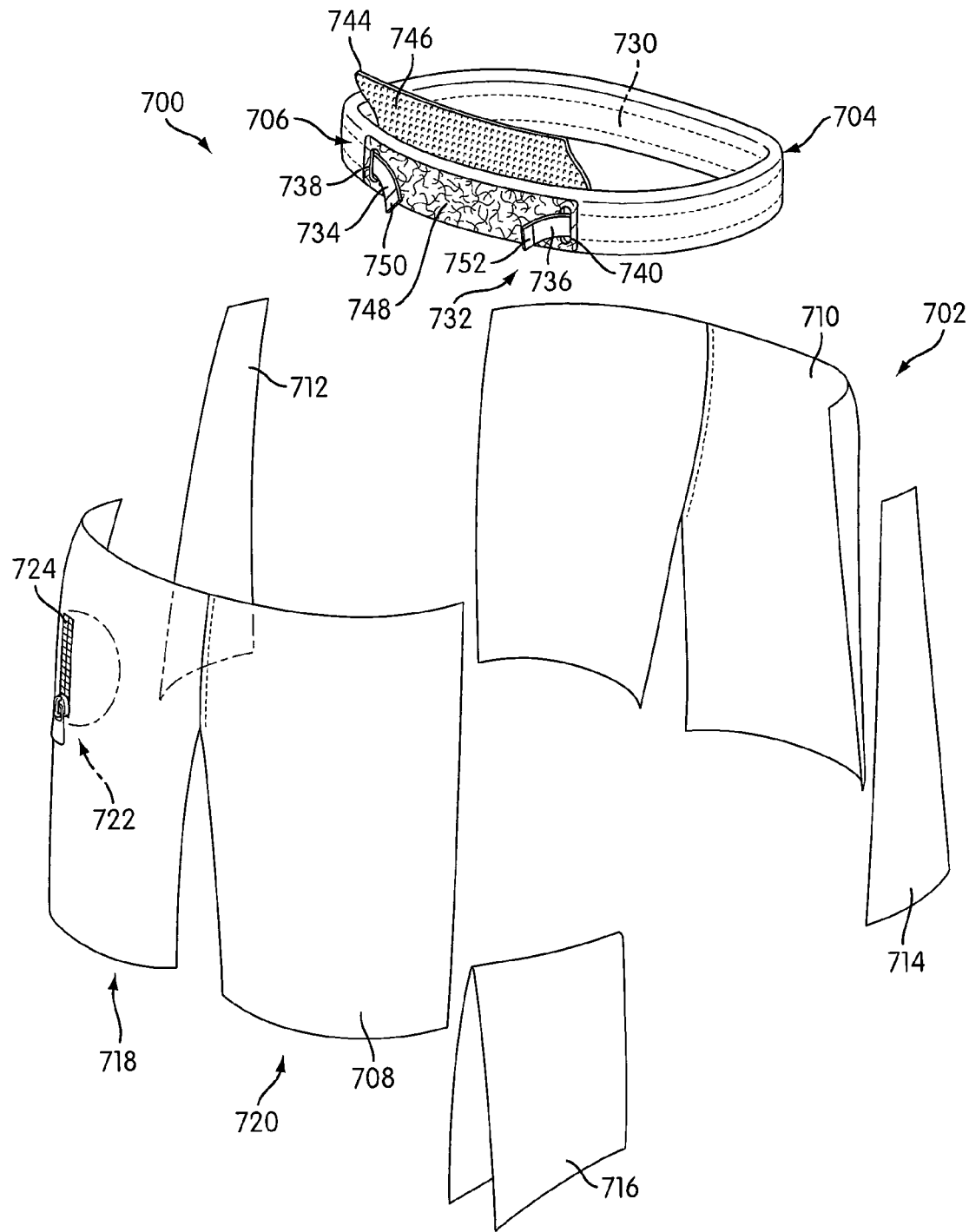
FIG. 18 illustrates an exploded view of an example embodiment of a fastening system on an example embodiment of an outer garment.
Figure 19:
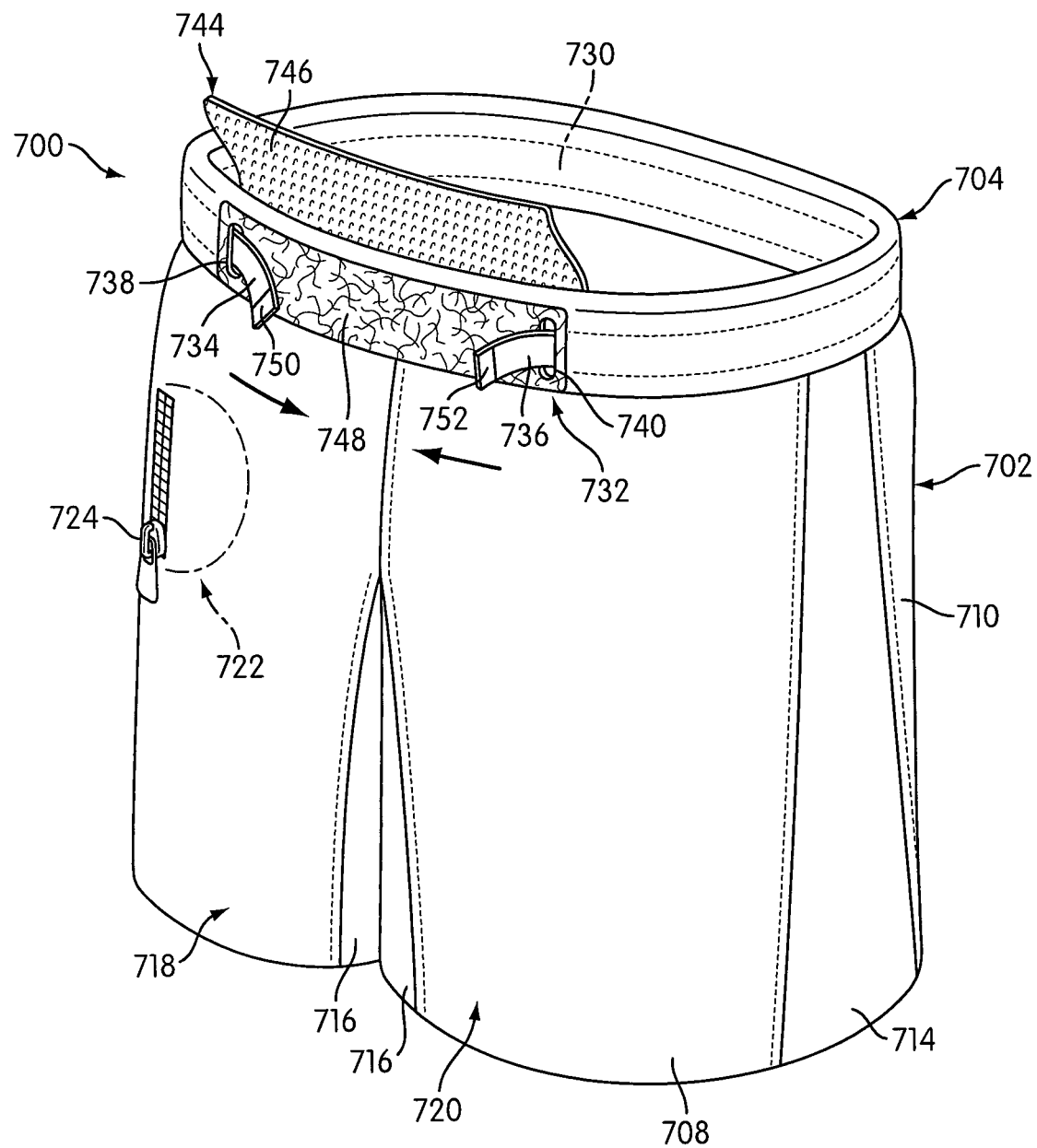
FIG. 19 illustrates a perspective view of the example embodiment shown in FIG. 18.

Referring now to FIGS. 14 to 16, the waistband 512 includes a branding region 568, a front region 570, side regions 572, 574 and a rear region 576. Each of the side regions 572, 574 separate the front region 570 from the rear region 576. The front, side and rear regions 570, 572, 574, 576 of the waistband 512 may align with, and be connected to, the front, side and rear portions 524, 526, 528, 530 of the garment 500 by stitching or any other suitable connection.

In an example embodiment, the branding region 568 may be configured to display branding or marketing information, such as an advertisement or sponsorship. For example, the branding or marketing information may be attached to, printed on, stitched to, or otherwise coupled with the branding region 568 in any suitable manner. The branding region 568 may be positioned along any one, a plurality of, or each of the front region 570, the side regions 572, 574, and the rear region 576.

In an example embodiment, the protective cup support 514 includes a front panel 578 which may connect to a rear panel 580 by stitching or any other suitable manner. The front panel 578 and the rear panel 580 are connected to, and cooperate with, one another to form an interior space or pocket 582. The interior space 582 is configured to receive or otherwise secure the protective cup 516, which may be substantially similar to the protective cup 16.

The rear panel 580 includes a first portion 584 which overlaps a second portion 586 by a designated amount (e.g., about one inch, about two and one-half centimeters or any other suitable amount). The first portion 584 is separable from the second portion 586 to form an aperture or slot 588 which provides access to the interior space 582. The aperture 588 may have a width that is sized to accommodate a width of a protective cup such that the protective cup may be inserted through the aperture 588 and received by the interior space 582. For example, a user may access the interior space 582 (e.g., to position the protective cup) through the aperture 588 on the rear panel 580 of the protective cup support 514. The protective cup support 514 may include a closure member to close the protective cup receiving aperture 588 (e.g., to fasten the first portion 584 to the second portion 586), such as a snap, a button, a zipper or any other suitable separable fasteners, such as hook and loop type fasteners.

It should be appreciated that the protective cup support 514 may be sized and shaped to substantially conform to the protective cup 516. In an example embodiment, the protective cup support 514 is sized to accommodate the protective cup 516 and to reduce the ability or likelihood of the cup 516 shifting or moving within the interior space 582 of the protective cup support 514. For example, when the protective cup 516 is received by the interior space 582, the protective cup support 514 is configured such that the rear panel 580 supports a rear portion of the protective cup 516, the first portion 584 supports an upper, front portion of the protective cup 516, the second portion 586 supports a lower, front portion of the protective cup 516, and the waistband 512, the front panel 578 and the rear panel 580 support an upper portion of the protective cup 516.

In an example embodiment, the front panel 578 and the rear panel 580 connect together to form an upper area or portion 590, a lower area or portion 592, a first side area or portion 594 and a second side area or portion 596 of the protective cup support 514. The upper portion 590 may connect to the front region 570 of the waistband 512 by stitching, by having portions integral with the waistband 512, or with any suitable connection or fastener. For example, the upper portion 590 of the front and rear panels 578, 580 may be connected to, and cooperate with, the front region 570 of the waistband to form the interior space or pocket 582. The first side portion 594 and the second side portion 596 extend between the upper portion 590 and the lower portion 592. The first and second side portions 594, 596 may extend from the upper portion 590, longitudinally oppose one another, and taper or narrow at the lower portion 592. The lower portion 592 may be suspended between the front portion 524, the rear portion 526 and the side portions 528, 530 of the garment 500.

In an example embodiment, the protective cup support 514 may be positioned between the front portion 524, the rear portion 526 and the side portions 528, 530 to substantially align with the protective pad support 556 disposed on the exterior surface of the front portion 524. The protective cup support 514 may be positioned relative to the protective pad support 556 and the groin region pad 558 so that the groin region pad 558 may absorb, disperse or reduce the amount of force or speed of an impact to the user's groin region.

In an example embodiment, the upper portion 590 connects to the front region 570 of the waistband 512 with stitching, by having portions integral with the waistband 512, or with any suitable connection or fastener. The side portions 594, 596 may each connect to the interior surface of the front portion 524 of the garment 500 with stitching, by having portions integral with the front portion 524, or with any suitable connection or fastener. The side portions 594, 596 may connect to the interior surface of the front portion 524 to maintain the protective cup support 514 and the protective cup 516 in a preferred position relative to the user's body. For example, the side portions 594, 596 may stabilize the protective cup support 514 and the protective cup 516 in lateral or side-to-side directions.

In an example embodiment, the lower portion 592 and the side portions 594, 596 each connect to the interior surface of the front portion 524 of the garment 500 with stitching, by having portions integral with the front portion 524, or with any suitable connection or fastener. The lower portion 592 and the side portions 594, 596 may connect to the interior surface of the front portion 524 to maintain the protective cup support 514 and the protective cup 516 in a preferred position relative to the user's body. For example, the lower portion 592 may stabilize the protective cup support 514 and the protective cup 516 in forward, backward and vertical directions and the side portions 594, 596 may stabilize the protective cup support 514 and the protective cup 516 in lateral or side-to-side directions.

In an example embodiment, the upper portion 590 connects to the front region 570 of the waistband 512 with stitching, by having portions integral with the waistband 512, or with any suitable connection or fastener. The lower portion 592 connects to the interior surfaces of the front and rear portions 524, 526 of the garment 500 with stitching, by having portions integral with the front portion 524, or with any suitable connection or fastener. The lower portion 592 may connect to the interior surfaces of the front and rear portions 524, 526 to maintain the protective cup support 514 and the protective cup 516 in a preferred position relative to the user's body. For example, the lower portion 592 may stabilize the protective cup support 514 and the protective cup 516 in forward, backward and vertical directions.

In an example embodiment, the first support member 518 connects between the lower portion 592 and the first side portion 594 of the protective cup support 514. The first support member 518 includes a first end 600 which may connect to the lower portion 592 of the protective cup support 514, and a second end 602 which may connect to the first side portion 594 of the protective cup support 514. The first support member 518 is adapted to maintain the lower portion 592 and the side portion 594 of the protective cup support 514 and the protective cup 516 in a preferred position relative to the user's body. In an example embodiment, the first support member 518 stabilizes the protective cup support 514 and the protective cup 516 in lateral or side-to-side directions when the garment 500 is worn by the user.

The second support member 520 connects between the lower portion 592 and the second side portion 596 of the protective cup support 514. The second support member 520 includes a first end 604 which connects to the lower portion 592 of the protective cup support 514, and a second end 606 which connects to the second side portion 596 of the protective cup support 514. The second support member 520 maintains the lower portion 592 and the side portion 596 of the protective cup support 514 and the protective cup 516 in a preferred position relative to the user's body. In an example embodiment, the second support member 520 stabilizes the protective cup support 514 and the protective cup 516 in lateral or side-to-side directions when the garment 500 is worn by the user.

The third support member 522 connects between the lower portion 592 of the protective cup support 514 and the waistband 512. The third support member 522 includes a first end 608 which connects to the lower portion 592 of the protective cup support 514, and a second end 610 which connects to the rear portion 576 of the waistband 512. The third support member 522 maintains the lower portion 592 of the protective cup support 514 and the protective cup 516 in a preferred position relative to the user's body. In an example embodiment, the third support member 522 stabilizes the protective cup support 514 and the protective cup 516 in forward, backward and vertical directions when the garment 500 is worn by the user.

The first end 600 of the first support member 518, the first end 604 of the second support member 520 and the first end 608 of the third support member 522 may each connect to the lower portion 592 of the protective cup support 514 at a same location or at a substantially same location. The first end 600 of the first support member 518, the first end 604 of the second support member 520 and the first end 608 of the third support member 522 may each connect to the lower portion 592 of the protective cup support 514 at different locations (e.g., for the ends 600, 604, 608 to have a spaced relationship with one another at the lower portion 592).

The first end 600 of the first support member 518, the first end 604 of the second support member 520 and the ends 608, 610 of the third support member 522 may include an elastic component having sufficient elastic tension to maintain the lower portion 592 of the protective cup support 514 and the protective cup 516 in a preferred position and reduce movement of the support 514 and the cup 516 in forward, backward, lateral and vertical directions. The ends 602, 606 of the first and second support members 518, 520 may include an elastic component having sufficient elastic tension to maintain the side portions 594, 596 of the protective cup support 514 and the protective cup 516 in a preferred position and reduce movement of the support 514 and the cup 516 in lateral or side-to-side directions.

It should be appreciated that the waistband 512, the protective cup support 514, the first support member 518, the second support member 520 and the third support member 522 may be made from similar materials as the waistband 12, the protective cup support 14, the first support member 18, the second support member 20 and the third support member 22 described above.

Referring now to FIGS. 18 to 21, an example embodiment of garment 700 is illustrated. The garment 700 may be referred to as an outer garment, such as athletic shorts or outer shorts. The garment 700 may include a short member 702 connected to an exterior waistband portion 704 with stitching, by having portions integral with the waistband portion 704, or with any suitable connection or fastener. The waistband portion 704 may include a fastening system 706 to hold the exterior waistband portion 704 and the short member 702 about a user's waist or trunk.

The garment 700 may be worn by a user alone, or in combination with the garment 100. For example, the user may wear the garments 100, 700 during certain activities such as mixed martial arts, boxing, football or any other activity where the user is susceptible or vulnerable to impact to the user's genital area. The exterior waistband portion 704 of the garment 700 may substantially align with the waistband 112 of the garment 100 and the short member 702 of the garment 700 may substantially align with the short member 110 of the garment 100.

The short member 702 may be formed from one or more pieces of fabric or material to include a front section 708, a rear section 710, a first side section 712, a second side section 714 and an inseam section 716. The front section 708 and the rear section 710 may connect to respective side sections 712, 714 and inseam section 716 by stitching or any other suitable manner. The front section 708, the rear section 710, the first side section 712 and the inseam section 716 cooperate to form a first leg portion 718 of the short member 702. The front section 708, the rear section 710, the second side section 714 and the inseam section 716 cooperate to form a second leg portion 720 of the short member 702.

In an example embodiment, the front, rear or side sections 708, 710, 712, 714 may include one or more pockets 722. Each pocket 722 may include a closure member 724, such as a zipper or any other suitable fastener, to releasably close the pocket 722. In an example embodiment, the pocket 722 is formed from a water-resistant or waterproof material and shaped to hold a mouth guard, a wallet, keys or any other suitable personal possession of the user.

The fabric or material which forms the short member 702 may include natural fibers such as cotton, linen or wool, synthetic fibers such as polyester, spandex or nylon, or various blends of natural and synthetic fibers such as cotton and polyester or spandex and nylon. It should be appreciated that the short member 702 could be made from any suitable material wearable by a user. For example, the front section 708 and the rear section 710 may be formed from a first fabric or material, such as a resilient material, and the side sections 712, 714 and the inseam section 716 may be formed from a second fabric or material, such as an elastic material. In an example embodiment, the resilient material may be a non-elastic material, a water-resistant material, a waterproof material, a fire-resistant material, a flameproof material, a wear-resistant material, a wearproof material, a tear-resistant material, or a tearproof material. The fabric or material which forms the short member 702 may include a specific texture, such as a plurality of protrusions extending therefrom.

In an example embodiment, the exterior waistband portion 704 includes a channel or opening 730 which extends through an inner portion thereof. The channel 730 is configured to receive a longitudinally extending closure member 732, such as a drawstring. The closure member 732 has a first end 734 and a second end 736. The first end 734 of the closure member 732 exits the inner portion of the exterior waistband portion 704 through an aperture or slot 738. The second end 736 of the closure member 732 exits the inner portion of the exterior waistband portion 704 through an aperture or slot 740. The apertures 738, 740 may be positioned at a front portion of the exterior waistband portion 704 to enable a user to pull the first and second ends 734, 736 in opposite directions to tighten the closure member 732 about the user's waist or trunk.

In an example embodiment, the exterior waistband portion 704 includes an upwardly extending section 744 at the front portion 742 thereof. The upwardly extending section 744 is configured to move, such as by folding, relative to the exterior waistband portion 704. The upwardly extending section 744 includes a first fastener 746 which connects to the upwardly extending section 744 by stitching or any other suitable manner. The exterior waistband portion 704 includes a second fastener 748 which connects to the exterior waistband portion 704 by stitching or any other suitable manner. The second fastener 748 is configured to mate or cooperate with the first fastener 746 when the upwardly extending section 744 is moved or folded into contact the exterior waistband portion 704. In an example embodiment, after the user tightens the closure member 732 by pulling the first and second ends 734, 736 in opposite directions, the user may move the upwardly extending section 744 into contact the exterior waistband portion 704 to conceal the first and second ends 734, 736.

The first end 734 of the closure member 732 may include a fastener 750 which connects to the first end 734 by stitching or any other suitable manner. The second end 736 of the closure member 732 may include a fastener 752 which connects to the second end 736 by stitching or any other suitable manner. Fasteners 750, 752 may be configured to mate or cooperate with the fastener 748 positioned along the exterior waistband portion 704. In an example embodiment, the fasteners 750, 752 are configured to mate with the fastener 748 to hold the first and second ends 734, 736 in an adjustable position desired by the user.

Figure 20:
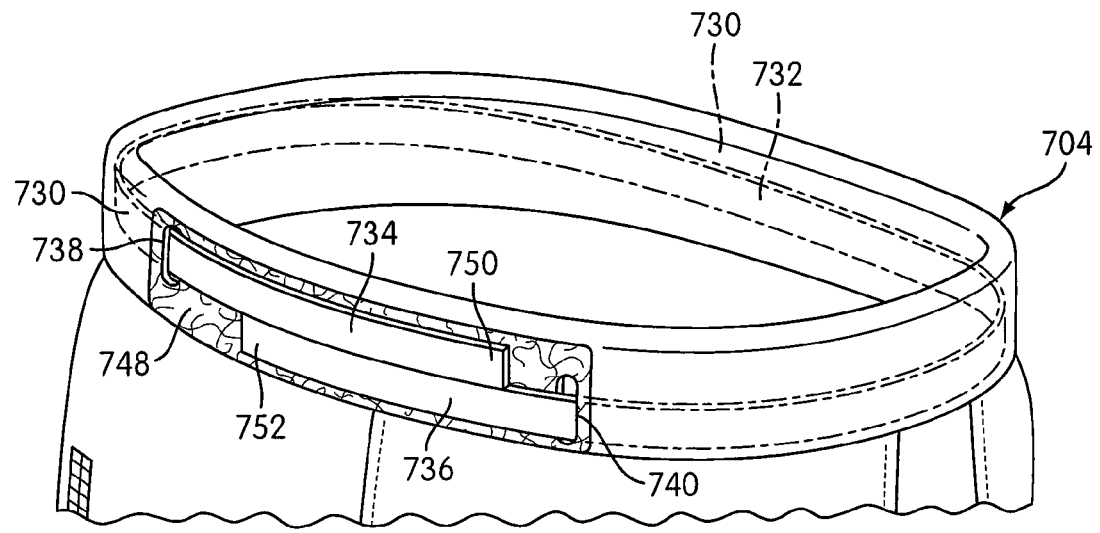
FIG. 20 illustrates a partial front perspective view of the example embodiment shown in FIG. 18.
Figure 21:
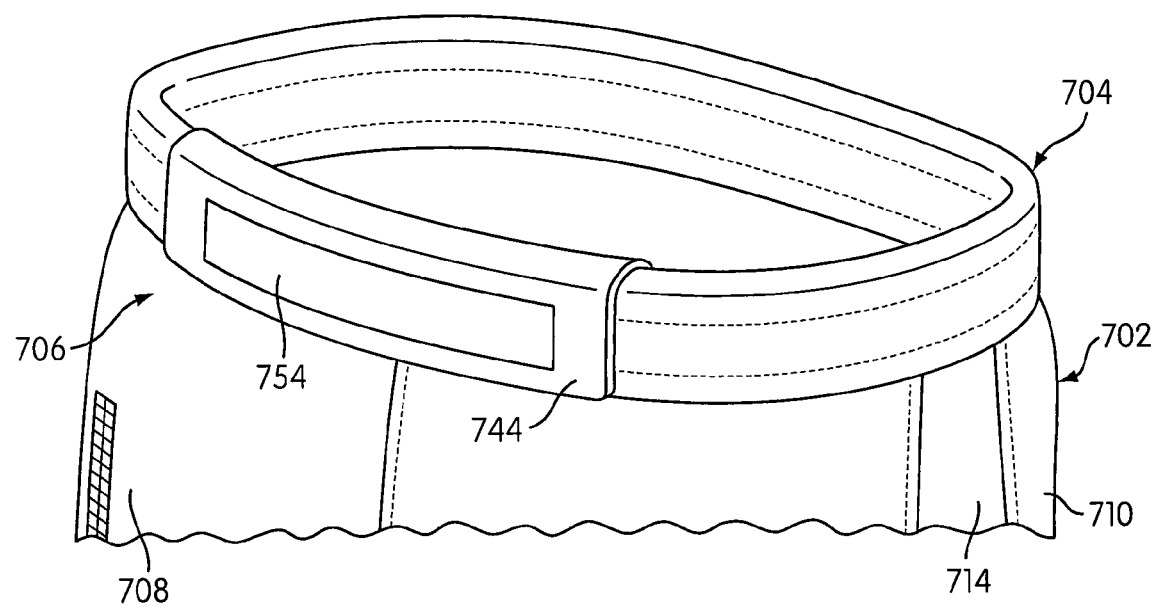
FIG. 21 illustrates a partial front perspective view of the example embodiment shown in FIG. 18.

In an example embodiment, after the user tightens the closure member 732 by pulling the first and second ends 734, 736 in opposite directions, the first end 734 of the closure member 732 may overlap with the second end 736 of the closure member 732 before the user moves the upwardly extending section 744 into contact the exterior waistband portion 704 to conceal the first and second ends 734, 736. For example, as illustrated in FIG. 20, the slots 738, 740 may be offset from one another so that the first end 734 and the second end 736 extend through the channel 730 and exit the slots 738, 740 with an offset relationship to one another. In an example embodiment, the first end 734 of the closure member 732 may coextend with, extend adjacent to, or abut with the second end 736 of the closure member 732 before the user moves the upwardly extending section 744 into contact the exterior waistband portion 704 to conceal the first and second ends 734, 736.

The fastening system 706 may include the closure member 732 and the fasteners 746, 748, 750, 752. In an example embodiment, the user operates the fastening system 706 by pulling the first and second ends 734, 736 in opposite directions. By pulling the first and second ends 734, 736 in opposite directions, the user causes the closure member 732 to tighten around that user's waist or trunk. The fasteners 748, 750, 752 enable the user to secure the first and second ends 734, 736 to the exterior waistband portion 704 in the tightened position desired by the user. After tightening the fastening system 706, the user moves the upwardly extending section 744 into contact the exterior waistband portion 704 to conceal the first and second ends 734, 736.

In an example embodiment, the fastener 746 of the upwardly extending section 744, the fastener 750 of the first end 734 and the fastener 752 of the second end 736 each includes a hook type fastener and the fastener 748 positioned along the exterior waistband portion 704 includes a loop type fastener. The fastener 746 of the upwardly extending section 744, the fastener 750 of the first end 734 and the fastener 752 of the second end 736 each may include a loop type fastener and the fastener 748 positioned along the exterior waistband portion 704 may include a hook type fastener. It should be appreciated that the fasteners 746, 748, 750, 752 may be a variety of suitable fasteners, such as snaps, buttons, zippers or other suitable separable fasteners.

In an example embodiment, the upwardly extending section 744 of the exterior waistband portion 704 or any other portion of the exterior waistband portion 704 may be configured to display branding or marketing information, such as an advertisement or sponsorship. For example, the branding or marketing information may be attached to, printed on, stitched to, or otherwise coupled with a branding area 754 of the upwardly extending section 744. When the user moves or folds the upwardly extending section 744 into contact the exterior waistband portion 704, as described above, the branding or marketing information displayed by the branding area 754 is visible. The branding area 754 may be positioned at any position on the short member 702 (e.g., the front section 708, the rear section 710, the first side section 712, the second side section 714 or the inseam section 716) or the exterior waistband portion 704 where the branding or marketing information of the branding area 754 may be visible.

Figure 22:
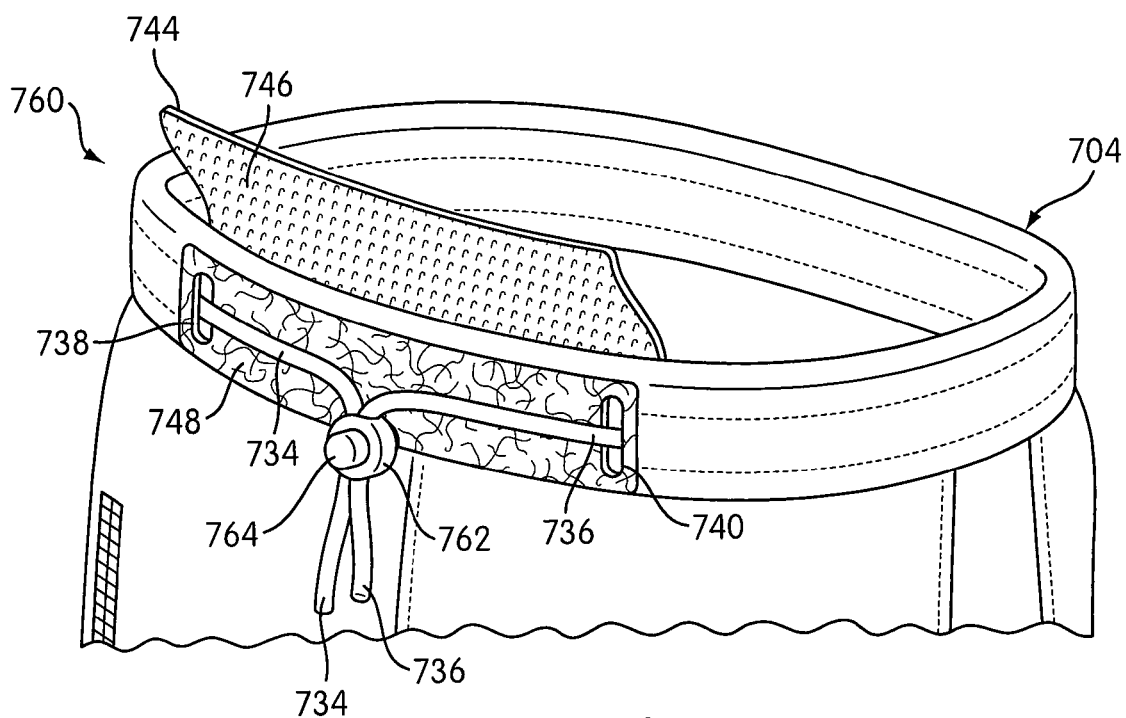
FIG. 22 illustrates a partial front perspective view of an example embodiment of a fastening system on an example embodiment of an outer garment.

Referring now to FIG. 22, an example embodiment of a fastening system 760 is illustrated. The fastening system 760 may be used with the exterior waistband portion 704 and closure member 732 described above. The fastening system 760 may include a fastener or connector 762 that releasably secures the first and second ends 734, 736 of the closure member 732. The fastener 762 may engage the first and second ends 734, 736 to maintain the ends 734, 736 in a preferred position. The fastener 762 may be movable to different positions along the first and second ends 734, 736 to adjustably tighten the closure member 732 about the user's waist or trunk.

In an example embodiment, the fastener 762 includes an actuator 764, such as a button, which may be actuated to enable movement of the fastener 762. The actuator 764 may be movable between a lock position, wherein the ends 734, 736 are held in a preferred position relative to the fastener 762 and an unlock position, wherein the ends 734, 736 may be moved relative to the fastener 762.

Figure 23A:
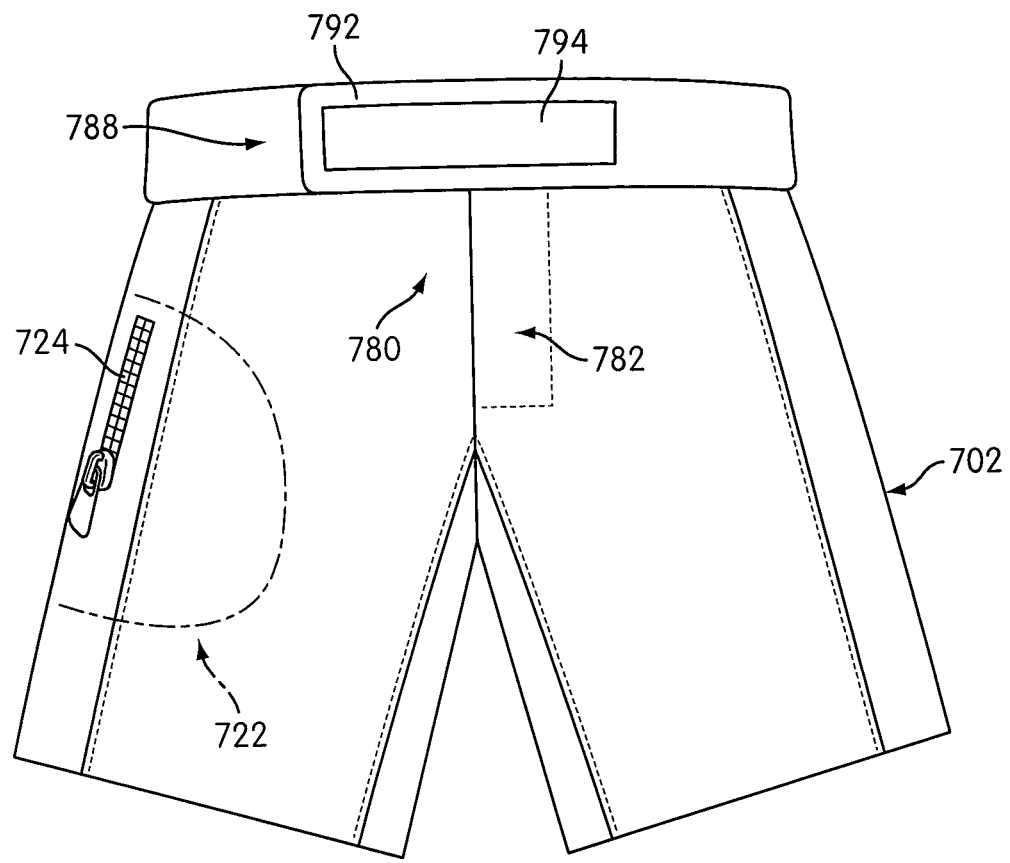
FIG. 23A illustrates a front view of an example embodiment of a fastening system on an example embodiment of an outer garment.
Figure 23B:
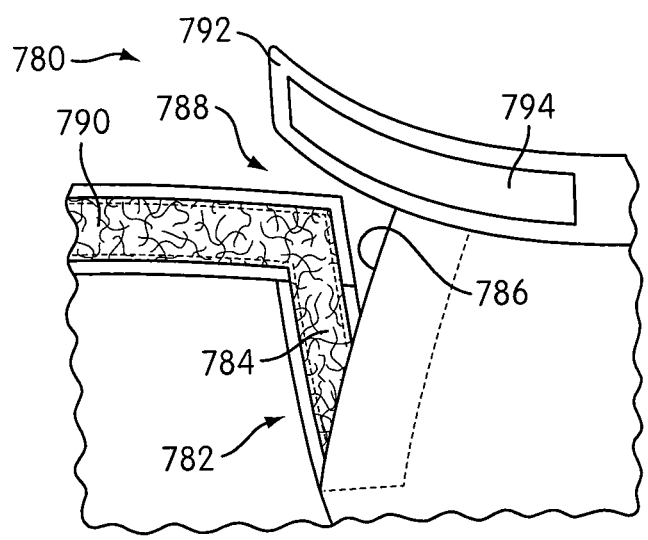
FIG. 23B illustrates a partial front view of the example embodiment shown in FIG. 23A.
Figure 24:
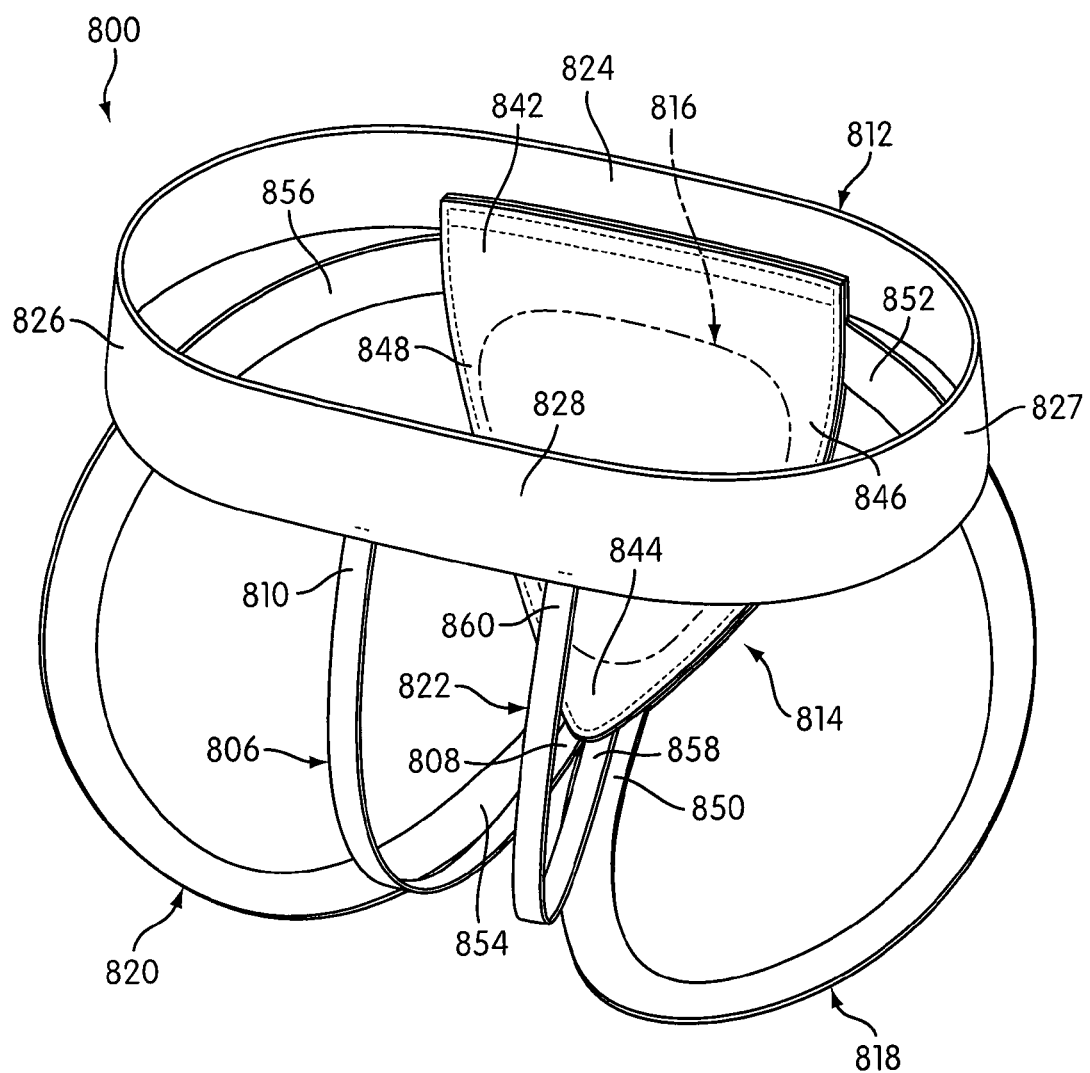
FIG. 24 illustrates a rear perspective view of an example embodiment of a garment for use with a protective cup.
Figure 25:
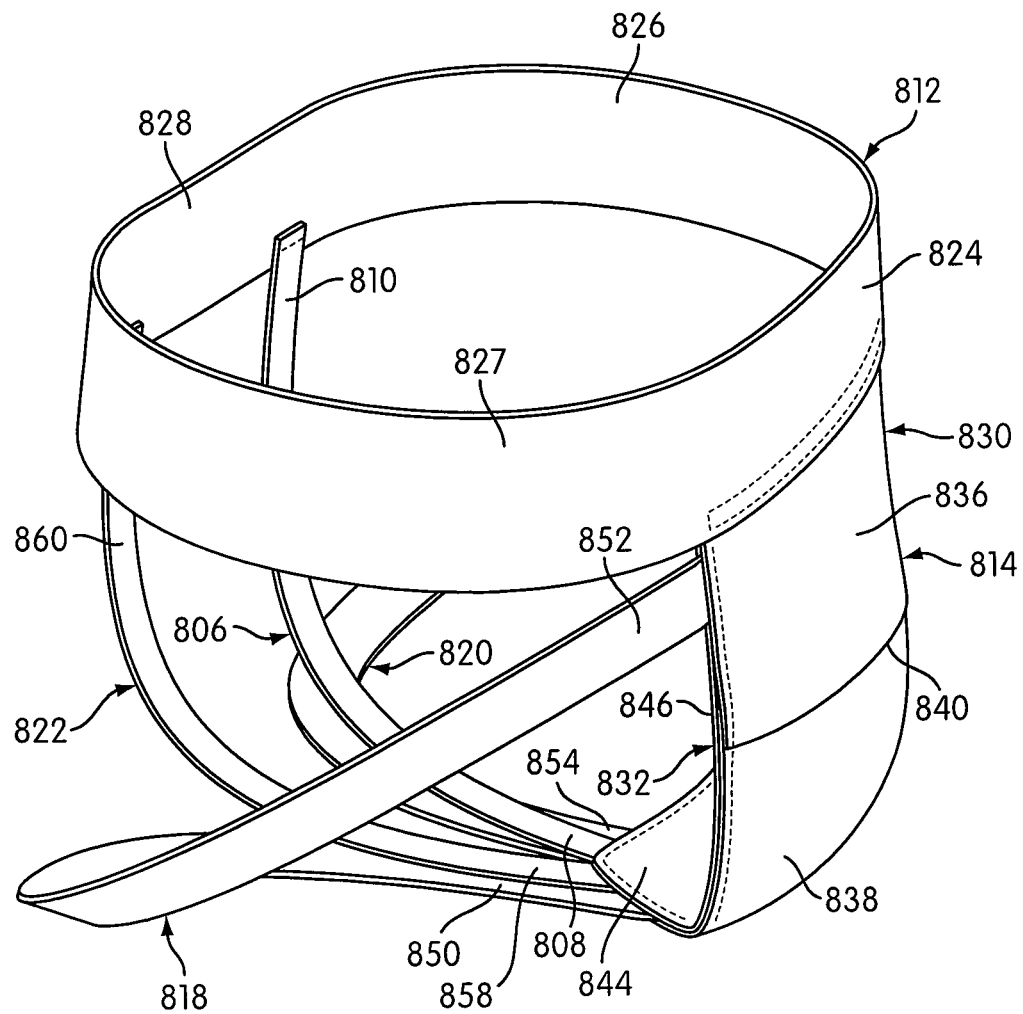
FIG. 25 illustrates a side perspective view of the example embodiment shown in FIG. 24.

Referring now to FIGS. 23A and 23B, an example embodiment of a fastening system 780 is illustrated. The fastening system 780 may connect to the front section 708 of the short member 702 described above. The fastening system 780 may include a fly fastener or connector 782 that releasably secures a first fly portion 784 of the short member 702 to a second fly portion 786 of the short member 702. The fastening system 780 may also include an adjustable waistband fastener or connector 788 that releasably secures a first waistband portion 790 to a second waistband portion 792. The adjustable waistband fastener 788 may be a variety of suitable fasteners, such as snaps, buttons, zippers, or any other suitable separable fasteners, such as hook and loop type fasteners. It should be appreciated that the adjustable waistband fastener 788 may be positioned such that the fastening system 780 connects to the rear section 710, the first side section 712 or a second side section 714 of the short member 702 described above.

A branding area 794 may be positioned adjacent to the waistband fastener 788. In an example embodiment, the branding area 794 connects to the waistband portion 792 with stitching or any other suitable connection. The branding area 794 may include branding or marketing information similar to the branding area 754 described above with respect to FIGS. 18 to 21.

Referring now to FIGS. 24, 25, 26A and 26B, an example embodiment of a garment 800, such as a jock or an athletic supporter, is illustrated. The garment 800 includes an annular support member 812 that encircles a user's waist and is commonly referred to as a waistband. The waistband 812 may connect or attach to a protective cup support 814. The protective cup support 814 is configured to support, hold or otherwise secure a protective cup 816 relative to a user's body. For example, the protective cup 816 may cover or encapsulate the user's genitals. The garment 800 includes a first support member 818, a second support member 820, a third support member 822 and a fourth support member 806 which cooperate with the waistband 812 to secure the protective cup support 814 relative to the user.

In an example embodiment, the waistband 812 has a front region 824, side regions 826, 827 and a rear region 828. The side regions 826, 827 separate the front region 824 from the rear region 828. For example, the waistband 812 may include an annular band of longitudinally elastic material which generally conforms to the waist of a user or person wearing the garment 800. The waistband 812 may include a fabric covering coextensive with and stitched to the elastic material.

In an example embodiment, the waistband 812 includes a suitably resilient or elastic material including natural fibers such as cotton, linen or wool, synthetic fibers such as polyester, spandex or nylon, or various blends of natural and synthetic fibers such as cotton and polyester or spandex and nylon. The resilient or elastic material may include a fabric having any suitable weave or pattern. It should be appreciated that the waistband 812 may be formed from a non-elastic material, such as leather, or may be used in combination with a drawstring, a belt or any other suitable closure member to maintain the garment 800 in place on the waist of the user. In an example embodiment, the waistband 812 may include a fastening system having one or more closure members which maintain the garment 800 in position relative to the user's waist.

In an example embodiment, the protective cup support 814 includes a front panel 830 which may connect to a rear panel 832 by stitching or any other suitable manner. The front panel 830 and the rear panel 832 are connected to, and cooperate with, one another to form an interior space or pocket 834. The interior space 834 is configured to receive the protective cup 816.

In an example embodiment, the front panel 830 includes a first portion 836 which overlaps a second portion 838 by a designated amount (e.g., about one inch, about two and one-half centimeters or any other suitable amount). The first portion 836 is separable from the second portion 838 to form an aperture or slot 840 which provides access to the interior space 834. As illustrated, the aperture 840 has a width that is sized to accommodate a width of the protective cup 816 such that the protective cup 816 may be inserted through the aperture 840 and received by the interior space 834.

It should be appreciated that the aperture 840 may be formed by the rear panel 832 of the protective cup support 814, rather than the front panel 830 of the protective cup support 814. For example, the rear panel 832 may include overlapping portions which cooperate to define an aperture having access to the interior space 834. In this example, the user may access the interior space 834 (e.g., to position the protective cup 816) through the aperture on the rear panel 832 of the protective cup support 814.

In an example embodiment, the front panel 830 and the rear panel 832 may be connected together to form an upper area or portion 842, a lower area or portion 844, a first side area or portion 846 and a second side area or portion 848. The upper portion 842 connects to the front region 824 of the waistband. The upper portion 842 may attach or connect to the front region 824 of the waistband 12 by stitching, or by fabric portions integral to the waistband 812. The lower portion 844 opposes the upper portion 842 along a vertical axis. The first side portion 846 and the second side portion 848 extend between the upper portion 842 and the lower portion 844. In an example embodiment, the first and second side portions 846, 848 extend from the upper portion 842, longitudinally oppose one another, and taper or narrow at the lower portion 844.

It should be appreciated that the protective cup support 814 may be sized and shaped to substantially conform to the protective cup 816. In an example embodiment, the protective cup support 814 is sized to accommodate the protective cup 816 and to reduce the ability or likelihood of the cup 816 shifting or moving within the interior space 834 of the protective cup support 814. For example, when the protective cup 816 is received by the interior space 834, the protective cup support 814 is configured such that the rear panel 832 supports a rear portion of the protective cup 816, the first portion 836 supports an upper, front portion of the protective cup 816, the second portion 838 supports a lower, front portion of the protective cup 816, and the waistband 812, the front panel 830 and the rear panel 832 support an upper portion of the protective cup 816.

In an example embodiment, the protective cup support 814 includes a protective cup receiving opening formed between the front panel 830 and the rear panel 832 to define the interior space 834 instead of the aperture 840 formed by overlapping portions 836, 838 of the front panel 830. The protective cup support 814 may include a closure member to close the protective cup receiving opening (e.g., to fasten the front panel to the rear panel), such as a snap, a button, a zipper or any other suitable separable fasteners, such as hook and loop type fasteners.

The protective cup support 814 may include a suitably resilient or elastic material including natural fibers such as cotton, linen or wool, synthetic fibers such as polyester, spandex or nylon, or various blends of natural and synthetic fibers such as cotton and polyester or spandex and nylon. It should be appreciated that the protective cup support 814 could be made from any suitable material adapted to maintain the position of the protective cup 816 relative to the user's body when worn by that user.

In an example embodiment, the first support member 818 connects between the lower portion 844 and the first side portion 846 of the protective cup support 814. The first support member 818 includes a first end 850 which connects to the lower portion 844 of the protective cup support 814, and a second end 852 which connects to the first side portion 846 of the protective cup support 814. The first support member 818 is adapted to maintain the lower portion 844 and the side portion 846 of the protective cup support 814 and the protective cup 816 in a preferred position relative to the user's body. In an example embodiment, the first support member 818 stabilizes the protective cup support 814 and the protective cup 816 in lateral or side-to-side directions when the garment 800 is worn by the user.

The second support member 820 connects between the lower portion 844 and the second side portion 848 of the protective cup support 814. The second support member 820 includes a first end 854 which connects to the lower portion 84 of the protective cup support 814, and a second end 856 which connects to the second side portion 848 of the protective cup support 814. The second support member 820 maintains the lower portion 844 and the side portion 848 of the protective cup support 814 and the protective cup 816 in a preferred position relative to the user's body. In an example embodiment, the second support member 820 stabilizes the protective cup support 814 and the protective cup 816 in lateral or side-to-side directions when the garment 800 is worn by the user.

The third support member 822 connects between the lower portion 844 of the protective cup support 814 and the waistband 812. The third support member 822 includes a first end 858 which connects to the lower portion 844 of the protective cup support 814, and a second end 860 which connects to the rear portion 828 of the waistband 812. The third support member 822 maintains the lower portion 844 of the protective cup support 814 and the protective cup 816 in a preferred position relative to the user's body. In an example embodiment, the third support member 822 stabilizes the protective cup support 814 and the protective cup 816 in forward, backward and vertical directions when the garment 800 is worn by the user.

The fourth support member 806 connects between the lower portion 844 of the protective cup support 814 and the waistband 812. The fourth support member 806 includes a first end 808 which connects to the lower portion 844 of the protective cup support 814, and a second end 810 which connects to the rear portion 828 of the waistband 812. The fourth support member 806 maintains the lower portion 844 of the protective cup support 814 and the protective cup 816 in a preferred position relative to the user's body. In an example embodiment, the fourth support member 806 stabilizes the protective cup support 814 and the protective cup 816 in forward, backward and vertical directions when the garment 10 is worn by the user.

In an example embodiment, the third support member 822 connects to the rear portion 828 of the waistband 812 at a first connection point and the fourth support member 806 connects to the rear portion 828 of the waistband 812 at a second connection point. The first and second connection points may be spaced from one another by a designated distance, e.g., about one-half inch (or about one and one-quarter centimeters), about one inch (or about two and one-half centimeters), about six inches (or about fifteen centimeters), or any other suitable distance. It should be appreciated that the first and second connection points may be spaced from one another by any suitable distance. For example, the third and fourth support members 822, 806 may connect to the rear portion 828 of the waistband 812 such that the first and second connection points abut one another. If the first and second connection points abut one another (i.e., with no space therebetween), the third and fourth support members 822, 806 extend substantially adjacent to one another between the waistband 812 and the protective cup support 814.

The first end 850 of the first support member 818, the first end 854 of the second support member 820, the first end 858 of the third support member 822, and the first end 808 of the fourth support member 806 may each connect to the lower portion 844 of the protective cup support 814 at a same location or at a substantially same location. The first end 850 of the first support member 818, the first end 854 of the second support member 820, the first end 858 of the third support member 822, and the first end 808 of the fourth support member 806 may each connect to the lower portion 844 of the protective cup support 814 at different locations (e.g., for the ends 850, 854, 858, 808 to have a spaced relationship with one another at the lower portion 844).

It should be appreciated that the first end 850 of the first support member 818, the first end 854 of the second support member 820, the ends 858, 860 of the third support member 822, and the ends 808, 810 of the fourth support member 806 may include an elastic component having sufficient elastic tension to maintain the lower portion 844 of the protective cup support 814 and the protective cup 816 in a preferred position and reduce movement of the support 814 and the cup 816 in forward, backward, lateral and vertical directions. The ends 852, 856 of the first and second support members 818, 820 may include an elastic component having sufficient elastic tension to maintain the side portions 846, 848 of the protective cup support 814 and the protective cup 816 in a preferred position and reduce movement of the support 814 and the cup 816 in lateral or side-to-side directions.

In an example embodiment, the first, second, third and fourth support members 818, 820, 822, 806 may each include an elongated component or strap made from a suitably resilient or elastic material. It should be appreciated that the suitably resilient or elastic material may include natural fibers such as cotton, linen or wool, synthetic fibers such as polyester, spandex or nylon, or various blends of natural and synthetic fibers such as cotton and polyester or spandex and nylon. The resilient or elastic material may include a fabric having any suitable weave or pattern. The first, second, third and fourth support members 818, 820, 822, 806 may each be formed from a non-elastic material, such as leather or any other suitable non-elastic material. It should also be appreciated that the first, second, third and fourth support members 818, 820, 822, 806 may be made from any suitable material adapted to maintain the position of the protective cup 816 relative to the user's body when worn by that user.

It should be appreciated that the waistband 812, the protective cup support 814, the first support member 818, the second support member 820, the third support member 822 and the fourth support member 806 may be made from any stretchable material such as elastic material or extensible material. When elongated in one or more dimensions, elastic materials may exert a force tending to move the material at least partially to its original dimensions and extensible materials may remain in the elongated dimensions.

Figure 26A:
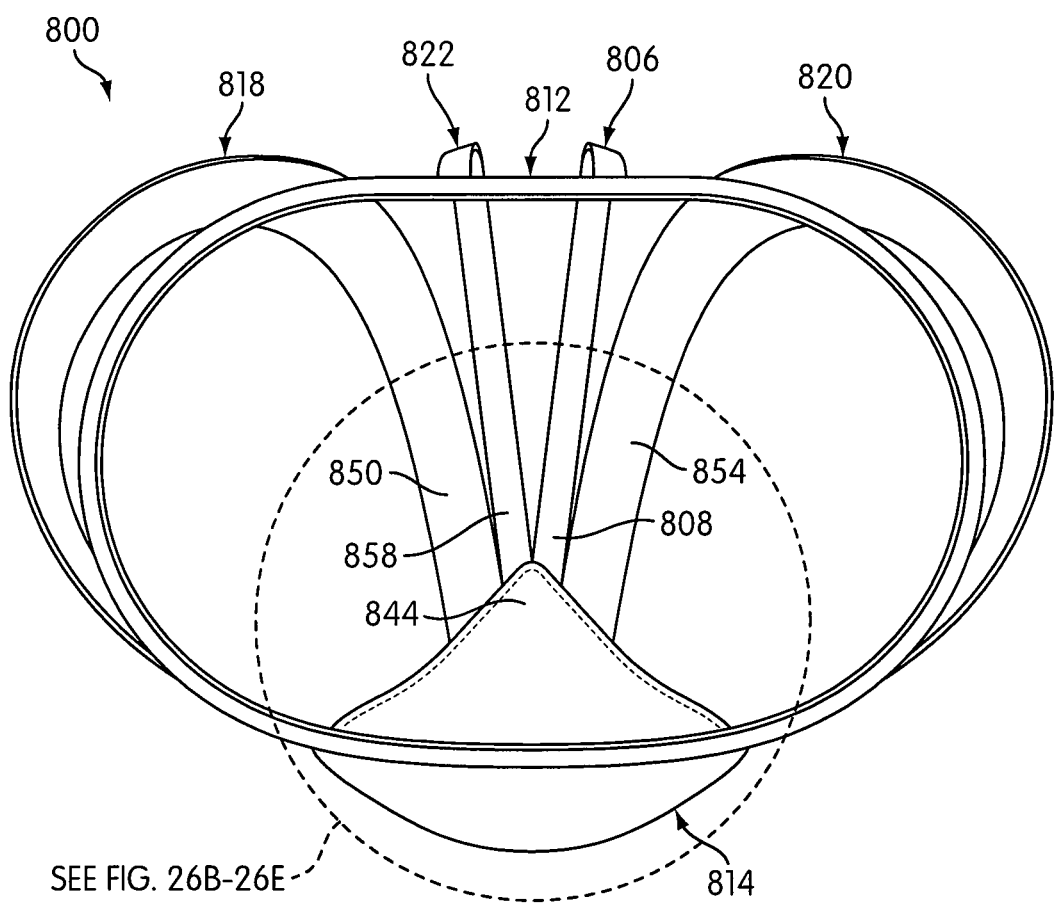
FIG. 26A illustrates a top view of the example embodiment shown in FIG. 24, wherein first, second, third and fourth support members connect to a protective cup support.
Figure 26B:
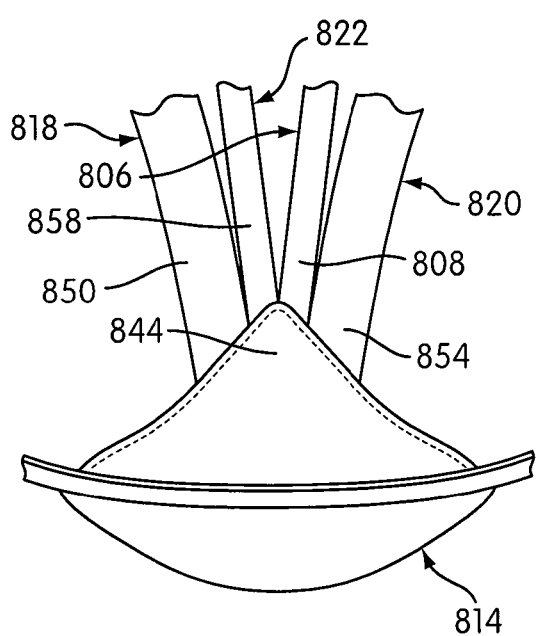
FIG. 26B illustrates an enlarged view of the example embodiment shown in FIG. 26A, wherein first, second, third and fourth support members connect to a protective cup support.

Referring now to FIG. 26B, the first, second, third and fourth support members 818, 820, 822, 806 may connect to the lower portion 844 of the protective cup support 814. The first end 850 of the first support member 818 may connect to the lower portion 844 of the protective cup support 814. The first end 854 of the second support member 820 may connect to the lower portion 844 of the protective cup support 814. The first end 858 of the third support member 822 may connect to the lower portion 844 of the protective cup support 814 through stitching or any other suitable manner. The first end 858 of the third support member 822 may be spaced from the first end 850 of the first support member 818 at the lower portion 844. The first end 808 of the fourth support member 806 may connect to the lower portion 844 of the protective cup support 814 through stitching or any other suitable manner. The first end 808 of the fourth support member 806 may be spaced from the first end 854 of the second support member 820 at the lower portion 844.

Figure 26C:
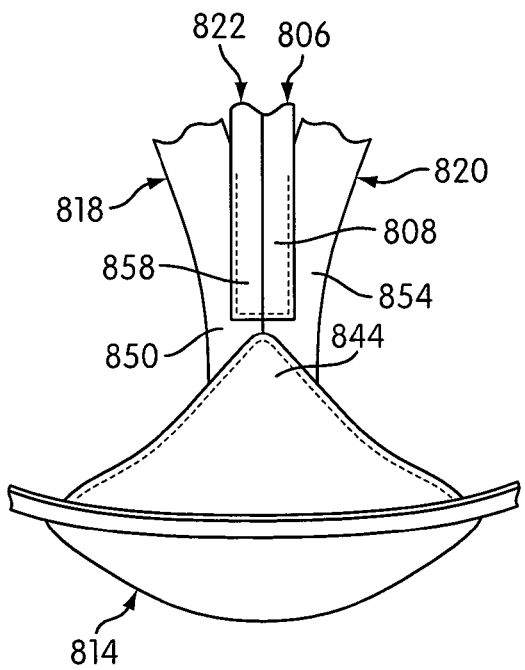
FIG. 26C illustrates an enlarged view of an example embodiment of a garment for use with a protective cup, wherein first, second, third and fourth support members connect to a protective cup support.

Referring now to FIG. 26C, an example embodiment of the first, second, third and fourth support members 818, 820, 822, 806 is illustrated. The first end 850 of the first support member 818 may connect to the lower portion 844 of the protective cup support 814. The first end 854 of the second support member 820 may connect to the lower portion 844 of the protective cup support 814. The first end 858 of the third support member 822 may connect to the first end 850 of the first support member 818, the lower portion 844 of the protective cup support 814, or both. The first end 808 of the fourth support member 806 may connect to the first end 854 of the second support member 820, the lower portion 844 of the protective cup support 814, or both. The first ends 858, 808 of the third and fourth support members 822, 806 may be connected to one another.

Figure 26D:
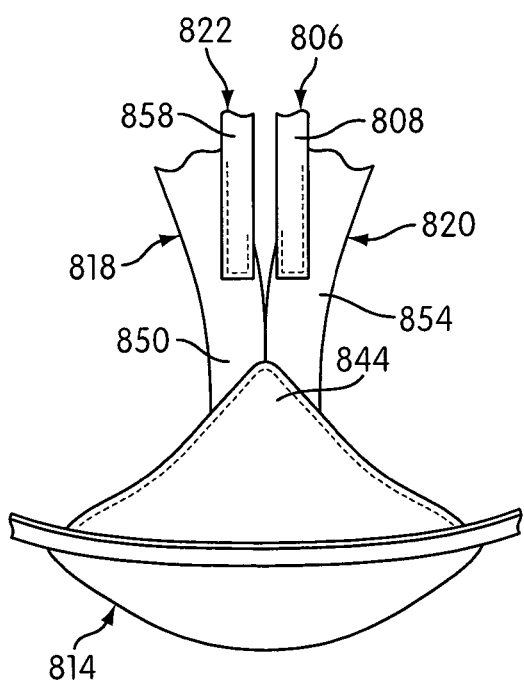
FIG. 26D illustrates an enlarged view of an example embodiment of a garment for use with a protective cup, wherein first, second, third and fourth support members connect to a protective cup support.

Referring now to FIG. 26D, an example embodiment of the first, second, third and fourth support members 818, 820, 822, 806 is illustrated. The first end 850 of the first support member 818 may connect to the lower portion 844 of the protective cup support 814. The first end 854 of the second support member 820 may connect to the lower portion 844 of the protective cup support 814. The first end 858 of the third support member 822 may connect to the first end 850 of the first support member 818. The first end 858 of the third support member 822 may connect to either a top or bottom side of the first end 850 of the first support member 818. The first end 808 of the fourth support member 806 may connect to the first end 854 of the second support member 820. The first end 808 of the fourth support member 806 may connect to either a top or bottom side of the first end 854 of the second support member 820. The first ends 858, 808 of the third and fourth support members 822, 806 may be spaced apart from one another by a designated distance. The distance between the first ends 858, 808 of the third and fourth support members 822, 806 may be the same or different than the distance between the second ends 860, 810 of the third and fourth support members 822, 806.

Figure 26E:
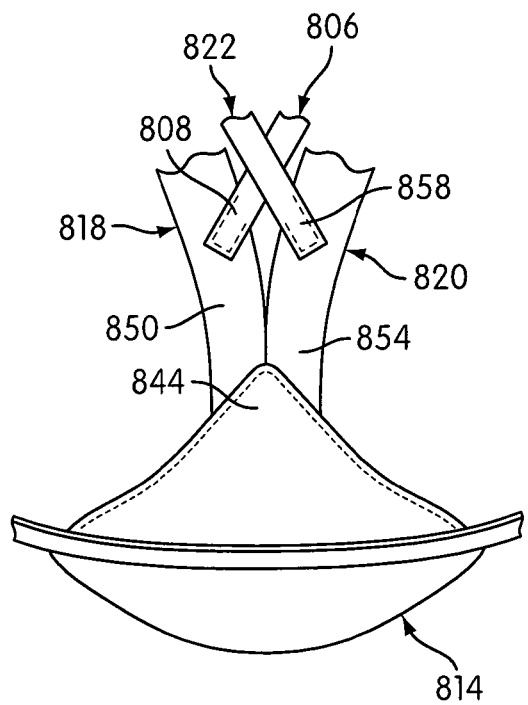
FIG. 26E illustrates an enlarged view of an example embodiment of a garment for use with a protective cup, wherein first, second, third and fourth support members connect to a protective cup support.

Referring now to FIG. 26E, an example embodiment of the first, second, third and fourth support members 818, 820, 822, 806 is illustrated. The first end 50 of the first support member 18 connects to the lower portion 84 of the protective cup support 14. The first end 54 of the second support member 20 connects to the lower portion 84 of the protective cup support 14. The first end 858 of the third support member 822 may connect to the first end 854 of the second support member 820. The first end 858 of the third support member 822 may connect to either a top or bottom side of the first end 854 of the second support member 820. The first end 808 of the fourth support member 806 may connect to the first end 850 of the first support member 818. The first end 808 of the fourth support member 806 may connect to either a top or bottom side of the first end 850 of the first support member 820.

In an example embodiment, the first end 858 of the third support member 822 may connect to the lower portion 844 of the protective cup support 814 via at least one of (i) the first end 850 of the first support member 818, (ii) the first end 854 of the second support member 820, and (iii) the first end 850 of the first support member 818 and the first end 854 of the second support member 820. In an example embodiment, the first end 808 of the fourth support member 806 may connect to the lower portion 844 of the protective cup support 814 via at least one of (i) the first end 850 of the first support member 818, (ii) the first end 854 of the second support member 820, and (iii) the first end 850 of the first support member 818 and the first end 854 of the second support member 820.

In an example embodiment, each of the first, second, third and fourth support members 818, 820, 822, 806 may have at least one end directly connected to the protective cup 816. The first ends 850, 854, 858, 808 of the first, second, third and fourth support members 818, 820, 822, 806 each may connect to a lower portion of the protective cup 816. The second end 852 of the first support member 818 may connect to a first side portion of the protective cup 816. The second end 856 of the second support member 820 may connect to a second side portion of the protective cup 816.

In an example embodiment, the first ends 850, 854, 858 may connect to the protective cup 816 through the same opening or through different openings formed in the protective cup 816. The second ends 852, 856 of the first and second support members 818, 820 may connect to the protective cup 816 through openings formed in, or adjacent to, the side portions of the protective cup 816. The second end 860 of the third support member 822 and the second end 810 of the fourth support member 806 may connect to the rear portion 828 of the waistband 812 by stitching or any other suitable manner.

Figure 27:
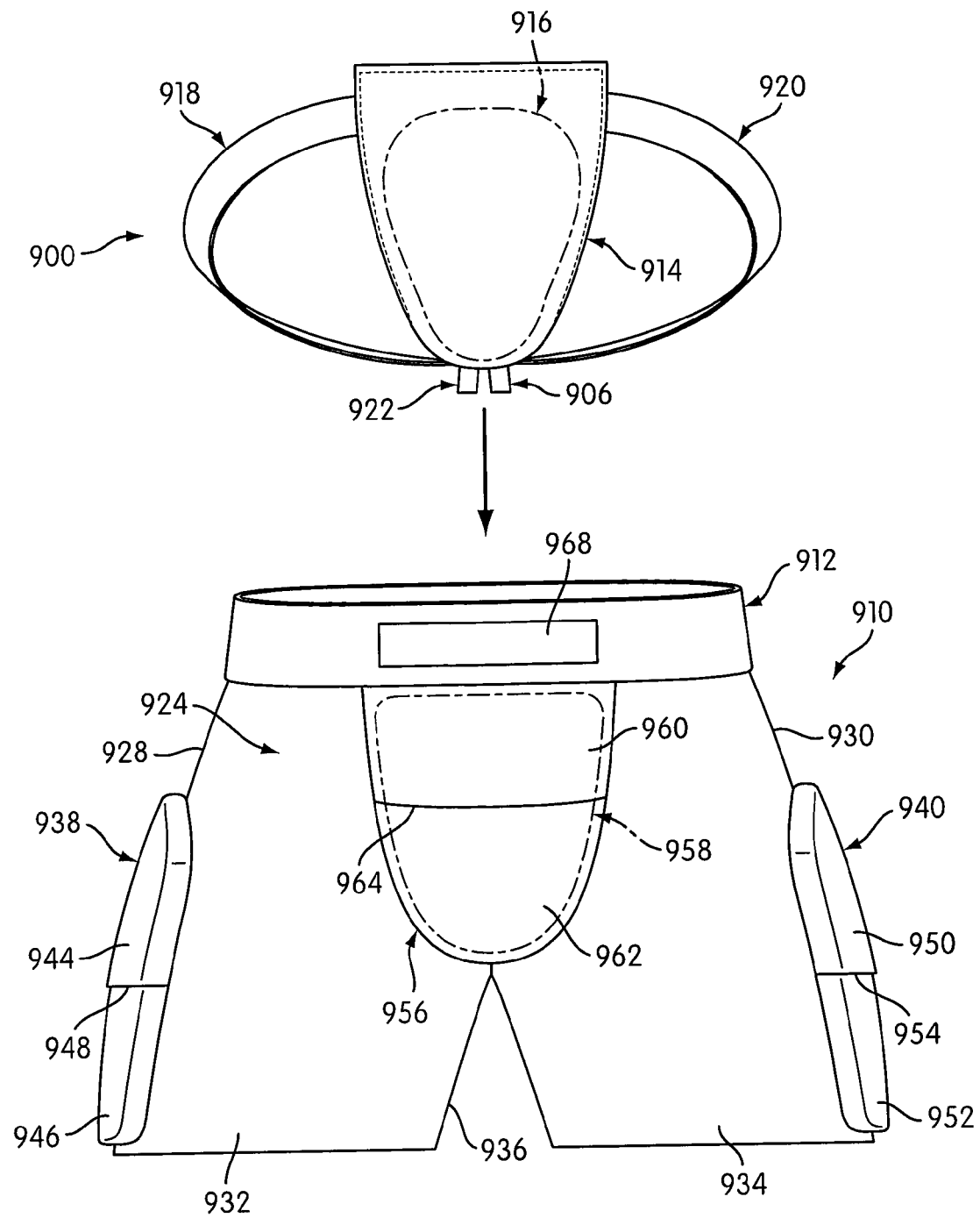
FIG. 27 illustrates an exploded view of an example embodiment of an inner garment for use with a protective cup.
Figure 28:
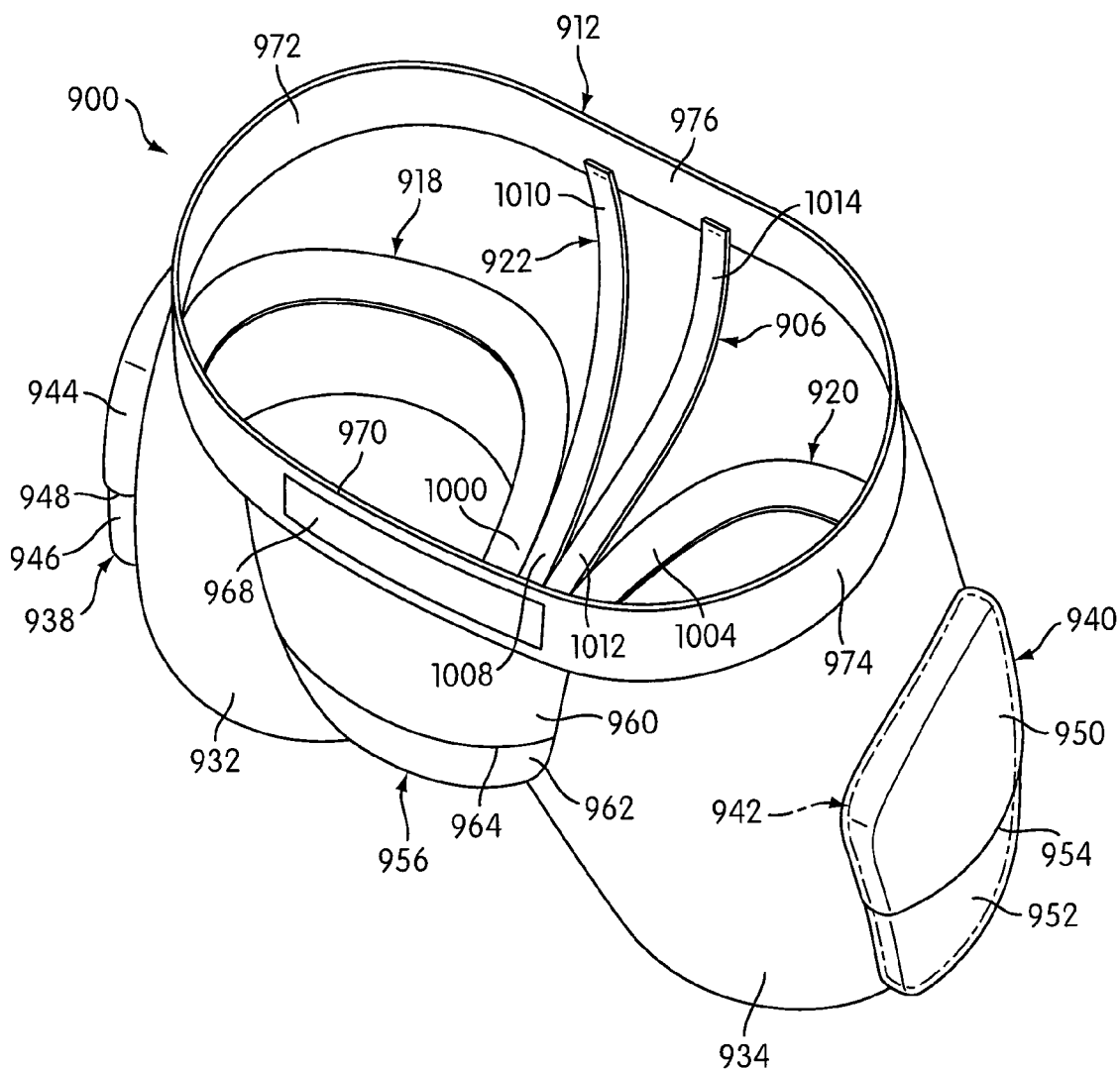
FIG. 28 illustrates a top, side perspective view of the example embodiment shown in FIG. 27.
Figure 29:
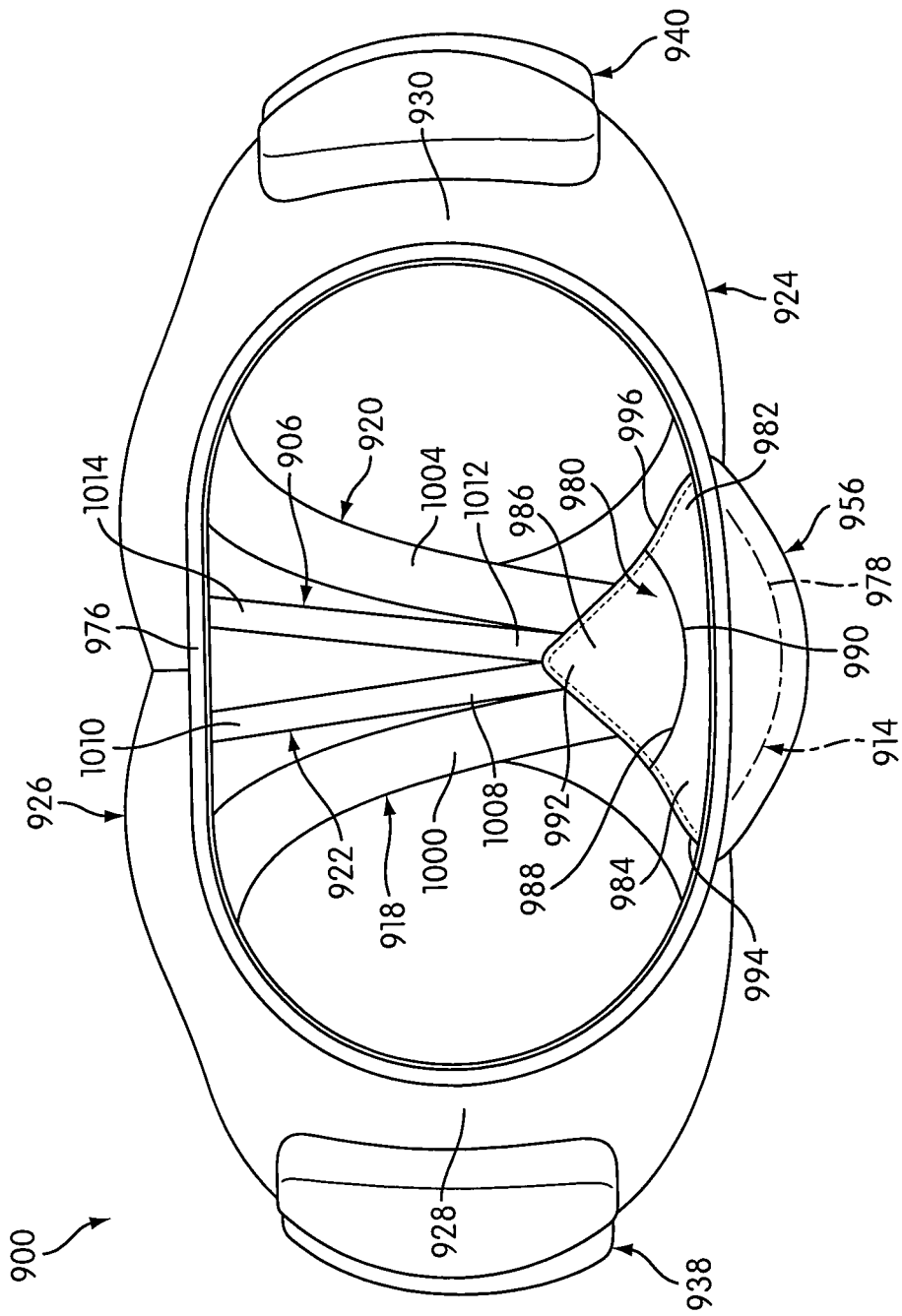
FIG. 29 illustrates a top view of the example embodiment shown in FIG. 27.

Referring now to FIGS. 27 to 29, an example embodiment of a garment 900 is illustrated. Garment 900 may be referred to as an inner garment or a compression short. The garment 900 may include a short member 910 connected to a waistband 912 by stitching, by having portions integral with the waistband 912, or by any suitable connection or fastener. The garment 900 may also include a protective cup support 914, a first support member 918, a second support member 920, a third support member 922 and a fourth support member 906.

The short member 910 may include a plurality of interior portions connected to the waistband 912, the protective cup support 914, the first support member 918, the second support member 920, the third support member 922 and the fourth support member 906 by stitching or any other suitable connection. In an example embodiment, the short member 910 includes a front portion 924, a rear portion 926 and respective side portions 928, 930 interconnecting the front portion 924 and the rear portion 926. The front portion 924, the side portion 928 and the rear portion 926 cooperate to form a first leg portion 932. The front portion 924, the side portion 930 and the rear portion 926 cooperate to form a second leg portion 934. The first and second leg portions 932, 934 are separated from one another by an inseam 936. The front portion 924, the rear portion 926, the side portions 928, 930, and the leg portions 932, 934 each have an interior surface which is configured to contact the user's body when the garment 900 is worn by the user, and an exterior surface which opposes the interior surface.

It should be appreciated that the inseam 936 may have different lengths, which enables the leg portions 932, 934 to have different lengths. In an example embodiment, the leg portions 932, 934 and the inseam 936 may be sized to form leg openings which extend to a portion of the user's leg (e.g., the user's thigh). For example, the inseam 936 may be sized so that when a user wears the garment 900, the leg portions 932, 934 extend to a portion of the user's legs above the user's knees. In another example, the inseam 936 may be sized so that when a user wears the garment 900, the leg portions 932, 934 extend to a portion of the user's legs below the user's knees. For example, when a user wears the garment 900, the inseam 936 may be sized so that the leg portions 932, 934 extend to a portion of the user's legs at or below the user's ankles.

In an example embodiment, the first leg portion 932 includes a protective pad support 938 disposed on the exterior surface thereof. The protective pad support 938 may define an interior space that is configured to receive a leg pad 942. The protective pad support 938 may include an upper exterior portion 944 which overlaps a lower exterior portion 946 by a designated amount (e.g., about one inch, about two and one-half centimeters or any other suitable amount) to define a protective pad receiving aperture 948. In an example embodiment, the lower exterior portion 946 may overlap the upper exterior portion 944 by a designated amount to define the protective pad receiving aperture 948. The upper exterior portion 944 may be separable from the lower exterior portion 946 to access the interior space of the protective pad support 938 through the protective pad receiving aperture 948. The aperture 948 may have a width that is sized to accommodate a width of the leg pad 942 such that the leg pad 942 may be inserted through the protective pad receiving aperture 948 and received by the interior space of the protective pad support 938. For example, a user may access the interior space (e.g., to position the leg pad 942) through the protective pad receiving aperture 948 of the protective pad support 938.

In an example embodiment, the second leg portion 934 includes a protective pad support 940 disposed on the exterior surface thereof. The protective pad support 940 may be substantially similar to the protective pad support 938 of the first leg portion 932. The protective pad support 940 may define an interior space that is configured to receive a leg pad 942. The protective pad support 940 may include an upper exterior portion 950 which overlaps a lower exterior portion 952 by a designated amount (e.g., about one inch, about two and one-half centimeters or any other suitable amount) to define a protective pad receiving aperture 954. In an example embodiment, the lower exterior portion 952 may overlap the upper exterior portion 950 by a designated amount to define the protective pad receiving aperture 954. The upper exterior portion 950 may be separable from the lower exterior portion 952 to access the interior space of the protective pad support 940 through the protective pad receiving aperture 954. The aperture 954 may have a width that is sized to accommodate a width of the leg pad 942 such that the leg pad 942 may be inserted through the protective pad receiving aperture 954 and received by the interior space of the protective pad support 940. For example, a user may access the interior space (e.g., to position the leg pad 942) through the protective pad receiving aperture 954 of the protective pad support 940.

The protective pad supports 938, 940 of the first and second leg portions 932, 934 may each be configured to receive separate leg pads 942. The leg pad 942 may be inserted into and removed from the protective pad supports 938, 940. The leg pad 942 may be shaped to conform to the interior space defined by each protective pad support 938, 940. The leg pad 942 may include any suitable material or padding, such as rubber, foam or any other suitable material which absorbs, disperses or reduces impact.

In an example embodiment, the front portion 924 of the short member 950 may include a protective pad support 956 disposed on the exterior surface thereof. The protective pad support 956 may be substantially similar to the protective pad supports 938, 940 of the leg portions 932, 934. The protective pad support 956 may define an interior space that is configured to receive a groin region pad 958. The protective pad support 956 may include an upper exterior portion 960 which overlaps a lower exterior portion 962 by a designated amount (e.g., about one inch, about two and one-half centimeters or any other suitable amount) to define a protective pad receiving aperture 964. In an example embodiment, the lower exterior portion 962 may overlap the upper exterior portion 960 by a designated amount to define the protective pad receiving aperture 964. The upper exterior portion 960 may be separable from the lower exterior portion 962 to access the interior space of the protective pad support 956 through the protective pad receiving aperture 964. The aperture 964 may have a width that is sized to accommodate a width of the groin region pad 958 such that the groin region pad 958 may be inserted through the protective pad receiving aperture 964 and received by the interior space of the protective pad support 956. For example, a user may access the interior space (e.g., to position the groin region pad 958) through the protective pad receiving aperture 964 of the protective pad support 956.

The protective pad support 956 is configured to receive the groin region pad 958. The groin region pad 958 may be inserted in and removed from the protective pad support 956. The groin region pad 958 may be shaped to conform to the interior space defined by the protective pad support 956. The groin region pad 958 may include any suitable material or padding, such as rubber, foam or any other suitable material which absorbs, disperses or reduces impact. The groin region pad 958 may include any suitable perforated or non-perforated material which absorbs, disperses or reduces an amount of force exerted thereon.

In an example embodiment, the leg pads 942 and/or the groin region pad 958 may include any suitable polymer which is suitable to absorb, disperse or reduce the amount of force or speed of an impact. The leg pads 942 and/or the groin region pad 958 may include a shock absorbing polymer, a vibration dampening polymer, a viscoelastic polymer or a visco polymer, such as the polymers manufactured by Action Products, Inc. of Hagerstown, Md. In an example embodiment, the leg pads 942 and/or the groin region pad 958 may include one or more cells, ribs, bumps or protrusions extending from and attached thereto. Each cell, rib, bump or protrusion may be filled with a solid, a liquid, a gas or a gel to absorb, disperse or reduce the amount of force or speed of an impact. In an example embodiment, the leg pads 942 and/or the groin region pad 958 may include rubber or foam, which may act as a crumple zone to absorb, disperse, or reduce the amount of force or speed of an impact. For example, the leg pads 942 and/or the groin region pad 958 may be any suitable foam, such as an ethylene vinyl acetate (EVA) foam or a closed cell foam (e.g., polyethylene foam, polystyrene foam, or polychloroprene foam). In an example embodiment, the leg pads 942 and/or the groin region pad 958 may be a panel of perforated or non-perforated thermoplastic material having a honeycomb core and a plurality of sheets bonded to the honeycomb core. The honeycomb core may have shock dampening characteristics to absorb, disperse, or reduce the amount of force or speed of an impact. One example of a suitable honeycomb structure is manufactured by Supracor, Inc. of San Jose, Calif.

It should be appreciated that the protective pad support 956 and the protective pad supports 938, 940 may fixedly support the groin region pad 958 and the leg pads 942, respectively. For example, the groin region pad 958 and the leg pads 942 may be stitched or enclosed in any suitable manner within the protective pad support 956 and the protective pad supports 938, 940.

In an example embodiment, the leg portions 932, 934 may include one or more protective pad supports configured to receive protective pads to protect the user's buttocks, hips, thighs, shins or knees. The protective pad supports and the protective pads for protecting the user's buttocks, hips, thighs, shins or knees may be substantially similar to the protective pad supports 938, 940, 956, the leg pads 942 and the groin region pad 958 described above.

Referring now to FIGS. 27 and 28, the waistband 912 includes a branding region 968, a front region 970, side regions 972, 974 and a rear region 976. Each of the side regions 972, 974 separate the front region 970 from the rear region 976. The front, side and rear regions 970, 972, 974, 976 of the waistband 912 may align with, and be connected to, the front, side and rear portions 924, 926, 928, 930 of the garment 900 by stitching or any other suitable connection.

In an example embodiment, the branding region 968 may be configured to display branding or marketing information, such as an advertisement or sponsorship. For example, the branding or marketing information may be attached to, printed on, stitched to, or otherwise coupled with the branding region 968 in any suitable manner. The branding region 968 may be positioned along any one, a plurality of, or each of the front region 970, the side regions 972, 974, and the rear region 976.

In an example embodiment, the protective cup support 914 includes a front panel 978 which may connect to a rear panel 980 by stitching or any other suitable manner. The front panel 978 and the rear panel 980 are connected to, and cooperate with, one another to form an interior space or pocket 982. The interior space 982 is configured to receive a protective cup 916, which may be substantially similar to the protective cup 16.

The rear panel 980 includes a first portion 984 which overlaps a second portion 986 by a designated amount (e.g., about one inch, about two and one-half centimeters or any other suitable amount). The first portion 984 is separable from the second portion 986 to form an aperture or slot 988 which provides access to the interior space 982. The aperture 988 may have a width that is sized to accommodate a width of a protective cup such that the protective cup may be inserted through the aperture 988 and received by the interior space 982. For example, a user may access the interior space 982 (e.g., to position the protective cup) through the aperture 988 on the rear panel 980 of the protective cup support 914. The protective cup support 914 may include a closure member to close the protective cup receiving aperture 988 (e.g., to fasten the first portion 984 to the second portion 986), such as a snap, a button, a zipper or any other suitable separable fasteners, such as hook and loop type fasteners.

It should be appreciated that the protective cup support 914 may be sized and shaped to substantially conform to the protective cup 916. In an example embodiment, the protective cup support 914 is sized to accommodate the protective cup 916 and to reduce the ability or likelihood of the cup 916 shifting or moving within the interior space 982 of the protective cup support 914. For example, when the protective cup 916 is received by the interior space 982, the protective cup support 914 is configured such that the rear panel 980 supports a rear portion of the protective cup 916, the first portion 984 supports an upper, front portion of the protective cup 916, the second portion 986 supports a lower, front portion of the protective cup 916, and the waistband 912, the front panel 978 and the rear panel 980 support an upper portion of the protective cup 916.

In an example embodiment, the front panel 978 and the rear panel 980 connect together to form an upper area or portion 990, a lower area or portion 992, a first side area or portion 994 and a second side area or portion 996 of the protective cup support 914. The upper portion 990 may connect to the front region 970 of the waistband 912 by stitching, by having portions integral with the waistband 912, or with any suitable connection or fastener. For example, the upper portion 990 of the front and rear panels 978, 980 may be connected to, and cooperate with, the front region 970 of the waistband to form the interior space or pocket 982. The first side portion 994 and the second side portion 996 extend between the upper portion 990 and the lower portion 992. The first and second side portions 994, 996 may extend from the upper portion 990, longitudinally oppose one another, and taper or narrow at the lower portion 992. The lower portion 992 may be suspended between the front portion 924, the rear portion 926 and the side portions 928, 930 of the garment 900.

In an example embodiment, the protective cup support 914 may be positioned between the front portion 924, the rear portion 926 and the side portions 928, 930 to substantially align with the protective pad support 956 disposed on the exterior surface of the front portion 924. The protective cup support 914 may be positioned relative to the protective pad support 956 and the groin region pad 958 so that the groin region pad 958 may absorb, disperse or reduce the amount of force or speed of an impact to the user's groin region.

In an example embodiment, the upper portion 990 connects to the front region 970 of the waistband 912 with stitching, by having portions integral with the waistband 912, or with any suitable connection or fastener. The side portions 994, 996 may each connect to the interior surface of the front portion 924 of the garment 900 with stitching, by having portions integral with the front portion 924, or with any suitable connection or fastener. The side portions 994, 996 may connect to the interior surface of the front portion 924 to maintain the protective cup support 914 and the protective cup 916 in a preferred position relative to the user's body. For example, the side portions 994, 996 may stabilize the protective cup support 914 and the protective cup 916 in lateral or side-to-side directions.

In an example embodiment, the lower portion 992 and the side portions 994, 996 each connect to the interior surface of the front portion 924 of the garment 900 with stitching, by having portions integral with the front portion 924, or with any suitable connection or fastener. The lower portion 992 and the side portions 994, 996 may connect to the interior surface of the front portion 924 to maintain the protective cup support 914 and the protective cup 916 in a preferred position relative to the user's body. For example, the lower portion 992 may stabilize the protective cup support 914 and the protective cup 916 in forward, backward and vertical directions and the side portions 994, 996 may stabilize the protective cup support 914 and the protective cup 916 in lateral or side-to-side directions.

In an example embodiment, the upper portion 990 connects to the front region 970 of the waistband 912 with stitching, by having portions integral with the waistband 912, or with any suitable connection or fastener. The lower portion 992 connects to the interior surfaces of the front and rear portions 924, 926 of the garment 900 with stitching, by having portions integral with the front portion 924, or with any suitable connection or fastener. The lower portion 992 may connect to the interior surfaces of the front and rear portions 924, 926 to maintain the protective cup support 914 and the protective cup 916 in a preferred position relative to the user's body. For example, the lower portion 992 may stabilize the protective cup support 914 and the protective cup 916 in forward, backward and vertical directions.

In an example embodiment, the first support member 918 connects between the lower portion 992 and the first side portion 994 of the protective cup support 914. The first support member 918 includes a first end 1000 which may connect to the lower portion 992 of the protective cup support 914, and a second end 1002 which may connect to the first side portion 994 of the protective cup support 914. The first support member 918 is adapted to maintain the lower portion 992 and the side portion 994 of the protective cup support 914 and the protective cup 916 in a preferred position relative to the user's body. In an example embodiment, the first support member 918 stabilizes the protective cup support 914 and the protective cup 916 in lateral or side-to-side directions when the garment 900 is worn by the user.

The second support member 920 connects between the lower portion 992 and the second side portion 996 of the protective cup support 914. The second support member 920 includes a first end 1004 which connects to the lower portion 992 of the protective cup support 914, and a second end 1006 which connects to the second side portion 996 of the protective cup support 914. The second support member 920 maintains the lower portion 992 and the side portion 996 of the protective cup support 914 and the protective cup 916 in a preferred position relative to the user's body. In an example embodiment, the second support member 920 stabilizes the protective cup support 914 and the protective cup 916 in lateral or side-to-side directions when the garment 900 is worn by the user.

The third support member 922 connects between the lower portion 992 of the protective cup support 914 and the waistband 912. The third support member 922 includes a first end 1008 which connects to the lower portion 992 of the protective cup support 914, and a second end 1010 which connects to the rear portion 976 of the waistband 912. The third support member 922 maintains the lower portion 992 of the protective cup support 914 and the protective cup 916 in a preferred position relative to the user's body. In an example embodiment, the third support member 922 stabilizes the protective cup support 914 and the protective cup 916 in forward, backward and vertical directions when the garment 900 is worn by the user.

The fourth support member 906 connects between the lower portion 992 of the protective cup support 914 and the waistband 912. The fourth support member 906 includes a first end 1012 which connects to the lower portion 992 of the protective cup support 914, and a second end 1014 which connects to the rear portion 976 of the waistband 912. The fourth support member 906 maintains the lower portion 992 of the protective cup support 914 and the protective cup 916 in a preferred position relative to the user's body. In an example embodiment, the fourth support member 906 stabilizes the protective cup support 914 and the protective cup 916 in forward, backward and vertical directions when the garment 900 is worn by the user.

The end 1000 of the first support member 918, the end 1004 of the second support member 920, the ends 1008, 1010 of the third support member 922 and the ends 1012, 1014 of the fourth support member 906 may include an elastic component having sufficient elastic tension to maintain the lower portion 992 of the protective cup support 914 and the protective cup 916 in a preferred position and reduce movement of the support 914 and the cup 916 in forward, backward, lateral and vertical directions. The ends 1002, 1006 of the first and second support members 918, 920 may include an elastic component having sufficient elastic tension to maintain the side portions 994, 996 of the protective cup support 914 and the protective cup 916 in a preferred position and reduce movement of the support 914 and the cup 916 in lateral or side-to-side directions.

It should be appreciated that the waistband 912, the protective cup support 914, the first support member 918, the second support member 920, the third support member 922 and the fourth support member 906 may be made from similar materials as the waistband 12, the protective cup support 14, the first support member 18, the second support member 20 and the third support member 22 described above with respect to FIGS. 1 to 3.

In an example embodiment, the garment 900 may be adapted to connect to the garment 700. For example, the garment 900 may be connected to the garment 700 by a suitable connector or fastener such that the garments 700, 900 function as a single garment. In an example embodiment, the garment 500 may be adapted to connect to the garment 700. For example, the garment 500 may be connected to the garment 700 by a suitable connector or fastener such that the garments 500, 700 function as a single garment.

It should be understood that various changes and modifications to the example embodiments described herein will be apparent to those skilled in the art. Such changes and modifications may be made without departing from the spirit and scope of the present subject matter and without diminishing its intended advantages. For example, different example embodiments or portions thereof may be combined or interchanged with one another. It is therefore intended that such changes and modifications be covered by the appended claims.

The invention is claimed as follows:

1. An apparatus comprising:
    an annular support member, the annular support member including a front region and a rear region;
    a protective cup support configured to receive a protective cup and having an approximately triangular shape, the protective cup support including an upper portion connected to the front region of the annular support member, a lower portion, a first side portion, and a second side portion, the upper portion being an edge of the triangular shape and the lower portion being a vertex of the triangular shape;

a first support strap including a first end connected directly to the lower portion of the protective cup support and a second end connected directly to the first side portion of the protective cup support proximate the upper portion of the protective cup support;

a second support strap including a first end connected directly to the lower portion of the protective cup support and a second end connected directly to the second side portion of the protective cup support proximate the upper portion of the protective cup support;

a third support strap including a first end connected directly to the lower portion of the protective cup support and a second end connected to the rear region of the annular support member and a fourth support strap including a first end connected to the lower portion of the protective cup support and a second end connected to the rear region of the annular support member.

2. The apparatus of claim 1, wherein the first end of the first support strap, the first end of the second support strap, and the first end of the third support strap each connect to the lower portion of the protective cup support at a same location or at a substantially same location.

3. The apparatus of claim 1, wherein the upper portion of the protective cup support is directly connected to the annular support member.

4. An apparatus comprising:

an inner garment including an annular support member and first and second leg openings connected to the annular support member, the annular support member including a front region and a rear region;

a protective cup support configured to receive a protective cup and having an approximately triangular shape, the protective cup support including an upper portion connected to the front region of the annular support member, a lower portion, a first side portion, and a second side portion, the upper portion being an edge of the triangular shape and the lower portion being a vertex of the triangular shape;

a first support strap including a first end connected to the lower portion of the protective cup support and a second end connected directly to the first side portion of the protective cup support proximate the upper portion of the protective cup support;

a second support strap including a first end connected to the lower portion of the protective cup support and a second end connected directly to the second side portion of the protective cup support proximate the upper portion of the protective cup support;

a third support strap including a first end connected to the lower portion of the protective cup support and a second end connected to the rear region of the annular support member and a fourth support strap including a first end connected to the lower portion of the protective cup support and a second end connected to the rear region of the annular support member.

5. The apparatus of claim 4, wherein the first end of the first support strap, the first end of the second support strap and the first end of the third support strap each connect to the lower portion of the protective cup support at a same location or at a substantially same location.

6. The apparatus of claim 4, wherein the inner garment includes at least one protective pad support, the at least one protective pad support including an opening which is configured to receive a protective pad.

* * * * *